(12) United States Patent
Bruce et al.

(10) Patent No.: US 8,053,574 B2
(45) Date of Patent: Nov. 8, 2011

(54) ORGANIC COMPOUNDS

(75) Inventors: Ian Bruce, Horsham (GB); Darren Mark Legrand, Horsham (GB); James Dale, Horsham (GB); Thomas Anthony Hunt, Horsham (GB)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/669,536

(22) PCT Filed: Jul. 16, 2008

(86) PCT No.: PCT/EP2008/059298
§ 371 (c)(1),
(2), (4) Date: Jan. 18, 2010

(87) PCT Pub. No.: WO2009/010530
PCT Pub. Date: Jan. 22, 2009

(65) Prior Publication Data
US 2010/0197682 A1    Aug. 5, 2010

(30) Foreign Application Priority Data
Jul. 18, 2007  (EP) .................................... 07112688

(51) Int. Cl.
| | | |
|---|---|---|
| *C07D 487/00* | (2006.01) | |
| *C07D 514/14* | (2006.01) | |
| *C07D 513/14* | (2006.01) | |
| *C07D 401/14* | (2006.01) | |
| *A61K 31/4427* | (2006.01) | |
| *A61K 31/4436* | (2006.01) | |
| *A61K 31/444* | (2006.01) | |
| *A01N 43/54* | (2006.01) | |
| *A61K 31/4439* | (2006.01) | |

(52) U.S. Cl. .......... 544/236; 544/33; 546/119; 546/121; 514/256; 514/300; 514/301; 514/302; 514/303

(58) Field of Classification Search ................ None
See application file for complete search history.

(56) References Cited

U.S. PATENT DOCUMENTS
2006/0142570 A1    6/2006  Herz et al.

FOREIGN PATENT DOCUMENTS
| | | |
|---|---|---|
| EP | 0 261 459 A2 | 3/1988 |
| WO | WO 01/27110 A2 | 4/2001 |
| WO | WO 01/57008 A1 | 8/2001 |
| WO | WO 2005/089763 A1 | 9/2005 |
| WO | WO 2005/113511 A1 | 12/2005 |
| WO | WO 2007/095558 A2 | 8/2007 |
| WO | WO 2006/038116 A2 | 1/2010 |

*Primary Examiner* — Kamal Saeed
*Assistant Examiner* — Nyeemah A Grazier
(74) *Attorney, Agent, or Firm* — Michael G. Smith

(57) ABSTRACT

Phosphatidylinositol (PI) 3-kinase inhibitor compounds, their pharmaceutically acceptable salts, and prodrugs thereof; compositions of the new compounds, either alone or in combination with at least one additional therapeutic agent, with a pharmaceutically acceptable carrier; and uses of the new compounds, either alone or in combination with at least one additional therapeutic agent, in the prophylaxis or treatment of proliferative diseases characterized by the abnormal activity of growth factors, protein serine/threonine kinases, and phospholipid kinases.

16 Claims, No Drawings

ORGANIC COMPOUNDS

This application is a U.S. National Phase filing of International Application Ser. No. PCT/EP2008/059298 filed 16 Jul. 2008 and claims priority to E.P. Application Ser. No. 07112688.2 filed 18 Jul. 2007, the contents of which are incorporated herein by reference in their entirety.

SUMMARY OF THE INVENTION

The preferred embodiments provide new phosphatidylinositol 3-kinase (PI3K) inhibitor compounds, pharmaceutical formulations that include the compounds, methods of inhibiting phosphatidylinositol 3-kinase (PI3K), and methods of treating proliferative diseases.

Thus, there is provided a compound of formula (A)

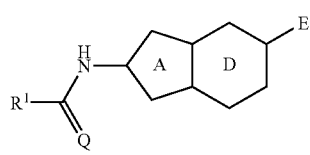

(A)

wherein:

ring AD is 5,6-bicyclic aromatic heterocyclic ring, where A is a 5-membered aromatic heterocyclic ring containing one or more O, S and N ring atoms fused to ring D, which is a phenyl ring or a 6-membered aromatic heterocyclic ring containing one, two or three nitrogen ring atoms, where ring AD is substituted by $R^2$, $R^3$, $R^4$ and $R^5$;

E is a $C_6$-$C_{10}$-aryl, a 5 to 10-membered heteroaryl or halogen, wherein the rings are optionally substituted by $R^6$, $R^7$ and $R^8$;

Q is O or S;

$R^1$ is selected from the group consisting of hydrogen, alkyl, substituted alkyl, alkenyl, substituted alkenyl, alkynyl, substituted alkynyl, alkoxy, substituted alkoxy, amino, substituted amino, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, and alkylamino;

$R^2$ and $R^3$ are independently selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, and substituted alkylthio;

$R^4$ and $R^5$ are independently selected from the group consisting of hydrogen, halogen, cyano, nitro, amino, substituted amino, alkoxy, substituted alkoxy, alkyl, and substituted alkyl;

$R^6$ is selected from the group consisting of hydrogen, halogen, cyano, nitro, alkoxy, substituted alkoxy, alkyl, and substituted alkyl; and $R^7$ and $R^8$ are independently selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acyloxy, aminocarbonyl, aminothiocarbonyl, aminothiocarbonylamino, aminocarbonyloxy, aminosulfonyl, aminosulfonyloxy, aminosulfonylamino, amidino, carboxyl, carboxyl ester, (carboxyl ester)oxy, cyano, halo, hydroxy, nitro, $SO_3H$, sulfonyl, substituted sulfonyl, sulfonyloxy, thioacyl, thiol, alkylthio, and substituted alkylthio; or $R^7$ and $R^8$ together with the ring atoms to which they are attached form a 5 to 8 membered carbocyclic or heterocyclic group.

In embodiments where ring D is phenyl, ring A suitably contains two heteroatoms selected from N, S and O. More suitably, ring A contains a nitrogen atom and one further heteroatom selected from N, S and O when ring D is phenyl.

In an embodiment of the invention, there is provided a compound of formula (A1)

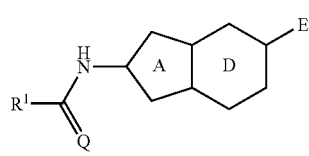

A1 where ring AD is selected from

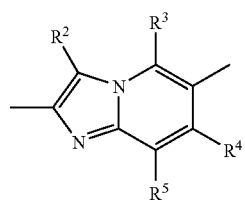

A1

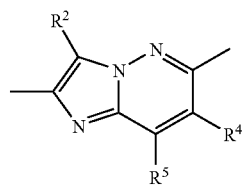

A2

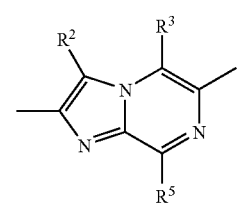

A3

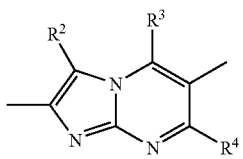
A4

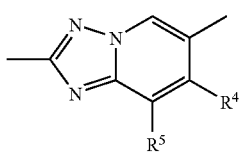
A5

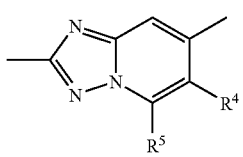
A6

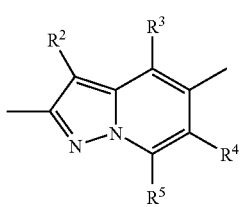
A7

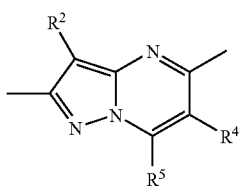
A8

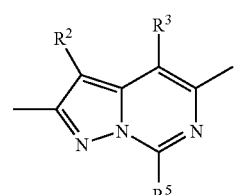
A9

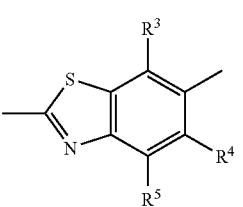
A10

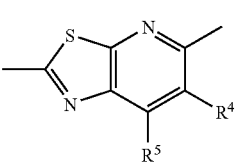
A11

A12

E is selected from

Q is O or S;

$R^1$ is selected from the group consisting of hydrogen, alkyl, substituted alkyl, alkenyl, substituted alkenyl, alkynyl, substituted alkynyl, alkoxy, substituted alkoxy, amino, substituted amino, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, and alkylamino;

$R^2$ and $R^3$ are independently selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, and substituted alkylthio;

$R^4$ and $R^5$ are independently selected from the group consisting of hydrogen, halogen, cyano, nitro, amino, substituted amino, alkoxy, substituted alkoxy, alkyl, and substituted alkyl;

$R^6$ is selected from the group consisting of hydrogen, halogen, cyano, nitro, alkoxy, substituted alkoxy, alkyl, and substituted alkyl; and $R^7$ is selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acyloxy, aminocarbonyl, aminothiocarbonyl, aminothiocarbonylamino, aminocarbonyloxy, aminosulfonyl, aminosulfonyloxy, aminosulfonylamino, amidino, carboxyl, carboxyl ester, (carboxyl ester)oxy, cyano, halo, hydroxy, nitro, $SO_3H$, sulfonyl, substituted sulfonyl, sulfonyloxy, thioacyl, thiol, alkylthio, and substituted alkylthio;

$R^{20}$ is selected from the group consisting of $C_{1-6}$-alkyl and substituted $C_{1-6}$-alkyl;

$L^1$ is N or $CR^9$;

$L^2$ is N or $CR^8$;

$L^3$ is N or $CR^{9a}$;

$R^8$ and $R^9$ are independently selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acyloxy, aminocarbonyl, aminothiocarbonyl, aminothiocarbonylamino, aminocarbonyloxy, aminosulfonyl, aminosulfonyloxy, aminosulfonylamino, amidino, carboxyl, carboxyl ester, (carboxyl ester)oxy, cyano, halo, hydroxy, nitro, $SO_3H$, sulfonyl, substituted sulfonyl, sulfonyloxy, thioacyl, thiol, alkylthio and substituted alkylthio; and $R^{9a}$ is selected from the group consisting of hydrogen, halogen, cyano, nitro, alkoxy, substituted alkoxy, alkyl and substituted alkyl, with the further options that when $L^1$ is $CR^9$, then $R^9$ and $R^6$ together with the carbon atoms to which they are attached may form a 5 to 8 membered ring fused to ring E, wherein the 5 to 8 membered ring is selected from cycloalkyl, aryl, heterocyclic and heteroaryl; and when $L^1$ is $CR^9$ and $L^2$ is $CR^8$, then $R^8$ and $R^9$ together with the carbon atoms to which they are attached may form a 5 to 8 membered ring fused to ring E, wherein the 5 to 8 membered ring is selected from cycloalkyl, aryl, heterocyclic and heteroaryl.

Suitably, not more than three of $R^6$, $R^7$, $R^8$, $R^9$ and $R^{9a}$ may be other than hydrogen.

In certain embodiments of the invention, $R^2$, $R^3$, $R^4$, $R^5$, $R^6$, $R^7$, $R^8$, $R^9$, $R^{9a}$, $R^{20}$, $L^1$, $L^2$ and $L^3$ are as defined above in any embodiment and $R^1$ is —Z—Y—$R^{10}$, wherein Z is $NHCH_2C(R^{11})R^{12}$, Y is a bond or —CON($R^{13}$)— $R^{10}$ is $C_1$-$C_6$-alkylaminocarbonyl, $C_1$-$C_6$-alkoxycarbonyl, where each alkyl is independently optionally substituted by one or more halo, hydroxyl or $C_1$-$C_6$-alkoxy groups groups, or $R^{10}$ is a mono-cyclic heteroaromatic ring having one or more ring heteroatoms selected from the group consisting of oxygen, nitrogen and sulphur, said ring being optionally substituted by one or more halo, hydroxyl, $C_1$-$C_6$-alkyl or $C_1$-$C_6$-alkoxy groups, where said alkyl and alkoxy are optionally further substituted by one or more halo, hydroxyl or $C_1$-$C_6$-alkoxy groups;

$R^{11}$ and $R^{12}$ are independently selected from hydrogen, halo, hydroxy and $C_1$-$C_6$-alkyl where said alkyl group is optionally substituted by one or more halo, hydroxyl or $C_1$-$C_6$-alkoxy groups; and $R^{13}$ is hydrogen or $C_1$-$C_6$-alkyl.

In further embodiments of the invention, $R^1$, $R^2$, $R^3$, $R^4$, $R^5$, $R^6$, $R^7$, $R^9$, $R^{9a}$, $R^{20}$, $L^1$, $L^2$ and $L^3$ are as defined above in any embodiment and $R^8$ is selected from the group consisting of hydrogen, alkyl, —CO—$R^{8a}$, substituted alkyl, and a three- to seven-membered ring selected from the group consisting of cycloalkyl, substituted cycloalkyl, heterocyclyl, and substituted heterocyclyl; and $R^{8a}$ is selected from the group consisting of alkyl, substituted alkyl, alkoxy, substituted alkoxy, amino, substituted amino, and alkylamino.

In still further embodiments of the invention, $R^1$, $R^2$, $R^3$, $R^4$, $R^5$, $R^6$, $R^7$, $R^9$, $R^{9a}$, $L^1$, $L^2$ and $L^3$ are as defined above in any embodiment and $R^{20}$ is methyl, trihalomethyl or benzyl.

In yet still further embodiments of the invention, $R^1$, $R^2$, $R^3$, $R^4$, $R^5$, $R^6$, $R^7$, $R^9$, $R^{9a}$, $R^{20}$ and $L^2$ are as defined above in any embodiment, $L^1$ is $CR^9$ and $L^2$ is $CR^8$, with the further options that $R^8$ and $R^9$ together with the carbon atoms to which they are attached may form a 5 membered heterocycle or a phenyl group fused to the ring E.

In further embodiments of the invention, $R^1$, $R^2$, $R^3$, $R^4$, $R^5$, $R^6$, $R^7$, $R^9$, $R^{9a}$, $R^{20}$, $L^2$ and $L^3$ are as defined above in any embodiment and $L^1$ is $CR^9$, with the further options that $R^6$ and $R^9$ together with the carbon atoms to which they are attached may form a phenyl group fused to the ring E.

In a suitable embodiment of a compound of formula (A), the present invention provides compounds of formula (IV), or tautomers, or stereoisomers, or pharmaceutically acceptable salts thereof,

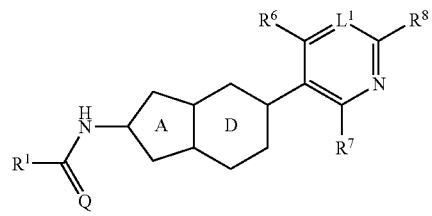

IV

Wherein,
Ring AD is selected from

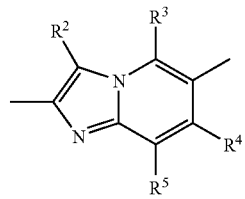

A1

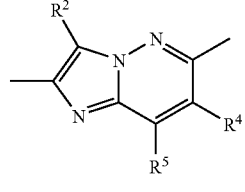

A2

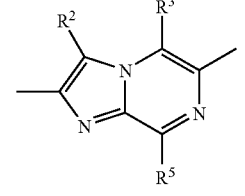

A3

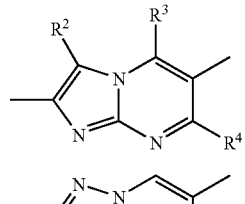

A4

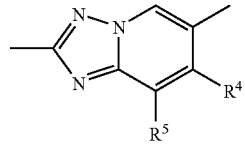

A5

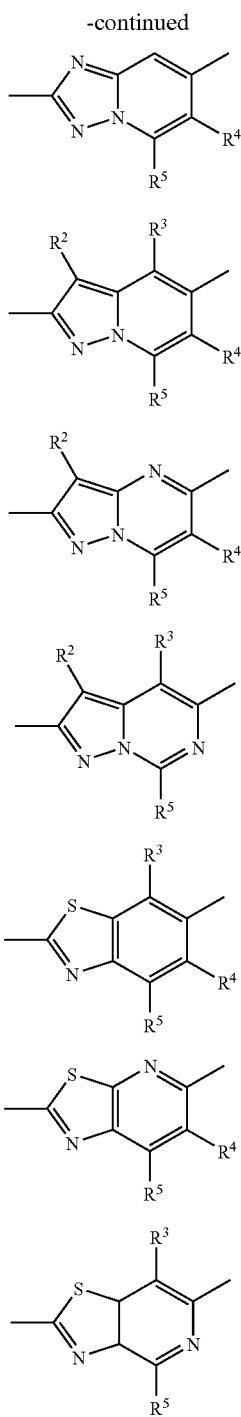

Q is O or S;
L¹ is CR⁹ or N;
R¹ represents —Z—Y—R¹⁰;
Z is NHCH₂C(R¹¹)R¹²—
Y is a bond or —CON(R¹³)—;
R² and R³ are independently selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, SO₃H, sulfonyl, substituted sulfonyl, sulfonyloxy, thioacyl, thiol, alkylthio, and substituted alkylthio;

R⁴ and R⁵ are independently selected from the group consisting of hydrogen, halogen, cyano, nitro, amino, substituted amino, alkoxy, substituted alkoxy, alkyl, and substituted alkyl;

R⁶ is selected from the group consisting of hydrogen, halogen, cyano, nitro, alkoxy, substituted alkoxy, alkyl, and substituted alkyl;

R⁷ and R⁹ are independently selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acyloxy, aminocarbonyl, aminothiocarbonyl, aminothiocarbonylamino, aminocarbonyloxy, aminosulfonyl, aminosulfonyloxy, aminosulfonylamino, amidino, carboxyl, carboxyl ester, (carboxyl ester)oxy, cyano, halo, hydroxy, nitro, SO₃H, sulfonyl, substituted sulfonyl, sulfonyloxy, thioacyl, thiol, alkylthio, and substituted alkylthio;

R⁸ is selected from the group consisting of hydrogen, alkyl, —CO—R⁸ᵃ, substituted alkyl, and a three- to seven-membered ring selected from the group consisting of cycloalkyl, substituted cycloalkyl, heterocyclyl, and substituted heterocyclyl;

R⁸ᵃ is selected from the group consisting of alkyl, substituted alkyl, alkoxy, substituted alkoxy, amino, substituted amino, and alkylamino;

R¹⁰ is $C_1$-$C_6$-alkylaminocarbonyl, $C_1$-$C_6$-alkoxycarbonyl, where each alkyl is independently optionally substituted by one or more halo, hydroxyl or $C_1$-$C_6$-alkoxy groups groups, or R¹⁰ is a mono-cyclic heteroaromatic ring having one or more ring heteroatoms selected from the group consisting of oxygen, nitrogen and sulphur, said ring being optionally substituted by one or more halo, hydroxyl, $C_1$-$C_6$-alkyl or $C_1$-$C_6$-alkoxy groups, where said alkyl and alkoxy are optionally further substituted by one or more halo, hydroxyl or $C_1$-$C_6$-alkoxy groups;

R¹¹ and R¹² are independently selected from hydrogen, halo, hydroxy and $C_1$-$C_6$-alkyl where said alkyl group is optionally substituted by one or more halo, hydroxyl or $C_1$-$C_6$-alkoxy groups; and R¹³ is hydrogen or $C_1$-$C_6$-alkyl.

A further suitable embodiment of the present invention provides a compound of Formula V:

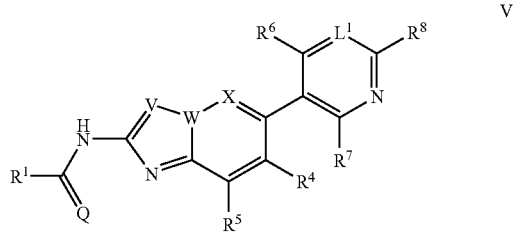

wherein:
Q is O or S;
X is $CR^3$ or N;
W is C or N;
V is $CR^2$, O, S or N;
$L^1$ is $CR^9$ or N;
$R^1$ represents —Z—Y—$R^{10}$;
Z is; $NHCH_2C(R^{11})R^{12}$;
Y is a bond or $CON(R^{13})$—;
$R^2$ and $R^3$ are independently selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, and substituted alkylthio;
$R^4$ and $R^5$ are independently selected from the group consisting of hydrogen, halogen, cyano, nitro, amino, substituted amino, alkoxy, substituted alkoxy, alkyl, and substituted alkyl;
$R^6$ is selected from the group consisting of hydrogen, halogen, cyano, nitro, alkoxy, substituted alkoxy, alkyl, and substituted alkyl;
$R^7$ and $R^9$ are independently selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acyloxy, aminocarbonyl, aminothiocarbonyl, aminothiocarbonylamino, aminocarbonyloxy, aminosulfonyl, aminosulfonyloxy, aminosulfonylamino, amidino, carboxyl, carboxyl ester, (carboxyl ester)oxy, cyano, halo, hydroxy, nitro, $SO_3H$, sulfonyl, substituted sulfonyl, sulfonyloxy, thioacyl, thiol, alkylthio, and substituted alkylthio;
$R^8$ is selected from the group consisting of hydrogen, alkyl, —CO—$R^{8a}$, substituted alkyl, and a three- to seven-membered ring selected from the group consisting of cycloalkyl, substituted cycloalkyl, heterocyclyl, and substituted heterocyclyl;
$R^{8a}$ is selected from the group consisting of alkyl, substituted alkyl, alkoxy, substituted alkoxy, amino, substituted amino, and alkylamino;
$R^{10}$ is $C_1$-$C_6$-alkylaminocarbonyl, $C_1$-$C_6$-alkoxycarbonyl, where each alkyl is independently optionally substituted by one or more halo, hydroxyl or $C_1$-$C_6$-alkoxy groups groups, or $R^{10}$ is a mono-cyclic heteroaromatic ring having one or more ring heteroatoms selected from the group consisting of oxygen, nitrogen and sulphur, said ring being optionally substituted by one or more halo, hydroxyl, $C_1$-$C_6$-alkyl or $C_1$-$C_6$-alkoxy groups, where said alkyl and alkoxy are optionally further substituted by one or more halo, hydroxyl or $C_1$-$C_6$-alkoxy groups;

$R^{11}$ and $R^{12}$ are independently selected from hydrogen, halo, hydroxy and $C_1$-$C_6$-alkyl where said alkyl group is optionally substituted by one or more halo, hydroxyl or $C_1$-$C_6$-alkoxy groups; and
$R^{13}$ is hydrogen or $C_1$-$C_6$-alkyl.
In a suitable embodiment of a compound of formula A, E is suitably selected from the group

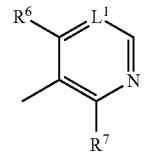

where $L^1$ is N or $CR^9$ and $R^6$, $R^7$ and $R^9$ are as defined in any embodiment herein.

In the embodiments mentioned herein, where only certain variables are defined, it is intended that the remainder of the variables are as defined in any embodiment herein. Thus, the invention provides for the combination of sub-definitions of variables.

A suitable further embodiment of the invention provides compounds, stereoisomers, tautomers, or pharmaceutically acceptable salts of Formula I and the related compositions and methods wherein Formula I is:

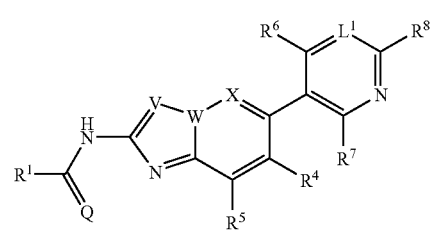

I wherein:
Q is O or S;
X is $CR^3$ or N;
W is C or N;
V is $CR^2$, O or S;
$L^1$ is $CR^9$ or N;
$R^1$ is selected from the group consisting of hydrogen, alkyl, substituted alkyl, alkenyl, substituted alkenyl, alkynyl, substituted alkynyl, alkoxy, substituted alkoxy, amino, substituted amino, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, and alkylamino;
$R^2$ and $R^3$ are independently selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, SO₃H, sulfonyl, substituted sulfonyl, sulfonyloxy, thioacyl, thiol, alkylthio, and substituted alkylthio;

$R^4$ and $R^5$ are independently selected from the group consisting of hydrogen, halogen, cyano, nitro, amino, substituted amino, alkoxy, substituted alkoxy, alkyl, and substituted alkyl;

$R^6$ is selected from the group consisting of hydrogen, halogen, cyano, nitro, alkoxy, substituted alkoxy, alkyl, and substituted alkyl;

$R^7$ and $R^9$ are independently selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acyloxy, aminocarbonyl, aminothiocarbonyl, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, SO₃H, sulfonyl, substituted sulfonyl, sulfonyloxy, thioacyl, thiol, alkylthio, and substituted alkylthio;

$R^8$ is selected from the group consisting of hydrogen, alkyl, —CO—$R^{8a}$, substituted alkyl, and a three- to seven-membered ring selected from the group consisting of cycloalkyl, substituted cycloalkyl, heterocyclyl, and substituted heterocyclyl; and $R^{8a}$ is selected from the group consisting of alkyl, substituted alkyl, alkoxy, substituted alkoxy, amino, substituted amino, and alkylamino.

In another embodiment of Formula I, when V is O or S, W is C. In a more particular embodiment, when V is $CR^2$, W is N.

A further embodiment provides a compound of Formula II, a stereoisomer, tautomer, or pharmaceutically acceptable salt thereof:

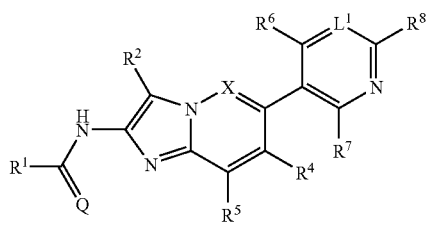

II wherein:
Q is O or S;
X is $CR^3$ or N;
$L^1$ is $CR^9$ or N;
$R^1$ is selected from the group consisting of hydrogen, alkyl, substituted alkyl, alkenyl, substituted alkenyl, alkynyl, substituted alkynyl, alkoxy, substituted alkoxy, amino, substituted amino, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, and alkylamino;

$R^2$ and $R^3$ are independently selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, SO₃H, sulfonyl, substituted sulfonyl, sulfonyloxy, thioacyl, thiol, alkylthio, and substituted alkylthio;

$R^4$ and $R^5$ are independently selected from the group consisting of hydrogen, halogen, cyano, nitro, amino, substituted amino, alkoxy, substituted alkoxy, alkyl, and substituted alkyl;

$R^6$ is selected from the group consisting of hydrogen, halogen, cyano, nitro, alkoxy, substituted alkoxy, alkyl, and substituted alkyl;

$R^7$ and $R^9$ are independently selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acyloxy, aminocarbonyl, aminothiocarbonyl, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, SO₃H, sulfonyl, substituted sulfonyl, sulfonyloxy, thioacyl, thiol, alkylthio, and substituted alkylthio;

$R^8$ is selected from the group consisting of hydrogen, alkyl, —CO—$R^{8a}$, substituted alkyl, and a three- to seven-membered ring selected from the group consisting of cycloalkyl, substituted cycloalkyl, heterocyclyl, and substituted heterocyclyl; and $R^{8a}$ is selected from the group consisting of alkyl, substituted alkyl, alkoxy, substituted alkoxy, amino, substituted amino, and alkylamino.

An embodiment of the invention provides for compounds of Formula II, wherein $R^1$ is —Z—Y—$R^{10}$;
Z is $NHCH_2C(R^{11})R^{12}$;
Y is a bond or —$CON(R^{13})$—;
$R^{10}$ is $C_1$-$C_6$-alkylaminocarbonyl, $C_1$-$C_6$-alkoxycarbonyl, where each alkyl is independently optionally substituted by one or more halo, hydroxyl or $C_1$-$C_6$-alkoxy groups groups, or $R^{10}$ is a mono-cyclic heteroaromatic ring having one or more ring heteroatoms selected from the group consisting of oxygen, nitrogen and sulphur, said ring being optionally substituted by one or more halo, hydroxyl, $C_1$-$C_6$-alkyl or $C_1$-$C_6$-alkoxy groups, where said alkyl and alkoxy are optionally further substituted by one or more halo, hydroxyl or $C_1$-$C_6$-alkoxy groups;

$R^{11}$ and $R^{12}$ are independently selected from hydrogen, halo, hydroxy and $C_1$-$C_6$-alkyl where said alkyl group is optionally substituted by one or more halo, hydroxyl or $C_1$-$C_6$-alkoxy groups; and $R^{13}$ is hydrogen or $C_1$-$C_6$-alkyl.

A further embodiment provides for compounds of Formula II, wherein Y is a bond and $R^{10}$ is a mono-cyclic heteroaromatic ring having one or more ring heteroatoms selected from the group consisting of oxygen, nitrogen and sulphur, said ring being optionally substituted by one or more halo, hydroxyl, $C_1$-$C_6$-alkyl or $C_1$-$C_6$-alkoxy groups, where said alkyl and alkoxy are optionally further substituted by one or more halo, hydroxyl or $C_1$-$C_6$-alkoxy groups.

A further embodiment provides for compounds of Formula II, wherein $R^2$ is selected from the group consisting of hydrogen, chloro, bromo, methylamido-N-phenyl, fluorophenyl, phenyl, phenylalkynyl, aminomethylalkynyl, and amidophenyl.

An embodiment provides for compounds of Formula II, wherein $R^2$ is hydrogen.

A further embodiment provides for compounds of Formula II, wherein X is $CR^3$, more particularly, $R^3$ is hydrogen.

A further embodiment provides for compounds of Formula II, wherein $R^4$ is hydrogen.

A further embodiment provides for compounds of Formula II, wherein $R^5$ is hydrogen.

A further embodiment provides for compounds of Formula II, wherein $R^4$ and $R^5$ are both hydrogen A further embodiment provides for compounds of Formula II, wherein $R^6$ is hydrogen.

A further embodiment provides for compounds of Formula II, wherein $R^7$ is hydrogen.

A further embodiment provides for compounds of Formula II, wherein $R^8$ is hydrogen, alkyl or alkoxy.

A further embodiment provides for compounds of Formula II, wherein $R^8$ is hydrogen.

A further embodiment provides for compounds of Formula II, wherein $R^9$ is selected from the group consisting of hydrogen, trifluoromethyl, cyano, alkoxy, chloro, acyl, phenyl, phenyl substituted by a $C_{1-3}$alkyl group, heterocyclyloxy, fluoro, methyl, ethyl and bromo.

A further embodiment provides for compounds of Formula II, wherein $R^9$ is selected from the group consisting of hydrogen, trifluoromethyl, and methoxy.

A further embodiment provides for compound, stereoisomer, tautomer, or a pharmaceutically acceptable salt thereof selected from Table 1.

In another embodiment of a compound of formula (IV) or formula (V), ring AD is suitably ring A1

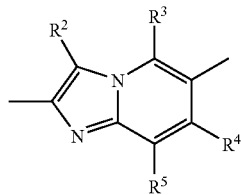

A1

In another embodiment of a compound of formula A or formula (IV) or formula (V), Q is suitably O.

In another embodiment of a compound of formula (IV) or formula (V), X is suitably CH, or N.

In another embodiment of a compound of formula (IV) or formula (V), W is suitably N.

In another embodiment of a compound of formula (IV) or formula (V), V is suitably CH.

In another embodiment of a compound of formula (IV) or formula (V), $L^1$ is suitably $CR^9$, where $R^9$ is suitably hydrogen, halo, hydroxyl, $C_1$-$C_6$-alkyl, $C_1$-$C_6$-alkoxy, cyano, nitro, aminocarbonyl, $C_1$-$C_6$-alkylaminocarbonyl, di-$C_1$-$C_6$-alkylaminocarbonyl, oxocarbonyl, hydroxycarbonyl, $C_1$-$C_6$-alkoxycarbonyl, sulfonyl, $C_1$-$C_6$-alkylsulfonyl, aminosulfonyl, $C_1$-$C_6$-alkylaminosulfonyl, di-$C_1$-$C_6$-alkylaminosulfonyl, sulfonylamino, $C_1$-$C_6$-alkylsulfonylamino, where said alkyl and alkoxy are optionally further substituted by one or more halo, hydroxyl, $C_1$-$C_6$-alkoxy or heterocycle, e.g. imidazole.

In another embodiment of a compound of formula (IV) or formula (V), $R^9$ is more suitably $C_1$-$C_6$-alkyl, optionally substituted by halo, e.g. fluoro (providing for example trifluoromethyl), or $R^9$ is cyano.

In another embodiment of a compound of formula (IV) or formula (V), Z is suitably —NH—$CH_2$—$CH_2$—, i.e. ethyleneamino.

In another embodiment of a compound of formula (IV) or formula (V), where Y is —$CON(R^{13})$—, $R^{13}$ is suitably hydrogen.

In another embodiment of a compound of formula (IV) or formula (V), where $R^1$ represents —Z—Y—$R^{10}$, Y represents a bond and $R^{10}$ is a mono-cyclic heteroaromatic ring, the ring is suitably an optionally substituted tetrazolyl, imidazolyl, oxazolyl, oxadiazolyl or isoxazolyl group, where the optional substituent is suitably $C_1$-$C_6$-alkyl, e.g. methyl, ethyl or isopropyl, optionally substituted by halo, e.g. fluoro, e.g. 2-fluoroethyl.

In another embodiment of a compound of formula (IV) or formula (V), where $R^1$ represents —Z—Y—$R^{10}$, Y represents $CON(R^{13})$ and $R^{10}$ is a mono-cyclic heteroaromatic ring, the ring is suitably an optionally substituted tetrazolyl group, where the optional substituent is suitably $C_1$-$C_6$-alkyl, e.g. methyl, ethyl or isopropyl.

In another embodiment of a compound of formula (IV) or formula (V), where $R^1$ represents —Z—Y—$R^{10}$, Y is a bond, $R^{10}$ also suitably represents $C_1$-$C_6$-alkylaminocarbonyl, e.g. t-butylaminocarbonyl, $C_1$-$C_6$-alkoxycarbonyl, e.g. t-butoxycarbonyl, where each alkyl is independently optionally substituted by one or more halo, hydroxyl or $C_1$-$C_6$-alkoxy groups groups, In another embodiment of a compound of formula (IV) or formula (V), $R^1$ is preferably 2-(2-ethyl-2H-tetrazol-5-yl)-ethylamino, 2-(2-isopropyl-2H-tetrazol-5-yl)-ethylamino, 2-(5-ethyl-tetrazol-2-yl)-ethylamio, 2-[2-(2-fluoro-ethyl)-2H-tetrazol-5-yl]ethylamino, 2-(1-ethyl-1H-imidazol-4-yl)-ethylamino, In another embodiment of a compound of formula (IV) or formula (V), $R^4$, $R^5$, $R^6$, $R^7$ and $R^8$ are suitably hydrogen.

Compounds of formula A which are also of formula X

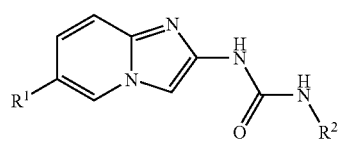

X are shown in Table 1 below, the method of preparation being described hereinafter. The table also shows mass spectrometry data. The Examples are in free form.

| R¹ | R² | M/s MH+ | Ki μM γ |
|---|---|---|---|
| 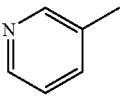 | 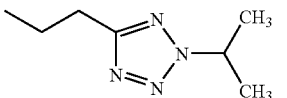 | 392.21 | 0.058 |
| 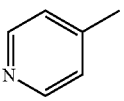 | 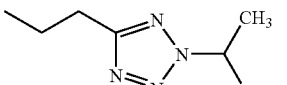 | 392.18 | 0.135 |
| 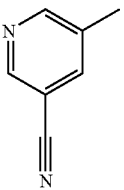 | 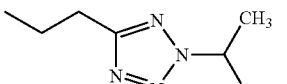 | 417.21 | 0.04 |
| 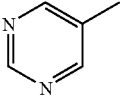 | 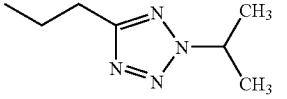 | 393.19 | 0.165 |
| 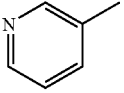 | 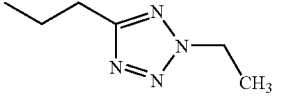 | 377.76 | 0.08 |
| 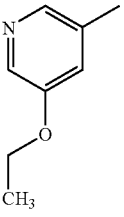 | 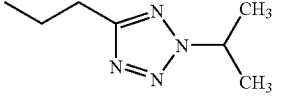 | 436.27 | 0.048 |
| 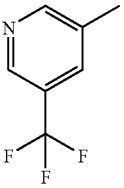 | 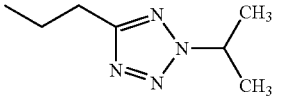 | 460.15 | 0.018 |
| 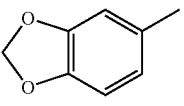 | 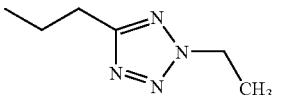 | 420.64 | 0.303 |
| 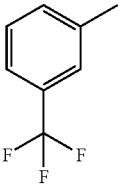 | 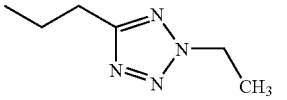 | 445.21 | 0.24 |

-continued
| R¹ | R² | M/s MH+ | Ki μM γ |
|---|---|---|---|
| 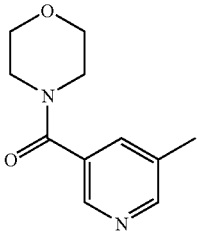 | 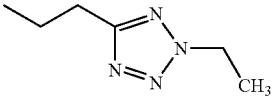 | 491.24 | 0.083 |
| 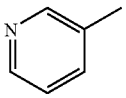 | 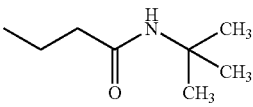 | 381.18 | 0.121 |
| 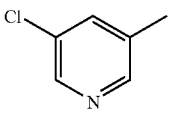 | 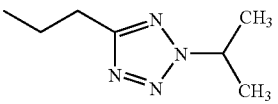 | 426.24 & 428.24 | 0.05 |
| 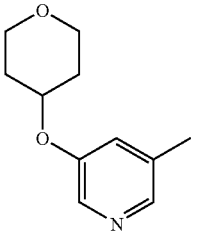 | 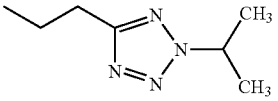 | 492.29 | 0.147 |
| 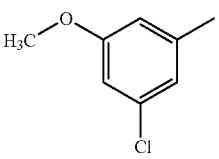 | 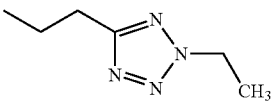 | 441.27 & 443.27 | 0.204 |
| 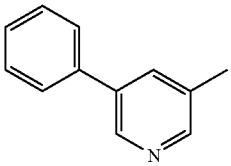 | 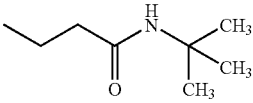 | 457.28 | 0.207 |
| 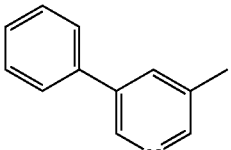 | 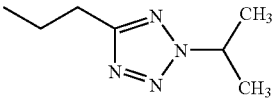 | 468.20 | 0.24 |
| 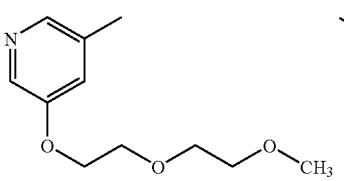 | 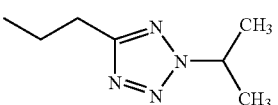 | 510.30 | 0.268 |

-continued
| R¹ | R² | M/s MH+ | Ki μM γ |
|---|---|---|---|
| 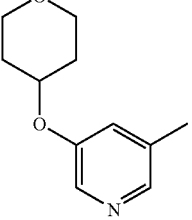 | 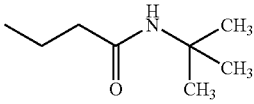 | 481.29 | 0.397 |
| 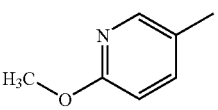 | 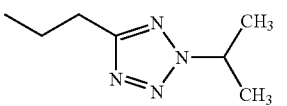 | 422.27 | 0.301 |
| 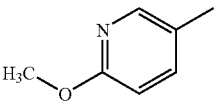 | 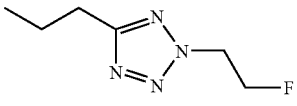 | 426.17 | 0.075 |
| 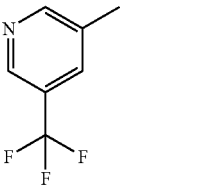 | 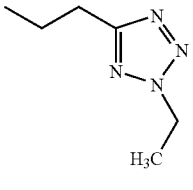 | 432.17 | 0.014 |
| 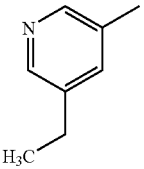 | 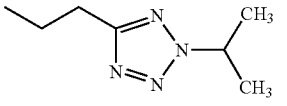 | 420.15 | 0.025 |
| 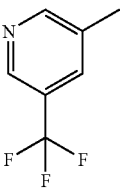 | 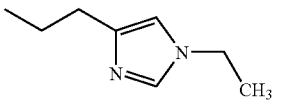 | 444.22 | 0.028 |
| 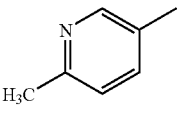 | 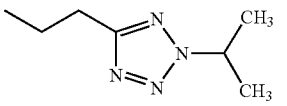 | 406.20 | 0.113 |
| 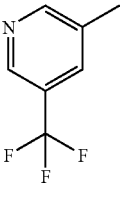 | 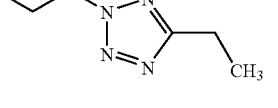 | 445.96 | 0.026 |
| 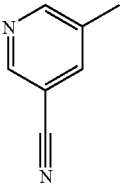 | 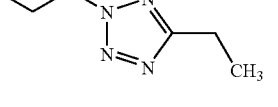 | 403.23 | 0.115 |

-continued
| R¹ | R² | M/s MH+ | Ki μM γ |
|---|---|---|---|
|  |  | 457.87 | 0.028 |
|  | 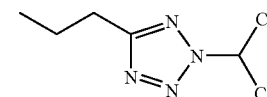 | 409.25 | 0.836 |
| 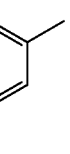 | 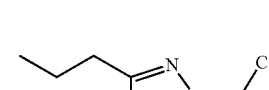 | 421.27 | 1.031 |
|  | 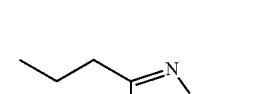 | 428.25 | 0.57 |
|  | 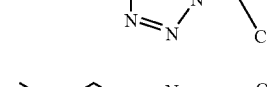 | 391.24 | 0.423 |
|  | 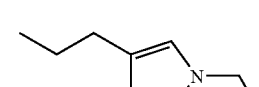 | 376.19 | 0.081 |
|  | 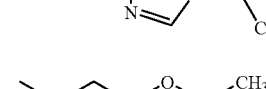 | 382.25 | 0.043 |
|  |  | 446.18 | 0.007 |
|  | 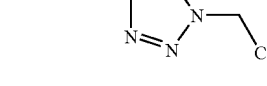 | 464.22 | 0.002 |
|  | 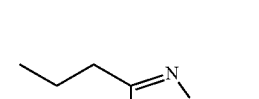 | 364.10 | 0.277 |

-continued

| R¹ | R² | M/s MH+ | Ki μM γ |
|---|---|---|---|
| 3-methylpyridine | 1-methyl-5-propyltetrazole | 364.1 | 0.584 |
| 3-methyl-5-(trifluoromethyl)pyridine | 2-methyl-5-propyltetrazole | 432.1 | 0.012 |
| 3-methyl-5-(2-methylphenyl)pyridine | 2-isopropyl-5-propyltetrazole | 482.3 | 1.122 |
| 1-methyl-4-methyl-pyrazole | 2-ethyl-5-propyltetrazole | 380.71 | 0.456 |
| 1-benzyl-4-methyl-pyrazole | 2-ethyl-5-propyltetrazole | 456.64 | 0.735 |
| 4-methylisoquinoline | 2-ethyl-5-propyltetrazole | 428.42 | 0.158 |
| 1-(5-methylpyridin-3-yl)ethanone | 2-isopropyl-5-propyltetrazole | 434.25 | 0.008 |
| 3-methylpyridine | 5-ethyl-1-propyltetrazole | 378.19 | 0.177 |
| Br | 2-ethyl-5-propyltetrazole | 379.11 | 0.911 |
| Br | 1-(5-(trifluoromethyl)isoxazol-3-yl)pentan-2-one | 407.03 | 4.98 |

-continued

| R¹ | R² | M/s MH+ | Ki μM γ |
|---|---|---|---|
| 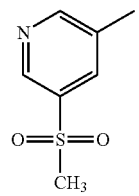 | 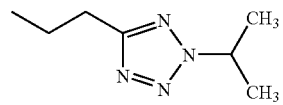 | 470.88 | 0.014 |
| 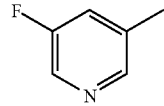 | 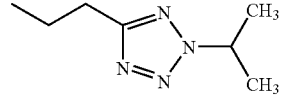 | 410.80 | 0.168 |
| 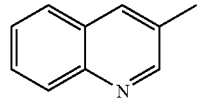 | 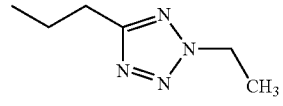 | 428.25 | 0.570 |

An aspect of the present invention provides a pharmaceutical composition comprising a pharmaceutically acceptable carrier and a therapeutically effective amount of a compound of Formula A, a stereoisomer, tautomer, or pharmaceutically acceptable salt thereof. Optionally, ring AD is suitably selected from

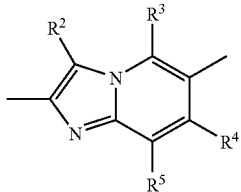
A1

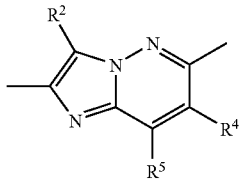
A2

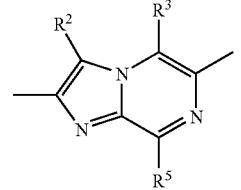
A3

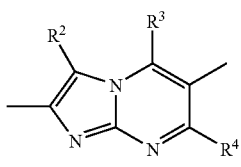
A4

-continued

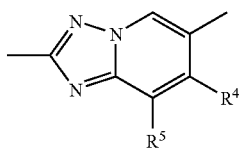
A5

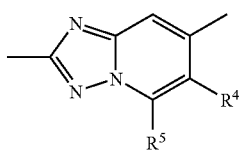
A6

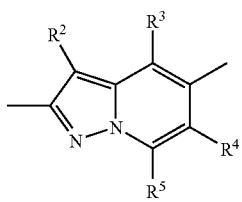
A7

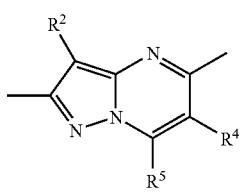
A8

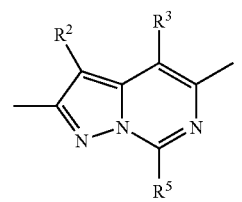
A9

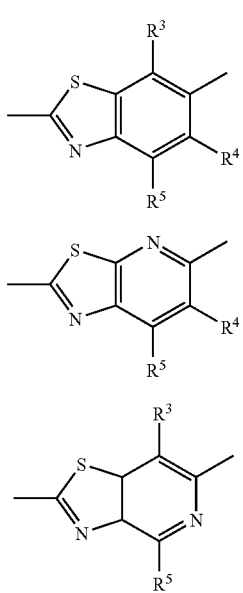

where R², R³, R⁴ and R⁵ are as defined in any embodiment herein.

DETAILED DESCRIPTION

Phosphatidylinositol-3-kinase (PI3K) mediates the signal from various growth factors to regulate cell proliferation and survival. A Serine/Threonine (Ser/Thr, or S/T) protein kinase, termed Akt, is identified as a downstream target of PI3-kinase. This protein kinase is recruited to the cell membrane by interaction of its pleckstrin homology domain with PI3K products, phosphatidylinositol-3,4,5-triphosphate (PIPS), and phosphatidylinositol-3,4-diphosphate (PIP₂), where it is activated by phosphorylation of its catalytic domain by 3-Phosphoinositide-dependent Kinase-1 (PDK-1). Akt is further activated by phosphorylation of a serine in its C-terminal hydrophobic motif by another kinase (PDK-2). The activation of Akt acts downstream to regulate additional kinases many of which are implicated in cellular processes that control survival, proliferation, metabolism and growth translation. PI3K can also drive cellular processes that impact transformation, cellular proliferation, cytoskeletal rearrangement and survival through a parallel pathway that does not involve Akt (Hennessy et al., *Nat. Rev. Drug Disc.* 4:988-1004 (2005)). Two of these pathways are activation of the small GTP-binding proteins Cdc42 and Rac1 and activation of the serum and glucocorticoid-inducible kinase (SGK). Cdc42 and Rac1, which regulate cytoskeletal movement and cell motility and can function as oncogenes when over-expressed, are also linked to the RAS pathway. Thus, PI3K activity generates 3'-phosphatidylinositol lipids that act as a nodal point to stimulate a diversity of downstream signaling pathways.

That these pathways impact cellular properties proliferation, survival, motility and morphology that are often disrupted in cancer, proliferative diseases, thrombotic diseases and inflammation, among others, dictates that compounds inhibiting PI3K (and isoforms thereof) have utility, either as a single agent or in combination, in the treatment of these diseases. In cancer, deregulation of the PI3K/Akt pathway is extensively documented, including overexpression of the PIK3 CA gene, activating mutations of the PIK3 CA gene, overexpression of Akt, mutations of PDK-1, and deletions/ inactivation of PTEN (Parsons et al., *Nature* 436:792 (2005); Hennessy et al., *Nat. Rev. Drug Disc.* 4:988 (2005); Stephens et al., *Curr. Opin. Pharmacol.* 5:1 (2005); Bonneau and Longy, *Human Mutation* 16:109 (2000) and Ali et al., *J. Natl. Can. Inst.* 91:1922 (1999)). Recent findings indicate that PIK3CA is frequently mutated (>30%) in various solid tumors in humans (Samuels and Ericson, *Curr. Opin. Oncology* 18:77 (2005)) and the most frequent of these mutations promote cell growth and invasion (Samuels et al., *Cancer Cell* 7:561 (2005), and are transforming (Kang et al., *Proc. Natl. Acad. Sci. USA* 102:802 (2005), Zhao et al., *Proc. Natl. Acad. Sci. USA* 102:18443 (2005)). Thus, inhibitors of PI3K, particularly of the p110a isoform encoded by PIK3CA and its mutations, will be useful in the treatment of cancers driven by these mutations and deregulations.

In its compounds aspects, the embodiments provide novel compounds that act as inhibitors of serine/threonine kinases, lipid kinases, and, more particularly, as inhibitors of phosphatidylinositol 3-kinase (PI3K) function. The compounds provided herein can be formulated into pharmaceutical formulations that are useful in treating patients with a need for an inhibitor of PI3K, especially, in particular embodiments, to provide compositions and methods for reducing cellular proliferation and increasing cell death in the treatment of cancer.

Throughout this application, the text refers to various embodiments of the present compounds, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

DEFINITIONS

The terms used herein are defined below.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl (CH₃—), ethyl (CH₃CH₂—), n-propyl (CH₃CH₂CH₂—), isopropyl ((CH₃)₂CH—), n-butyl (CH₃CH₂CH₂CH₂—), isobutyl ((CH₃)₂CHCH₂—), sec-butyl ((CH₃)(CH₃CH₂)CH—), t-butyl ((CH₃)₃C—), n-pentyl (CH₃CH₂CH₂CH₂CH₂—), and neopentyl ((CH₃)₃CCH₂—).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cyanate, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO₃H, substituted sulfonyl, sulfonyloxy, thioacyl, thiocyanate, thiol, alkylthio, and substituted alkylthio, wherein said substituents are defined herein.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Acyl includes the "acetyl" group $CH_3C(O)$—.

"Acylamino" refers to the groups —NRC(O)alkyl, —NRC(O)substituted alkyl, —NRC(O)cycloalkyl, —NRC(O)substituted cycloalkyl, —NRC(O)cycloalkenyl, —NRC(O)substituted cycloalkenyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic wherein R is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

"Amino" refers to the group —$NH_2$.

"Substituted amino" refers to the group $NR^{16}R^{17}$ where $R^{16}$ and $R^{17}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —$SO_2$-substituted cylcoalkyl, —$SO_2$-cycloalkenyl, —$SO_2$-substituted cylcoalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic and wherein $R^{16}$ and $R^{17}$ are optionally joined, together with the nitrogen bound thereto to form a heterocyclic or substituted heterocyclic group, provided that $R^{16}$ and $R^{17}$ are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein. When $R^{16}$ is hydrogen and $R^{17}$ is alkyl, the substituted amino group is sometimes referred to herein as alkylamino. When $R^{16}$ and $R^{17}$ are alkyl, the substituted amino group is sometimes referred to herein as dialkylamino. When referring to a monosubstituted amino, it is meant that either $R^{16}$ or $R^{17}$ is hydrogen but not both. When referring to a disubstituted amino, it is meant that neither $R^{16}$ nor $R^{17}$ are hydrogen.

"Hydroxyamino" refers to the group —NHOH.

"Alkoxyamino" refers to the group —NHO-alkyl wherein alkyl is defined herein.

"Aminocarbonyl" refers to the group —$C(O)NR^{16}R^{17}$ where $R^{16}$ and $R^{17}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where $R^{16}$ and $R^{17}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonyl" refers to the group —$C(S)NR^{16}R^{17}$ where $R^{16}$ and $R^{17}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where $R^{16}$ and $R^{17}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonylamino" refers to the group —NR'C(O) $NR^{16}R^{17}$ where R' is hydrogen or alkyl and $R^{16}$ and $R^{17}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where $R^{16}$ and $R^{17}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonylamino" refers to the group —NR'C(S) $NR^{16}R^{17}$ where R' is hydrogen or alkyl and $R^{16}$ and $R^{17}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where $R^{16}$ and $R^{17}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonyloxy" refers to the group —O—C(O)NR$^{16}$R$^{17}$ where R$^{16}$ and R$^{17}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R$^{16}$ and R$^{17}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyl" refers to the group —SO$_2$NR$^{16}$R$^{17}$ where R$^{16}$ and R$^{17}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R$^{16}$ and R$^{17}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyloxy" refers to the group —O—SO$_2$NR$^{16}$R$^{17}$ where R$^{16}$ and R$^{17}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R$^{16}$ and R$^{17}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonylamino" refers to the group —NR'SO$_2$NR$^{16}$R$^{17}$ where R' is hydrogen or alkyl and R$^{16}$ and R$^{17}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkyenyl, heteroaryl, substituted heteroaryl, heterocyclyl, and substituted heterocyclyl and where R$^{16}$ and R$^{17}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkyenyl, aryl, substituted aryl, heteroaryl, substituted heteroaryl, heterocyclic and substituted heterocyclic are as defined herein.

"Amidino" refers to the group —C(=NR$^{18}$)NR$^{16}$R$^{17}$ where R$^{16}$, R$^{17}$, and R$^{18}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R$^{16}$ and R$^{17}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cyanate, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiocyanate, thiol, alkylthio, and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Alkenyl" refers to alkenyl groups having from 2 to 6 carbon atoms and preferably 2 to 4 carbon atoms and having at least 1 and preferably from 1 to 2 sites of alkenyl unsaturation. Such groups are exemplified, for example, by vinyl, allyl, and but-3-en-1-yl.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein and with the proviso that any hydroxy substitution is not attached to a vinyl (unsaturated) carbon atom.

"Alkynyl" refers to alkynyl groups having from 2 to 6 carbon atoms and preferably 2 to 3 carbon atoms and having at least 1 and preferably from 1 to 2 sites of alkynyl unsaturation.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein and with the proviso that any hydroxy substitution is not attached to an acetylenic carbon atom.

"Azido" refers to the group —$N_3$.

"Hydrazino" refers to the group —$NHNH_2$.

"Substituted hydrazino" refers to the group —NRNR'R" where R, R', and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —$SO_2$-substituted cylcoalkyl, —$SO_2$-cycloalkenyl, —$SO_2$-substituted cylcoalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic and wherein R' and R" are optionally joined, together with the nitrogen bound thereto to form a heterocyclic or substituted heterocyclic group, provided that R' and R" are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

"Cyanate" refers to the group $OCN^-$.

"Thiocyanate" refers to the group $SCN^-$.

"Carbonyl" refers to the divalent group —C(O)— which is equivalent to —C(=O)—.

"Carboxyl" or "carboxy" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

"(Carboxyl ester)amino" refers to the group —NR—C(O)O-alkyl, substituted —NR—C(O)O-alkyl, —NR—C(O)O-alkenyl, —NR—C(O)O-substituted alkenyl, —NR—C(O)O-alkynyl, —NR—C(O)O-substituted alkynyl, —NR—C(O)O-aryl, —NR—C(O)O-substituted aryl, —NR—C(O)O-cycloalkyl, —NR—C(O)O-substituted cycloalkyl, —NR—C(O)O-cycloalkenyl, —NR—C(O)O-substituted cycloalkenyl, —NR—C(O)O-heteroaryl, —NR—C(O)O-substituted heteroaryl, —NR—C(O)O-heterocyclic, and —NR—C(O)O-substituted heterocyclic wherein R is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

"(Carboxyl ester)oxy" refers to the group —O—C(O)O-alkyl, substituted —O—C(O)O-alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

"Cyano" and "carbonitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, and cyclooctyl.

"Cycloalkenyl" refers to non-aromatic cyclic alkyl groups of from 3 to 10 carbon atoms having single or multiple cyclic rings and having at least one >C=C< ring unsaturation and preferably from 1 to 2 sites of >C=C< ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cyanate, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiocyanate, thiol, alkylthio, and substituted alkylthio, wherein said substituents are defined herein.

"Cycloalkyloxy" refers to —O-cycloalkyl.

"Substituted cycloalkyloxy refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy refers to —O-(substituted cycloalkenyl).

"Cycloalkenylthio" refers to —S-cycloalkenyl.

"Substituted cycloalkenylthio" refers to —S-(substituted cycloalkenyl).

"Guanidino" refers to the group —NHC(=NH)NH$_2$.

"Substituted guanidino" refers to —NR$^{13}$C(=NR$^{13}$)N(R$^{13}$)$_2$ where each R$^{13}$ is independently selected from the group consisting of hydrogen, alkyl, substituted alkyl, aryl, substituted aryl, heteroaryl, substituted heteroaryl, heterocyclyl, and substituted heterocyclyl and two R$^{13}$ groups attached to a common guanidino nitrogen atom are optionally joined together with the nitrogen bound thereto to form a heterocyclic or substituted heterocyclic group, provided that at least one R$^{13}$ is not hydrogen, and wherein said substituents are as defined herein.

"Halo" or "halogen" refers to fluoro, chloro, bromo and iodo.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or unsaturated group having a single ring or multiple condensed rings, including fused bridged and spiro ring systems, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group —NO$_2$.

"Oxo" refers to the atom (=O).

"Spirocycloalkyl" refers to divalent cyclic groups from 3 to 10 carbon atoms having a cycloalkyl ring with a spiro union (the union formed by a single atom which is the only common member of the rings) as exemplified by the following structure:

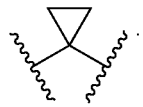

"Spirocyclyl" refers to divalent cyclic groups having a cycloalkyl or heterocyclyl ring with a spiro union, as described for spirocycloalkyl.

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cylcoalkyl, —SO$_2$-cycloalkenyl, —SO$_2$-substituted cylcoalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Substituted sulfonyl includes groups such as methyl —SO$_2$—, phenyl —SO$_2$—, and 4-methylphenyl —SO$_2$—.

"Sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cylcoalkyl, —OSO$_2$-cycloalkenyl, —OSO$_2$-substituted cylcoalkenyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thiol" refers to the group —SH.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring —N— moiety such as pyrazoles, imidazoles, benzimidazoles, triazoles, and tetrazoles.

"Patient" refers to mammals and includes humans and non-human mammals.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate.

"Prodrug" refers to any derivative of a compound of this invention that is capable of directly or indirectly providing a compound of this invention or an active metabolite or residue thereof when administered to a subject. Particularly favored derivatives and prodrugs are those that increase the bioavailability of the compounds of this invention when such compounds are administered to a subject (e.g., by allowing an orally administered compound to be more readily absorbed into the blood) or which enhance delivery of the parent compound to a biological compartment (e.g., the brain or lymphatic system) relative to the parent species. Prodrugs include ester forms of the compounds of the invention. Examples of ester prodrugs include formate, acetate, propionate, butyrate, acrylate, and ethylsuccinate derivatives. An general overview of prodrugs is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease.

Unless indicated otherwise, the nomenclature of substituents that are not explicitly defined herein are arrived at by naming the terminal portion of the functionality followed by the adjacent functionality toward the point of attachment. For example, the substituent "arylalkyloxycabonyl" refers to the group (aryl)-(alkyl)-O—C(O)—.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group etc.) are not intended for inclusion herein. In such cases, the maximum number of such substitutions is three. For example, serial substitutions of substituted aryl groups with two other substituted aryl groups are limited to substituted aryl-(substituted aryl)-substituted aryl.

Similarly, it is understood that the above definitions are not intended to include impermissible substitution patterns (e.g., methyl substituted with 5 fluoro groups). Such impermissible substitution patterns are well known to the skilled artisan.

Indications

In other aspects, the preferred embodiments provide for methods for manufacture of PI3K inhibitor compounds. It is further contemplated that, in addition to the compounds as defined herein, intermediates, and their corresponding methods of syntheses are included within the scope of the embodiments.

Another embodiment provides a method of inhibiting phosphorylation of Akt comprising administering a compound as defined herein to a human in need thereof. Another embodiment provides a method of treating cancer responsive to inhibition of phosphorylation of Akt, comprising administering a compound as defined herein. Another embodiment provides a method of inhibiting phosphorylation of Akt comprising contacting a cell with a compound as defined herein.

Another embodiment provides for a method for inhibiting phosphorylation of a substrate selected from phosphatidylinositol (PI), phosphatidylinositol phosphate (PIP), or phosphatidylinositol diphosphate (PIP$_2$), comprising exposing said substrate and a kinase thereof to a compound as defined herein.

Another embodiment provides a method of inhibiting phosphorylation of Akt comprising orally administering a compound as defined herein to a human in need thereof. In a more particular embodiment the human is suffering from cancer. In a more particular embodiment the cancer is responsive to treatment with a compound that inhibits phosphorylation of Akt. In another embodiment the compound is orally bioavailable.

Another embodiment provides a method of treating cancer comprising orally administering a compound as defined herein, wherein said compound is capable of inhibiting activity of pAkt.

In some embodiments of the method of inhibiting PI3K using a PI3K inhibitor compound of the embodiments, the $IC_{50}$ value of the compound is less than or equal to about 1 mM with respect to PI3K. In other such embodiments, the $IC_{so}$ value is less than or equal to about 100 µM, is less than or equal to about 25 µM, is less than or equal to about 10 µM, is less than or equal to about 1 µM, is less than or equal to about 0.1 µM, is less than or equal to about 0.050 µM, or is less than or equal to about 0.010 W.

Some embodiments provide methods of inhibiting phosphorylation of Akt using a compound of the embodiments having an $EC_{50}$ value of less than about 10 µM with respect to inhibition of pAKT. In another more particular embodiment, the compound has an $EC_{50}$ value of less than about 1 µM with respect to inhibition of pAKT. In a more particular embodiment still, the compound has an $EC_{50}$ value of less than about 0.5 µM with respect to inhibition of pAKT. In an even more particular embodiment, the compound has an ECso value of less than about 0.1 µM with respect to inhibition of pAKT.

In certain embodiments, a compound is capable of inhibition of phosphorylation of Akt. In certain embodiments, a compound is capable of inhibition of phosphorylation of Akt in a human or animal subject (i.e., in vivo).

In one embodiment, a method of reducing pAkt activity in a human or animal subject is provided. In the method, a compound of the preferred embodiments is administered in an amount effective to reduce pAkt activity.

In some embodiments of the method of inhibiting PI3K using a PI3K inhibitor compound of the embodiments, the $IC_{50}$ value of the compound is between about 1 nM to about 10 nM. In other such embodiments, the $IC_{50}$ value is between about 10 nM to about 50 nM, between about 50 nM to about 100 nM, between about 100 nM to about 1 µM, between about 1 µM to about 25 µM, or is between about 25 µM to about 100 W.

Another embodiment provides methods of treating a PI3K-mediated disorder. In one method, an effective amount of a PI3K inhibitor compound is administered to a patient (e.g., a human or animal subject) in need thereof to mediate (or modulate) PI3K activity.

The compounds of the preferred embodiment are useful in pharmaceutical compositions for human or veterinary use where inhibition of PI3K is indicated, for example, in the treatment of cellular proliferative diseases such as tumor and/or cancerous cell growth mediated by PI3K. In particular, the compounds are useful in the treatment of human or animal (e.g., murine) cancers, including, for example, lung and bronchus; prostate; breast; pancreas; colon and rectum; thyroid; liver and intrahepatic bile duct; hepatocellular; gastric; glioma/glioblastoma; endometrial; melanoma; kidney and renal pelvis; urinary bladder; uterine corpus; uterine cervix; ovary; multiple myeloma; esophagus; acute myelogenous leukemia; chronic myelogenous leukemia; lymphocytic leukemia; myeloid leukemia; brain; oral cavity and pharynx; larynx; small intestine; non-Hodgkin lymphoma; melanoma; and villous colon adenoma.

Agents of the invention, particularly those which have selectivity for pi3kinase gamma inhibition, are particularly useful in the treatment of inflammatory or obstructive airways diseases, resulting, for example, in reduction of tissue damage, airways inflammation, bronchial hyperreactivity, remodelling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other inflammatory or obstructive airways diseases and conditions to which the present invention is applicable include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Having regard to their anti-inflammatory activity, in particular in relation to inhibition of eosinophil activation, agents of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Agents of the invention are also useful in the treatment of inflammatory or allergic conditions of the skin, for example psoriasis, contact dermatitis, atopic dermatitis, alopecia greata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin.

Agents of the invention may also be used for the treatment of other diseases or conditions, in particular diseases or conditions having an inflammatory component, for example, treatment of diseases and conditions of the eye such as conjunctivitis, keratoconjunctivitis sicca, and vernal conjunctivitis, diseases affecting the nose including allergic rhinitis, and inflammatory disease in which autoimmune reactions are implicated or having an autoimmune component or aetiology, including autoimmune haematological disorders (e.g. haemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary billiary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy), thrombosis, hypertension, heart ischaemia and pancreatitis.

Another embodiment provides a method for inhibiting leucocytes, in particular neutrophils and B and T lymphocytes. Exemplary medical conditions that can be treated include those conditions characterized by an undesirable neutrophil function selected from the group consisting of stimulated superoxide release, stimulated exocytosis, and chemotactic migration, preferably without inhibiting phagocytic activity or bacterial killing by the neutrophils.

Another embodiment provides a method for disrupting the function of osteoclasts and ameliorating a bone resorption disorder, such as osteoporosis.

Another embodiment provides treatment of diseases or conditions with agents of the embodiments, such as, but not limited to septic shock, allograft rejection following transplantation, bone disorders such as but not limited to rheumatoid arthritis, ankylosing spondylitis osteoarthritis, obesity, restenosis, diabetes, e.g. diabetes mellitus type I (juvenile diabetes) and diabetes mellitus type II, diarrheal diseases.

In other embodiments, the PI3K-mediated condition or disorder is selected from the group consisting of: cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease, reperfusion injuries, retinopathy, such as diabetic retinopathy or hyperbaric oxygen-induced retinopathy, and conditions characterized by elevated intraocular pressure or secretion of ocular aqueous humor, such as glaucoma.

As described above, since PI3K serves as a second messenger node that integrates parallel signaling pathways, evidence is emerging that the combination of a PI3K inhibitor with inhibitors of other pathways will be useful in treating cancer and proliferative diseases in humans.

Approximately 20-30% of human breast cancers overexpress Her-2/neu-ErbB2, the target for the drug trastuzumab. Although trastuzumab has demonstrated durable responses in some patients expressing Her2/neu-ErbB2, only a subset of these patients respond. Recent work has indicated that this limited response rate can be substantially improved by the combination of trastuzumab with inhibitors of PI3K or the PI3K/AKT pathway (Chan et al., *Breast Can. Res. Treat.* 91:187 (2005), Woods Ignatoski et al., *Brit. J. Cancer* 82:666 (2000), Nagata et al., *Cancer Cell* 6:117 (2004)).

A variety of human malignancies express activitating mutations or increased levels of Her1/EGFR and a number of antibody and small molecule inhibitors have been developed against this receptor tyrosine kinase including tarceva, gefitinib and erbitux. However, while EGFR inhibitors demonstrate anti-tumor activity in certain human tumors (e.g., NSCLC), they fail to increase overall patient survival in all patients with EGFR-expressing tumors. This may be rationalized by the fact that many downstream targets of Her1/EGFR are mutated or deregulated at high frequencies in a variety of malignancies, including the PI3K/Akt pathway. For example, gefitinib inhibits the growth of an adenocarcinoma cell line in in vitro assays. Nonetheless, sub-clones of these cell lines can be selected that are resistant to gefitinib that demonstrate increased activation of the PI3/Akt pathway. Down-regulation or inhibition of this pathway renders the resistant sub-clones sensitive to gefitinib (Kokubo et al., Brit. J. Cancer 92:1711 (2005)). Furthermore, in an in vitro model of breast cancer with a cell line that harbors a PTEN mutation and over-expresses EGFR inhibition of both the PI3K/Akt pathway and EGFR produced a synergistic effect (She et al., Cancer Cell 8:287-297 (2005)). These results indicate that the combination of gefitinib and PI3K/Akt pathway inhibitors would be an attractive therapeutic strategy in cancer.

The combination of AEE778 (an inhibitor of Her-2/neu/ErbB2, VEGFR and EGFR) and RAD001 (an inhibitor of mTOR, a downstream target of Akt) produced greater combined efficacy that either agent alone in a glioblastoma xenograft model (Goudar et al., *Mol. Cancer. Ther.* 4:101-112 (2005)).

Anti-estrogens, such as tamoxifen, inhibit breast cancer growth through induction of cell cycle arrest that requires the action of the cell cycle inhibitor p27Kip. Recently, it has been shown that activation of the Ras-Raf-MAP Kinase pathway alters the phosphorylation status of p27Kip such that its inhibitory activity in arresting the cell cycle is attenuated, thereby contributing to anti-estrogen resistance (Donovan, et al, *J. Biol. Chem.* 276:40888, (2001)). As reported by Donovan et al., inhibition of MAPK signaling through treatment with MEK inhibitor reversed the aberrant phosphorylation status of p27 in hormone refractory breast cancer cell lines and in so doing restored hormone sensitivity. Similarly, phosphorylation of p27Kip by Akt also abrogates its role to arrest the cell cycle (Viglietto et al., *Nat. Med.* 8:1145 (2002)). Accordingly, in one aspect, the compounds as defined herein may be used in the treatment of hormone dependent cancers, such as breast and prostate cancers, to reverse hormone resistance commonly seen in these cancers with conventional anticancer agents.

In hematological cancers, such as chronic myelogenous leukemia (CML), chromosomal translocation is responsible for the constitutively activated BCR-Abl tyrosine kinase. The afflicted patients are responsive to imatinib, a small molecule tyrosine kinase inhibitor, as a result of inhibition of Abl kinase activity. However, many patients with advanced stage disease respond to imatinib initially, but then relapse later due to resistance-conferring mutations in the Abl kinase domain. In vitro studies have demonstrated that BCR-Ab1 employs the Ras-Raf kinase pathway to elicit its effects. In addition, inhibiting more than one kinase in the same pathway provides additional protection against resistance-conferring mutations. Accordingly, in another aspect of the embodiments, the compounds as defined herein are used in combination with at least one additional agent, such as Gleevec®, in the treatment of hematological cancers, such as chronic myelogenous leukemia (CML), to reverse or prevent resistance to at least one additional agent.

Because activation of the PI3K/Akt pathway drives cell survival, inhibition of the pathway in combination with therapies that drive apoptosis in cancer cells, including radiotherapy and chemotherapy, will result in improved responses (Ghobrial et al., CA *Cancer J. Clin* 55:178-194 (2005)). As an example, combination of PI3 kinase inhibitor with carboplatin demonstrated synergistic effects in both in vitro proliferation and apoptosis assays as well as in in vivo tumor efficacy in a xenograft model of ovarian cancer (Westfall and Skinner, *Mol. Cancer. Ther.* 4:1764-1771 (2005)).

In addition to cancer and proliferative diseases, there is accumulating evidence that inhibitors of Class 1A and 1B PI3 kinases would be therapeutically useful in others disease areas. The inhibition of p110β, the PI3K isoform product of the PIK3CB gene, has been shown to be involved in shear-induced platelet activation (Jackson et al., *Nature Medicine* 11:507-514 (2005)). Thus, a PI3K inhibitor that inhibits p110β would be useful as a single agent or in combination in anti-thrombotic therapy. The isoform p110β, the product of the PIK3CD gene, is important in B cell function and differentiation (Clayton et al., *J. Exp. Med.* 196:753-763 (2002)), T-cell dependent and independent antigen responses (Jou et al., *Mol. Cell. Biol.* 22:8580-8590 (2002)) and mast cell differentiation (Ali et al., *Nature* 431:1007-1011 (2004)). Thus, it is expected that p110β-inhibitors would be useful in the treatment of B-cell driven autoimmune diseases and asthma. Finally, the inhibition of p110β, the isoform product of the PI3KCG gene, results in reduced T, but not B cell, response (Reif et al., *J. Immunol.* 173:2236-2240 (2004)) and its inhibition demonstrates efficacy in animal models of autoimmune diseases (Camps et al., *Nature Medicine* 11:936-943 (2005), Barber et al., *Nature Medicine* 11:933-935 (2005)).

The preferred embodiments provide pharmaceutical compositions comprising at least one compound as defined herein together with a pharmaceutically acceptable carrier suitable for administration to a human or animal subject, either alone or together with other anticancer agents.

Another embodiment provides methods of treating human or animal subjects suffering from a cellular proliferative disease, such as cancer. The preferred embodiments provide methods of treating a human or animal subject in need of such treatment, comprising administering to the subject a therapeutically effective amount of a compound as defined herein, either alone or in combination with other anticancer agents.

In particular, compositions will either be formulated together as a combination therapeutic or administered separately. Anticancer agents for use with the preferred embodiments include, but are not limited to, one or more of the following set forth below:

A. Kinase Inhibitors

Kinase inhibitors for use as anticancer agents in conjunction with the compositions of the preferred embodiments include inhibitors of Epidermal Growth Factor Receptor (EGFR) kinases such as small molecule quinazolines, for example gefitinib (U.S. Pat. No. 5,457,105, U.S. Pat. No. 5,616,582, and U.S. Pat. No. 5,770,599), ZD-6474 (WO 01/32651), erlotinib (Tarceva®, U.S. Pat. No. 5,747,498 and WO 96/30347), and lapatinib (U.S. Pat. No. 6,727,256 and WO 02/02552); Vascular Endothelial Growth Factor Receptor (VEGFR) kinase inhibitors, including SU-11248 (WO 01/60814), SU 5416 (U.S. Pat. No. 5,883,113 and WO 99/61422), SU 6668 (U.S. Pat. No. 5,883,113 and WO 99/61422), CHIR-258 (U.S. Pat. No. 6,605,617 and U.S. Pat. No. 6,774,237), vatalanib or PTK-787 (U.S. Pat. No. 6,258,812), VEGF-Trap (WO 02/57423), B43-Genistein (WO-09606116), fenretinide (retinoic acid p-hydroxyphenylamine) (U.S. Pat. No. 4,323,581), IM-862 (WO 02/62826), bevacizumab or Avastin® (WO 94/10202), KRN-951, 3-[5-(methylsulfonylpiperadine methyl)-indolyl]-quinolone, AG-13736 and AG-13925, pyrrolo[2,1-f][1,2,4]triazines, ZK-304709, Veglin®, VMDA-3601, EG-004, CEP-701 (U.S. Pat. No. 5,621,100), C and 5 (WO 04/09769); Erb2 tyrosine kinase inhibitors such as pertuzumab (WO 01/00245), trastuzumab, and rituximab; Akt protein kinase inhibitors, such as RX-0201; Protein Kinase C(PKC) inhibitors, such as LY-317615 (WO 95/17182), and perifosine (US 2003171303); Raf/Map/MEK/Ras kinase inhibitors including sorafenib (BAY 43-9006), ARQ-350RP, LErafAON, BMS-354825 AMG-548, and others disclosed in WO 03/82272; Fibroblast Growth Factor Receptor (FGFR) kinase inhibitors; Cell Dependent Kinase (CDK) inhibitors, including CYC-202 or roscovitine (WO 97/20842 and WO 99/02162); Platelet-Derived Growth Factor Receptor (PDGFR) kinase inhibitors such as CHIR-258, 3G3 mAb, AG-13736, SU-11248 and SU6668; and Bcr-Abl kinase inhibitors and fusion proteins such as STI-571 or Gleevec® (imatinib).

B. Anti-Estrogens

Estrogen-targeting agents for use in anticancer therapy in conjunction with the compositions of the preferred embodiments include Selective Estrogen Receptor Modulators (SERMs) including tamoxifen, toremifene, raloxifene; aromatase inhibitors including Arimidex® or anastrozole; Estrogen Receptor Downregulators (ERDs) including Faslodex® or fulvestrant.

C. Anti-Androgens

Androgen-targeting agents for use in anticancer therapy in conjunction with the compositions of the preferred embodiments include flutamide, bicalutamide, finasteride, aminoglutethamide, ketoconazole, and corticosteroids.

D. Other Inhibitors

Other inhibitors for use as anticancer agents in conjunction with the compositions of the preferred embodiments include protein farnesyl transferase inhibitors including tipifarnib or R-115777 (US 2003134846 and WO 97/21701), BMS-214662, AZD-3409, and FTI-277; topoisomerase inhibitors including merbarone and diflomotecan (BN-80915); mitotic kinesin spindle protein (KSP) inhibitors including SB-743921 and MKI-833; proteasome modulators such as bortezomib or Velcade® (U.S. Pat. No. 5,780,454), XL-784; and cyclooxygenase 2 (COX-2) inhibitors including non-steroidal antiinflammatory drugs I (NSAIDs).

E. Cancer Chemotherapeutic Drugs

Particular cancer chemotherapeutic agents for use as anticancer agents in conjunction with the compositions of the preferred embodiments include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®, US 2004073044), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), *phoenix* (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

F. Alkylating Agents

Alkylating agents for use in conjunction with the compositions of the preferred embodiments for anticancer therapeutics include VNP-40101M or cloretizine, oxaliplatin (U.S. Pat. No. 4,169,846, WO 03/24978 and WO 03/04505), glufosfamide, mafosfamide, etopophos (U.S. Pat. No. 5,041,424), prednimustine; treosulfan; busulfan; irofluven (acylfulvene); penclomedine; pyrazoloacridine (PD-115934); O6-benzylguanine; decitabine (5-aza-2-deoxycytidine); brostallicin; mitomycin C (MitoExtra); TLK-286 (Telcyta®); temozolomide; trabectedin (U.S. Pat. No. 5,478,932); AP-5280 (Platinate formulation of Cisplatin); porfiromycin; and clearazide (meclorethamine).

G. Chelating Agents

Chelating agents for use in conjunction with the compositions of the preferred embodiments for anticancer therapeutics include tetrathiomolybdate (WO 01/60814); $R^P$-697; Chimeric T84.66 (cT84.66); gadofosveset (Vasovist®); deferoxamine; and bleomycin optionally in combination with electorporation (EPT).

H. Biological Response Modifiers

Biological response modifiers, such as immune modulators, for use in conjunction with the compositions of the preferred embodiments for anticancer therapeutics include staurosprine and macrocyclic analogs thereof, including UCN-01, CEP-701 and midostaurin (see WO 02/30941, WO 97/07081, WO 89/07105, U.S. Pat. No. 5,621,100, WO 93/07153, WO 01/04125, WO 02/30941, WO 93/08809, WO 94/06799, WO 00/27422, WO 96/13506 and WO 88/07045); squalamine (WO 01/79255); DA-9601 (WO 98/04541 and U.S. Pat. No. 6,025,387); alemtuzumab; interferons (e.g. IFN-α, IFN-b etc.); interleukins, specifically IL-2 or aldesleukin as well as IL-1, IL-3, IL-4, IL-5, IL-6, IL-7, IL-8, IL-9, IL-10, IL-11, IL-12, and active biological variants thereof having amino acid sequences greater than 70% of the native human sequence; altretamine (Hexylen®); SU 101 or leflunomide (WO 04/06834 and U.S. Pat. No. 6,331,555); imidazoquinolines such as resiquimod and imiquimod (U.S. Pat. Nos. 4,689,338, 5,389,640, 5,268,376, 4,929,624, 5,266,575, 5,352,784, 5,494,916, 5,482,936, 5,346,905, 5,395,937, 5,238,944, and 5,525,612); and SMIPs, including benzazoles, anthraquinones, thiosemicarbazones, and tryptanthrins (WO 04/87153, WO 04/64759, and WO 04/60308).

I. Cancer Vaccines:

Anticancer vaccines for use in conjunction with the compositions of the preferred embodiments include Avicine® (*Tetrahedron Lett.* 26:2269-70 (1974)); oregovomab (OvaRex®); Theratope® (STn-KLH); Melanoma Vaccines; G1-4000 series (G1-4014, G1-4015, and G1-4016), which are directed to five mutations in the Ras protein; GlioVax-1; MelaVax; Advexin® or INGN-201 (WO 95/12660); Sig/E7/LAMP-1, encoding HPV-16 E7; MAGE-3 Vaccine or M3TK (WO 94/05304); HER-2VAX; ACTIVE, which stimulates T-cells specific for tumors; GM-CSF cancer vaccine; and *Listeria monocytogenes*-based vaccines.

J. Antisense Therapy:

Anticancer agents for use in conjunction with the compositions of the preferred embodiments also include antisense compositions, such as AEG-35156 (GEM-640); AP-12009 and AP-11014 (TGF-beta2-specific antisense oligonucleotides); AVI-4126; AVI-4557; AVI-4472; oblimersen (Genasense®); JFS2; aprinocarsen (WO 97/29780); GTI-2040 (R2 ribonucleotide reductase mRNA antisense oligo) (WO 98/05769); GTI-2501 (WO 98/05769); liposome-encapsulated c-Raf antisense oligodeoxynucleotides (LErafAON) (WO 98/43095); and Sirna-027 (RNAi-based therapeutic targeting VEGFR-1 mRNA).

The compounds of the preferred embodiments can also be combined in a pharmaceutical composition with bronchiodilatory or antihistamine drugs substances. Such bronchiodilatory drugs include anticholinergic or antimuscarinic agents, in particular ipratropium bromide, oxitropium bromide, and tiotropium bromide, and β-2-adrenoreceptor agonists such as salbutamol, terbutaline, salmeterol and, especially, formoterol. Co-therapeutic antihistamine drug substances include cetirizine hydrochloride, clemastine fumarate, promethazine, loratadine, desloratadine diphenhydramine and fexofenadine hydrochloride.

The effectiveness of an agent of the invention in inhibiting inflammatory conditions, for example in inflammatory airways diseases, may be demonstrated in an animal model, e.g. a mouse or rat model, of airways inflammation or other inflammatory conditions, for example as described by Szarka et al, J. Immunol. Methods (1997) 202:49-57; Renzi et al, Am. Rev. Respir. Dis. (1993) 148:932-939; Tsuyuki et al., J. Clin. Invest. (1995) 96:2924-2931; and Cernadas et al (1999) Am. J. Respir. Cell Mol. Biol. 20:1-8.

The agents of the invention are also useful as co-therapeutic agents for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneously with or after the other drug substance. Accordingly the invention includes a combination of an agent of the invention as hereinbefore described with an anti-inflammatory, bronchodilatory or antihistamine drug substance, said agent of the invention and said drug substance being in the same or different pharmaceutical composition. Such anti-inflammatory drugs include steroids, in particular glucocorticosteroids such as budesonide, beclamethasone, fluticasone, ciclesonide or mometasone, LTB4 antagonists such as those described in U.S. Pat. No. 5,451,700, LTD4 antagonists such as montelukast and zafirlukast, dopamine receptor agonists such as cabergoline, bromocriptine, ropinirole and 4-hydroxy-7-[2-[[2-[[3-(2-phenylethoxy)propyl]-sulfonyl]ethyl]-amino]ethyl]-2(3H)-benzothiazolone and pharmaceutically acceptable salts thereof (the hydrochloride being Viozan®-AstraZeneca), and PDE4 inhibitors such as Ariflo® (GlaxoSmith Kline), Roflumilast (Byk Gulden), V-11294A (Napp), BAY19-8004 (Bayer), SCH-351591 (Schering-Plough), Arofylline (Almirall Prodesfarma) and PD189659 (Parke-Davis). Such bronchodilatory drugs include anticholinergic or antimuscarinic agents, in particular ipratropium bromide, oxitropium bromide and tiotropium bromide, and beta-2 adrenoceptor agonists such as salbutamol, terbutaline, salmeterol and, especially, formoterol and pharmaceutically acceptable salts thereof, and compounds (in free or salt or solvate form) of formula I of PCT International patent publication No. WO 00/75114, which document is incorporated herein by reference, preferably compounds of the Examples thereof, especially a compound of formula

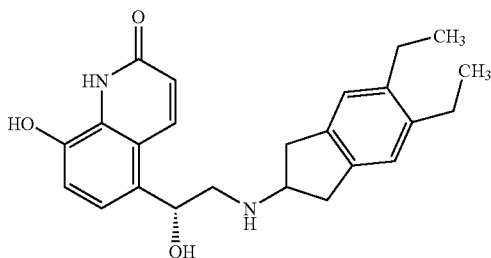

and pharmaceutically acceptable salts thereof. Co-therapeutic antihistamine drug substances include cetirizine hydrochloride, acetaminophen, clemastine fumarate, promethazine, loratidine, desloratidine, diphenhydramine and fexofenadine hydrochloride. Combinations of agents of the invention and steroids, beta-2 agonists, PDE4 inhibitors or LTD4 antagonists may be used, for example, in the treatment of COPD or, particularly, asthma. Combinations of agents of the invention and anticholinergic or antimuscarinic agents, PDE4 inhibitors, dopamine receptor agonists or LTB4 antagonists may be used, for example, in the treatment of asthma or, particularly, COPD.

Other useful combinations of agents of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzocyclohepten-8-yl]carbonyl]amino]phenyl]-methyl]tetrahydro-N,N-dimethyl-2H-pyran-4-aminium chloride (TAK-770), and CCR-5 antagonists described in U.S. Pat. No. 6,166,037 (particularly claims 18 and 19), WO 00/66558 (particularly claim 8), and WO 00/66559 (particularly claim 9).

The compounds of the preferred embodiments can also be combined in a pharmaceutical composition with compounds that are useful for the treatment of a thrombolytic disease, heart disease, stroke, etc., (e.g., aspirin, streptokinase, tissue plasminogen activator, urokinase, anticoagulants, antiplatelet drugs (e.g, PLAVIX; clopidogrel bisulfate), a statin (e.g., LIPITORor Atorvastatin calcium), ZOCOR (Simvastatin), CRESTOR (Rosuvastatin), etc.), a Beta blocker (e.g., Atenolol), NORVASC (amlodipine besylate), and an ACE inhibitor (e.g., lisinopril).

The compounds of the preferred embodiments can also be combined in a pharmaceutical composition with compounds that are useful for the treatment of antihypertension agents such as, ACE inhibitors, lipid lowering agents such as statins, LIPITOR (Atorvastatin calcium), calcium channel blockers dush as NORVASC (amlodipine besylate). The compounds of the preferred embodiments may also be used in combination with fibrates, beta-blockers, NEPI inhibitors, Angiotensin-2 receptor antagonists and platelet aggregation inhibitors.

For the treatment of inflammatory diseases, including rheumatoid arthritis, the compounds of the preferred embodiments may be combined with agents such as TNF-α inhibitors such as anti-TNF-α monoclonal antibodies (such as REMICADE, CDP-870) and D2E7 (HUMIRA) and TNF receptor immunoglobulin fusion molecules (such as ENBREL), IL-1 inhibitors, receptor antagonists or soluble IL-1R$^a$ (e.g. KINERET or ICE inhibitors), nonsterodial anti-inflammatory agents (NSAIDS), piroxicam, diclofenac, naproxen, flurbiprofen, fenoprofen, ketoprofen ibuprofen, fenamates, mefenamic acid, indomethacin, sulindac, apazone, pyrazolones, phenylbutazone, aspirin, COX-2 inhibitors (such as CELEBREX (celecoxib), PREXIGE (lumiracoxib)), metalloprotease inhibitors (preferably MMP-13 selective inhibitors), p2×7 inhibitors, α2α inhibitors, NEUROTIN, pregabalin, low dose methotrexate, leflunomide, hydroxyxchloroquine, d-penicillamine, auranofin or parenteral or oral gold.

The compounds of the preferred embodiments can also be used in combination with the existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flurbiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, lumiracoxib and etoricoxib, analgesics and intraarticular therapies such as corticosteroids and hyaluronic acids such as hyalgan and synvisc.

The compounds of the preferred embodiments may also be used in combination with antiviral agents such as Viracept, AZT, acyclovir and famciclovir, and antisepsis compounds such as Valant.

The compounds of the preferred embodiments may also be used in combination with CNS agents such as antidepressants (sertraline), anti-Parkinsonian drugs (such as deprenyl, L-dopa, Requip, Mirapex, MAOB inhibitors such as selegine and rasagiline, comP inhibitors, such as Tasmar, A-2 inhibitors, dopamine reuptake inhibitors, NMDA antagonists, Nicotine agonists, Dopamine agonists, and inhibitors of neuronal nitric oxide synthase), and anti-Alzheimer's drugs such as donepezil, tacrine, α2δinhibitors, NEUROTIN, pregabalin, COX-2 inhibitors, propentofylline or metrifonate.

The compounds of the preferred embodiments may also be used in combination with osteoporosis agents such as EVISTA (raloxifene hydrochloride), droloxifene, lasofoxifene or fosomax and immunosuppressant agents such as FK-506 and rapamycin.

In another aspect of the preferred embodiments, kits that include one or more compounds of the preferred embodiments are provided. Representative kits include a PI3K inhibitor compound of the preferred embodiments (e.g., a compound as defined herein) and a package insert or other labeling including directions for treating a cellular proliferative disease by administering a PI3K inhibitory amount of the compound.

Administration and Pharmaceutical Composition

In general, the compounds of preferred embodiments will be administered in a therapeutically effective amount by any of the accepted modes of administration for agents that serve similar utilities. The actual amount of the compound of preferred embodiments, i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day. All of these factors are within the skill of the attending clinician.

Therapeutically effective amounts of compounds as defined herein may range from about 0.05 to about 50 mg per kilogram body weight of the recipient per day; preferably about 0.1-25 mg/kg/day, more preferably from about 0.5 to 10 mg/kg/day. Thus, for administration to a 70 kg person, the dosage range would most preferably be about 35-70 mg per day.

In general, compounds of the preferred embodiments will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of the preferred embodiments is inhalation. This is an effective method for delivering a therapeutic agent directly to the respiratory tract (see U.S. Pat. No. 5,607,915).

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory airstream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound as defined herein in combination with at least one pharmaceutically acceptable excipient. Acceptable excipients are non-toxic, aid administration, and do not adversely affect the therapeutic benefit of the compound as defined herein. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of the preferred embodiments in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the compound in a formulation can vary within the full range employed by those skilled in the art. Typically, the formulation will contain, on a weight percent (wt %) basis, from about 0.01-99.99 wt % of a compound as defined herein based on the total formulation, with the balance being one or more suitable pharmaceutical excipients. Preferably, the compound is present at a level of about 1-80 wt %.

General Synthetic Methods

The compounds of preferred embodiments can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, New York, 1999, and references cited therein.

Furthermore, the compounds of preferred embodiments contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of the preferred embodiments, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chem or Sigma (St. Louis, Mo., USA). Others may be prepared by procedures, or obvious modifications thereof, described in standard reference texts such as Fieser and Fieser's *Reagents for Organic Synthesis*, Volumes 1-15 (John Wiley and Sons, 1991), Rodd's *Chemistry of Carbon Compounds*, Volumes 1-5 and Supplementals (Elsevier Science Publishers, 1989), *Organic Reactions*, Volumes 1-40 (John Wiley and Sons, 1991), March's *Advanced Organic Chemistry*, (John Wiley and Sons, 4th Edition), and Larock's *Comprehensive Organic Transformations* (VCH Publishers Inc., 1989).

The various starting materials, intermediates, and compounds of the preferred embodiments may be isolated and purified where appropriate using conventional techniques such as precipitation, filtration, crystallization, evaporation, distillation, and chromatography. Characterization of these compounds may be performed using conventional methods such as by melting point, mass spectrum, nuclear magnetic resonance, and various other spectroscopic analyses.

Compounds of preferred embodiments can be made by employing palladium mediated coupling reactions, such as Suzuki coupling. Said couplings can be employed to functionalize a heterocycle or aryl ring system at each position of the ring system providing said ring is suitably activated or functionalized.

Suzuki coupling (Suzuki et al., *Chem. Commun.* (1979) 866) can be used to form the final product and can be effected under known conditions such as by treatment with functionalized boronic esters as in the following schemes:

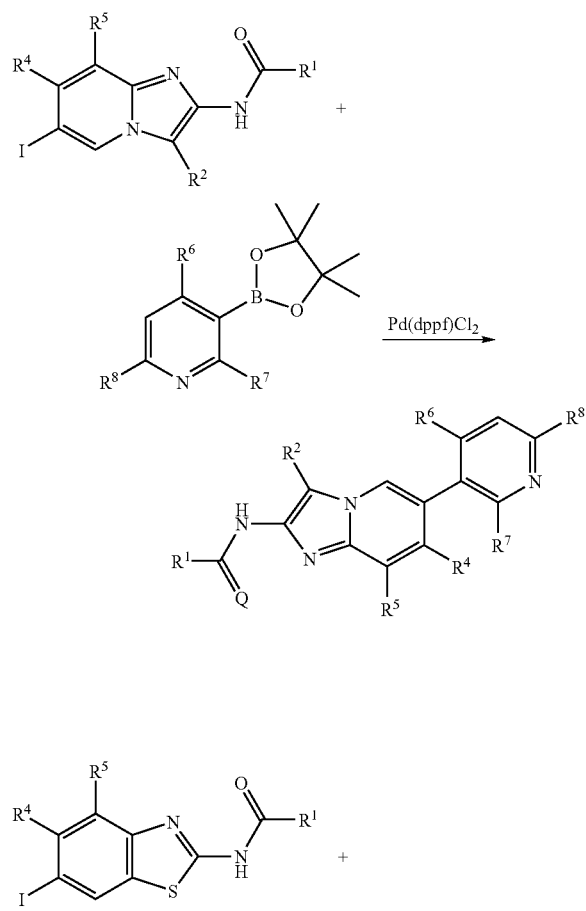

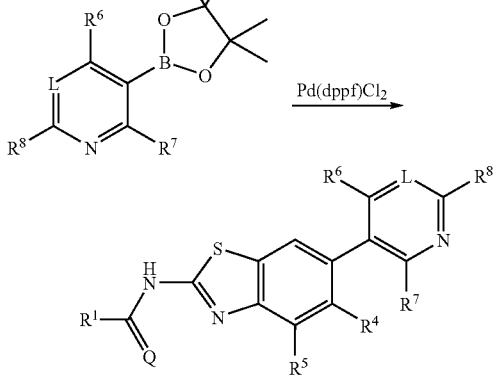

The pyridinyl or pyrimidinyl cores can be obtained commercially and functionalized. The pyridinyl or pyrimidinyl cores can comprise substituents that can be converted to desired functional groups. The pyridinyl or pyrimidinyl cores can comprise substituents with protecting groups, which can be removed in an appropriate setting. A scheme for an embodiment is shown below.

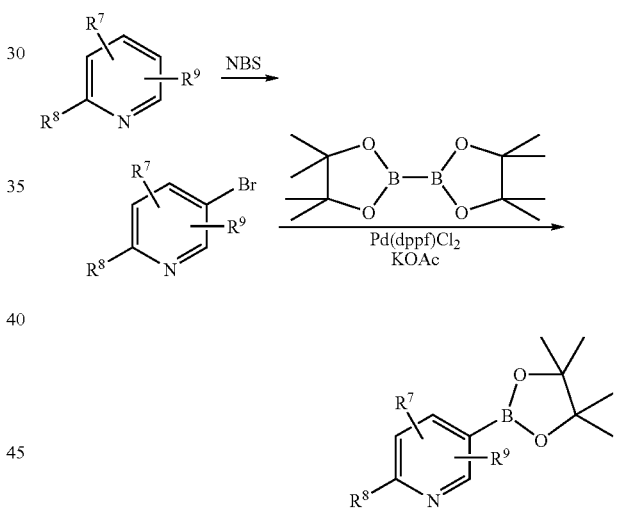

As shown above, methods for preparing compounds as defined herein are provided. For compounds of Formula II, the methods include reacting a halo-imidazopyridine with a pyridinyl or pyrimidinyl group containing a reactive boronic ester substituent, in the presence of a palladium catalyst. For compounds of Formula III, the methods include reacting a halo-benzothiazole with a pyridinyl or pyrimidinyl group containing a reactive boronic ester substituent, in the presence of a palladium catalyst.

In an embodiment, the palladium catalyst is palladium dichloride. In an embodiment, the palladium catalyst is dichloro(1,1-bis(diphenylphosphino)ferrocene) palladium (II)-dichloromethane adduct (Pd(dppf)Cl$_2$-DCM).

Accordingly, in one embodiment the preferred embodiments provides a method for synthesizing a compound, stereoisomer, tautomer, or a pharmaceutically acceptable salt of Formula II,

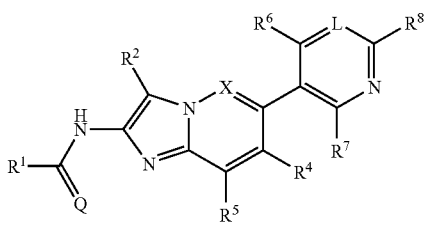

wherein the method comprises coupling a compound having the formula:

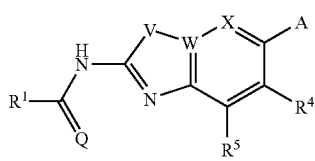

with a compound having the formula:

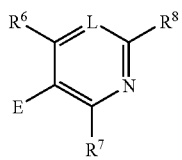

in the presence of a catalyst;
wherein:
A is halo
E is a boronic ester or boronic acid;
Q is O or S;
X is CR$^3$ or N;
L is CR$^9$ or N;
R$^1$ is selected from the group consisting of hydrogen, alkyl, substituted alkyl, alkenyl, substituted alkenyl, alkynyl, substituted alkynyl, alkoxy, substituted alkoxy, amino, substituted amino, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, and alkylamino;
R$^2$ and R$^3$ are independently selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, SO$_3$H, sulfonyl, substituted sulfonyl, sulfonyloxy, thioacyl, thiol, alkylthio, and substituted alkylthio;
R$^4$ and R$^5$ are independently selected from the group consisting of hydrogen, halogen, cyano, nitro, amino, substituted amino, alkoxy, substituted alkoxy, alkyl, and substituted alkyl;
R$^6$ is selected from the group consisting of hydrogen, halogen, cyano, nitro, alkoxy, substituted alkoxy, alkyl, and substituted alkyl;
R$^7$ and R$^9$ are independently selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acyloxy, aminocarbonyl, aminothiocarbonyl, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, SO$_3$H, sulfonyl, substituted sulfonyl, sulfonyloxy, thioacyl, thiol, alkylthio, and substituted alkylthio;
R$^8$ is selected from the group consisting of hydrogen, alkyl, —CO—R$^8$a, substituted alkyl, and a three- to seven-membered ring selected from the group consisting of cycloalkyl, substituted cycloalkyl, heterocyclyl, and substituted heterocyclyl; and
R$^{8a}$ is selected from the group consisting of alkyl, substituted alkyl, alkoxy, substituted alkoxy, amino, substituted amino, and alkylamino.

Accordingly, in one embodiment the preferred embodiments provides a method for synthesizing a compound, stereoisomer, tautomer, or a pharmaceutically acceptable salt of Formula III,

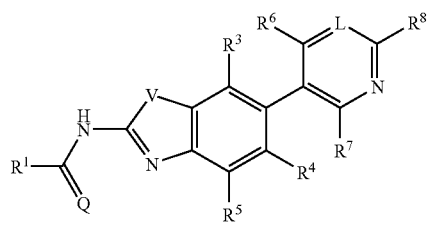

wherein the method comprises coupling a compound having the formula:

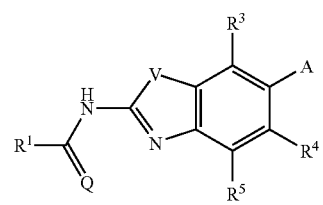

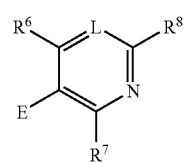

in the presence of a catalyst;

wherein:
A is halo
E is a boronic ester or boronic acid;
Q is O or S;
V is O or S;
L is CR$^9$ or N;
R$^1$ is selected from the group consisting of hydrogen, alkyl, substituted alkyl, alkenyl, substituted alkenyl, alkynyl, substituted alkynyl, alkoxy, substituted alkoxy, amino, substituted amino, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, and alkylamino;
R$^3$ is selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, SO$_3$H, sulfonyl, substituted sulfonyl, sulfonyloxy, thioacyl, thiol, alkylthio, and substituted alkylthio;
R$^4$ and R$^5$ are independently selected from the group consisting of hydrogen, halogen, cyano, nitro, amino, substituted amino, alkoxy, substituted alkoxy, alkyl, and substituted alkyl;
R$^6$ is selected from the group consisting of hydrogen, halogen, cyano, nitro, alkoxy, substituted alkoxy, alkyl, and substituted alkyl;
R$^7$ and R$^9$ are independently selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acyloxy, aminocarbonyl, aminothiocarbonyl, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, SO$_3$H, sulfonyl, substituted sulfonyl, sulfonyloxy, thioacyl, thiol, alkylthio, and substituted alkylthio;
R$^8$ is selected from the group consisting of hydrogen, alkyl, —CO—R$^{8a}$, substituted alkyl, and a three- to seven-membered ring selected from the group consisting of cycloalkyl, substituted cycloalkyl, heterocyclyl, and substituted heterocyclyl; and
R$^{8a}$ is selected from the group consisting of alkyl, substituted alkyl, alkoxy, substituted alkoxy, amino, substituted amino, and alkylamino.

More particular syntheses of compounds of the preferred embodiments, particularly those of Formulas I, II, and III, are provided in the following Methods and Examples:

The compounds of the invention, particularly compounds of formula (A) and formula (IV) may be prepared from compounds of formula (VI)

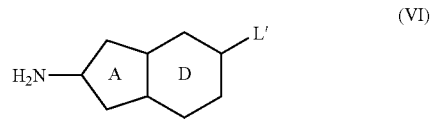

where L' is a halogen or other suitable leaving group followed by derivatisation of the amino group and Suzuki coupling as previously described.

Compounds of formula (VI) which are represented by compounds of formula (VII)

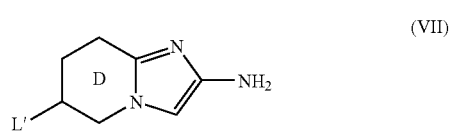

may be prepared by methods known or obvious to those skilled in the art, for example according to the following Scheme where L' is represented by Br.

Scheme

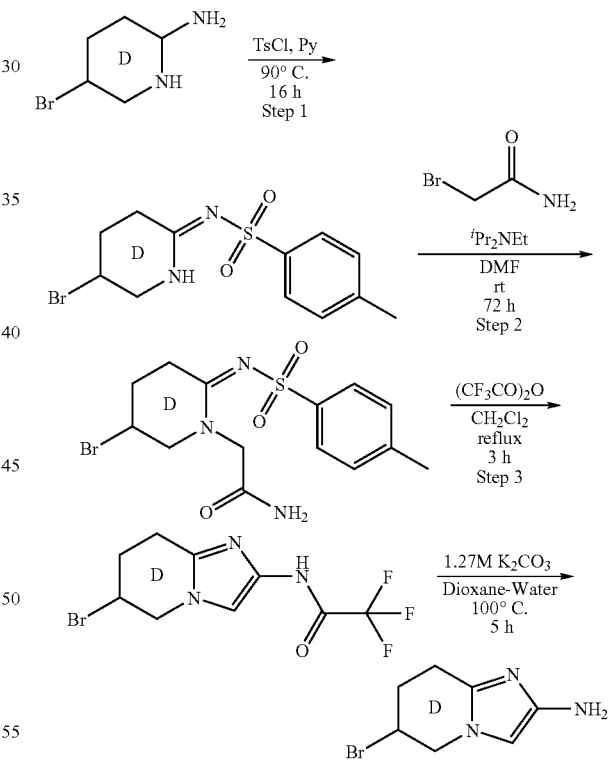

Compounds of formula (VI) which are represented by compounds of formula (VIII) or VIIIa

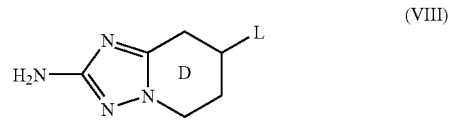

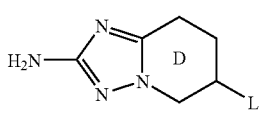

(VIIIa)

may be prepared by methods known or obvious to those skilled in the art, for example according to the following Scheme where L represents Br, e.g. as described in WO2006038116, Scheme

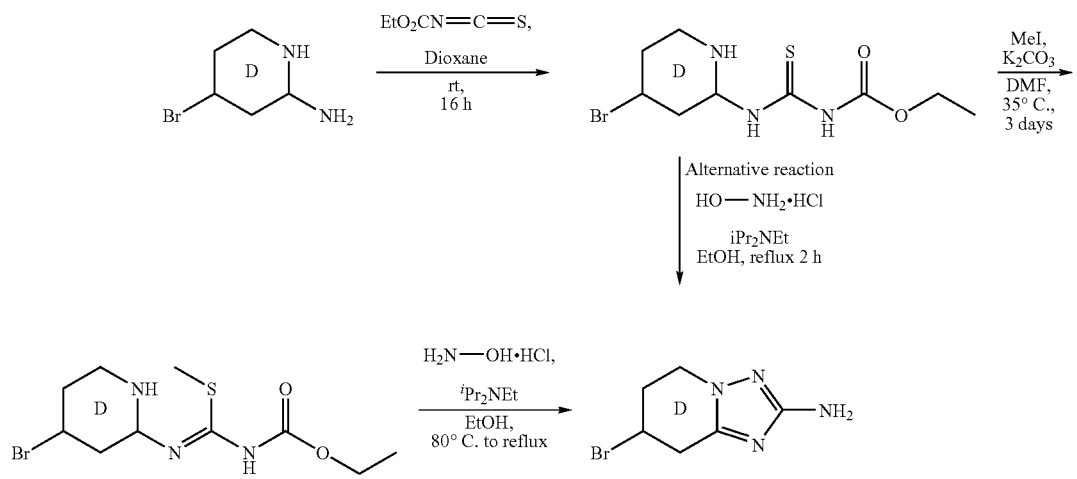

Compounds of formula VI-VIII may be further substituted and derviatised at the nitrogen group to prepare compounds of the invention by methods well-known to those skilled in the art. For example, compounds of formula IV where $R^1$ is Z—Y—$R^{10}$ and the preferred groups thereof, may be prepared according to the analogous methods described in WO05/021519.

EXAMPLES

Referring to the examples that follow, compounds of the preferred embodiments were synthesized using the methods described herein, or other methods, which are known in the art.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

It is understood that the invention is not limited to the embodiments set forth herein for illustration, but embraces all such forms thereof as come within the scope of the above disclosure.

The examples below as well as throughout the application, the following abbreviations have the following meanings. If not defined, the terms have their generally accepted meanings.

| Abbreviations | |
|---|---|
| ACN | acetonitrile |
| CDI | 1,1'-carbonyldiimidazole |
| DCM | dichloromethane |
| DIEA | diisopropylethylamine |
| DME | 1,2-dimethoxyethane |
| DMF | dimethylformamide |
| DMF-DMA | dimethylformamide dimethylacetal |
| DMSO | dimethyl sufoxide |

-continued

| Abbreviations | |
|---|---|
| DPPF | 1,1'-bis(diphenylphosphino)ferrocene |
| EDCI | 1-(3-dimethylaminopropyl)-3-ethylcarbodiimide hydrochloride |
| EtOAc | ethyl acetate |
| EtOH | ethanol |
| HATU | 2-(7-aza-1H)-benzotrizole-1-yl-1,1,3,3-tetramethylisouronium hexafluorophosphate |
| MeOH | methanol |
| NBS | N-bromosuccinimide |
| NCS | N-chlorosuccinimide |
| NMP | N-methyl-2-pyrrolidone |
| RT | room temperature |
| TEA | triethylamine |
| THF | tetrahydrofuran |
| TFA | trifluoroacetate |

Example compounds of formula X

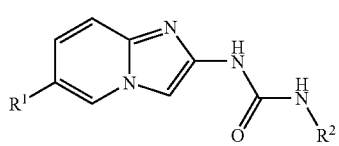

X are shown in Table 2 below. The Examples are in free form.

TABLE 2

| Ex. | R¹ | R² | M/s MH+ | Ki μM γ |
|---|---|---|---|---|
| 1-1 | 3-pyridyl | propyl-tetrazole-N-isopropyl | 392.21 | 0.058 |
| 1-2 | 4-pyridyl | propyl-tetrazole-N-isopropyl | 392.18 | 0.135 |
| 1-3 | 5-cyano-3-pyridyl | propyl-tetrazole-N-isopropyl | 417.21 | 0.04 |
| 1-4 | 5-pyrimidinyl | propyl-tetrazole-N-isopropyl | 393.19 | 0.165 |
| 1-5 | 3-pyridyl | propyl-tetrazole-N-ethyl | 377.76 | 0.08 |
| 1-6 | 5-ethoxy-3-pyridyl | propyl-tetrazole-N-isopropyl | 436.27 | 0.048 |
| 1-7 | 5-trifluoromethyl-3-pyridyl | propyl-tetrazole-N-isopropyl | 460.15 | 0.018 |
| 1-8 | 1,3-benzodioxol-5-yl | propyl-tetrazole-N-ethyl | 420.64 | 0.303 |
| 1-9 | 3-trifluoromethylphenyl | propyl-tetrazole-N-ethyl | 445.21 | 0.24 |

TABLE 2-continued

| Ex. | R¹ | R² | M/s MH+ | Ki μM γ |
|---|---|---|---|---|
| 1-10 | morpholine-C(O)-(5-methylpyridin-3-yl) | propyl-tetrazole-N-ethyl | 491.24 | 0.083 |
| 1-11 | 3-methylpyridine | butanamide-N-C(CH₃)₂CH₃ | 381.18 | 0.121 |
| 1-12 | 3-chloro-5-methylpyridine | propyl-tetrazole-N-isopropyl | 426.24 & 428.24 | 0.05 |
| 1-13 | tetrahydropyran-4-yloxy-5-methylpyridine | propyl-tetrazole-N-isopropyl | 492.29 | 0.147 |
| 1-14 | 3-methoxy-5-chloro-methylphenyl | propyl-tetrazole-N-ethyl | 441.27 & 443.27 | 0.204 |
| 1-15 | 3-phenyl-5-methylpyridine | butanamide-N-C(CH₃)₂CH₃ | 457.28 | 0.207 |
| 1-16 | 3-phenyl-5-methylpyridine | propyl-tetrazole-N-isopropyl | 468.20 | 0.24 |
| 1-17 | 5-methylpyridin-3-yloxy-ethoxy-ethoxy-methyl | propyl-tetrazole-N-isopropyl | 510.30 | 0.268 |

TABLE 2-continued

| Ex. | R¹ | R² | M/s MH+ | Ki μM γ |
|---|---|---|---|---|
| 1-18 | tetrahydropyran-4-yloxy-5-methylpyridine | butanamide N-tert-butyl | 481.29 | 0.397 |
| 1-19 | 2-methoxy-5-methylpyridine | 5-propyl-2-isopropyl-tetrazole | 422.27 | 0.301 |
| 1-20 | 2-methoxy-5-methylpyridine | 5-propyl-2-(2-fluoroethyl)-tetrazole | 426.17 | 0.075 |
| 1-21 | 3-methyl-5-(trifluoromethyl)pyridine | 5-propyl-2-ethyl-tetrazole | 432.17 | 0.014 |
| 1-22 | 3-methyl-5-ethylpyridine | 5-propyl-2-isopropyl-tetrazole | 420.15 | 0.025 |
| 1-23 | 3-methyl-5-(trifluoromethyl)pyridine | 4-propyl-1-ethyl-imidazole | 444.22 | 0.028 |
| 1-24 | 2-methyl-5-methylpyridine | 5-propyl-2-isopropyl-tetrazole | 406.20 | 0.113 |
| 1-25 | 3-methyl-5-(trifluoromethyl)pyridine | 1-propyl-5-ethyl-tetrazole | 445.96 | 0.026 |
| 1-26 | 3-methyl-5-cyanopyridine | 1-propyl-5-ethyl-tetrazole | 403.23 | 0.115 |

TABLE 2-continued
| Ex. | R¹ | R² | M/s MH+ | Ki μM γ |
|---|---|---|---|---|
| 1-27 | 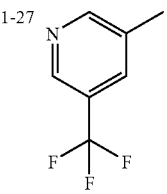 | 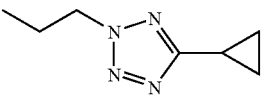 | 457.87 | 0.028 |
| 1-28 | 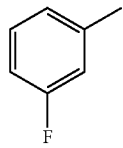 | 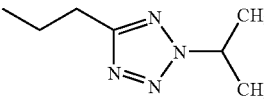 | 409.25 | 0.836 |
| 1-29 | 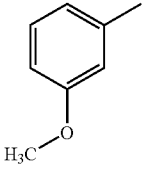 | 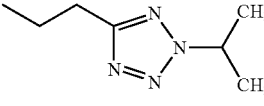 | 421.27 | 1.031 |
| 1-30 | 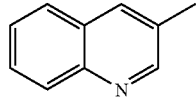 | 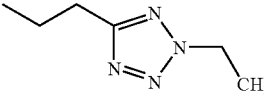 | 428.25 | 0.57 |
| 1-31 | 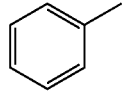 | 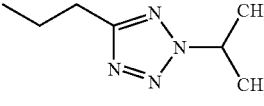 | 391.24 | 0.423 |
| 1-32 | 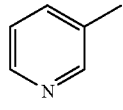 | 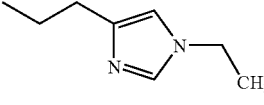 | 376.19 | 0.081 |
| 1-33 | 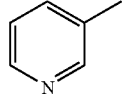 | 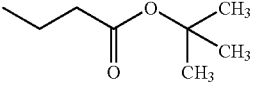 | 382.25 | 0.043 |
| 1-34 | 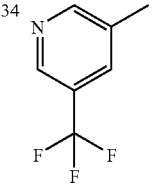 | 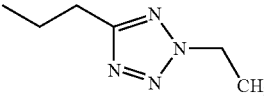 | 446.18 | 0.007 |
| 1-35 | 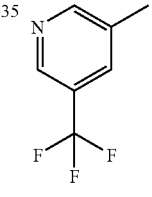 | 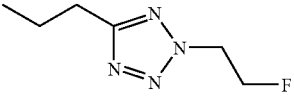 | 464.22 | 0.002 |
| 1-36 | 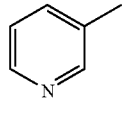 | 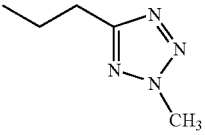 | 364.10 | 0.277 |

TABLE 2-continued

| Ex. | R¹ | R² | M/s MH+ | Ki μM γ |
|---|---|---|---|---|
| 1-37 | 3-methylpyridine | propyl-1-methyltetrazole | 364.1 | 0.584 |
| 1-38 | 3-methyl-5-(trifluoromethyl)pyridine | propyl-2-methyltetrazole | 432.1 | 0.012 |
| 1-39 | 2-methylphenyl-5-methylpyridine | propyl-2-isopropyltetrazole | 482.3 | 1.122 |
| 1-40 | 1,4-dimethylpyrazole | propyl-2-ethyltetrazole | 380.71 | 0.456 |
| 1-41 | 1-benzyl-4-methylpyrazole | propyl-2-ethyltetrazole | 456.64 | 0.735 |
| 1-42 | 4-methylisoquinoline | propyl-2-ethyltetrazole | 428.42 | 0.158 |
| 1-43 | 3-acetyl-5-methylpyridine | propyl-2-isopropyltetrazole | 434.25 | 0.008 |
| 1-44 | 3-methylpyridine | 1-propyl-5-ethyltetrazole | 378.19 | 0.177 |
| 1-45 | Br | propyl-2-ethyltetrazole | 379.11 | 0.911 |
| 1-46 | Br | butyl ketone-5-trifluoromethylisoxazole | 407.03 | 4.98 |

TABLE 2-continued

| Ex. | R¹ | R² | M/s MH+ | Ki µM γ |
|---|---|---|---|---|
| 1-47 | 5-methyl-pyridin-3-yl-sulfonyl(methyl) (3-methylsulfonyl-5-methyl-pyridine with methylsulfonyl group: pyridine ring with CH₃ and S(=O)₂CH₃) | propyl-tetrazole-N-CH(CH₃)₂ (isopropyl) | 470.88 | 0.014 |
| 1-48 | 3-fluoro-5-methyl-pyridine | propyl-tetrazole-N-CH(CH₃)₂ (isopropyl) | 410.80 | 0.168 |
| 1-49 | 3-methyl-quinoline | propyl-tetrazole-N-CH₂CH₃ (ethyl) | 428.25 | 0.570 |

Further example compounds of the present invention include compounds of formula (XI) and are as shown in Table 3 below. The methods of preparation being described hereinafter

TABLE 3

XI benzothiazol-2-yl (with R¹ at 6-position) —NH—C(=O)—NH—R²

| Ex. | R¹ | R² | M/z MH+ | Ki µM γ |
|---|---|---|---|---|
| 2-1 | 3-methyl-pyridin-5-yl | propyl-tetrazole-N-CH₂CH₂F | 413.20 | 0.008 |
| 2-2 | 6-methoxy-5-methyl-pyridin-3-yl | propyl-tetrazole-N-CH₂CH₂F | 443.11 | 0.02 |
| 2-3 | 6-methoxy-5-methyl-pyridin-3-yl | —CH₂CH₂CH₂—N(CH₃)₂ | 371.08 | 0.038 |
| 2-4 | 6-methoxy-5-methyl-pyridin-3-yl | —CH₂CH₂CH₂—OH | 345.04 | 0.038 |
| 2-5 | 6-methoxy-5-methyl-pyridin-3-yl | —CH₂—(pyridin-3-yl) | 392.12 | 0.149 |
| 2-6 | 6-methoxy-5-methyl-pyridin-3-yl | —CH₂CH₂CH₃ | 329.25 | 0.406 |

TABLE 3-continued
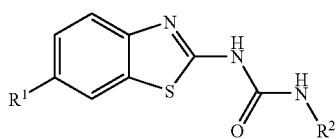
| Ex. | R¹ | R² | M/z MH+ | Ki μM γ |
|---|---|---|---|---|
| 2-7 | (5-pyridyl with methyl and morpholine carbonyl) | (propyl-tetrazole-N-CH2CH2F) | 526.20 | 0.0055 |
| 2-8 | (5-pyridyl with CF3) | (propyl-tetrazole-N-CH2CH2F) | 481.10 | 0.016 |
| 2-9 | (5-pyridyl with CF3) | (propyl-tetrazole-N-CH2CH3) | 463.18 | 0.06 |
| 2-10 | (5-pyridyl with CF3) | (propyl-tetrazole-N-CH(CH3)2) | 477.16 | 0.092 |
| 2-11 | (5-pyridyl with CF3) | (propyl-N-tetrazole-5-ethyl) | 463.14 | 0.242 |
| 2-12 | (5-pyridyl with CF3) | (propyl-imidazole-N-ethyl) | 461.17 | 0.142 |

Further example compounds of the present invention are as shown in Table 4 below. The methods of preparation being described thereinafter.

TABLE 4

| Ex. | Chemical Structure | Chemical name | M/s MH+ | Ki µM γ |
|---|---|---|---|---|
| 3-1 | 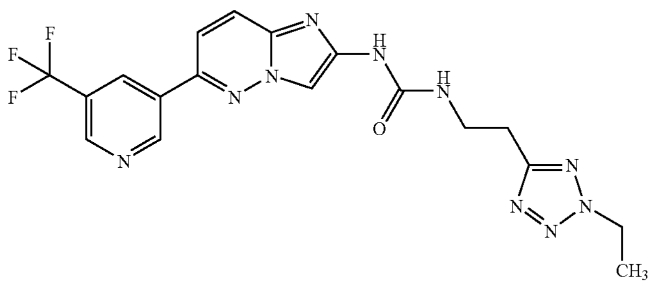 | 1-[2-(2H-Ethyl-2H-tetrazole-5-yl)-ethyl]-3-[6-(5-trifluoromethyl-pyridin-3-yl)-imidazo[1,2-b]pyridazin-2-yl]-urea | 446.86 | 0.012 |
| 3-2 | 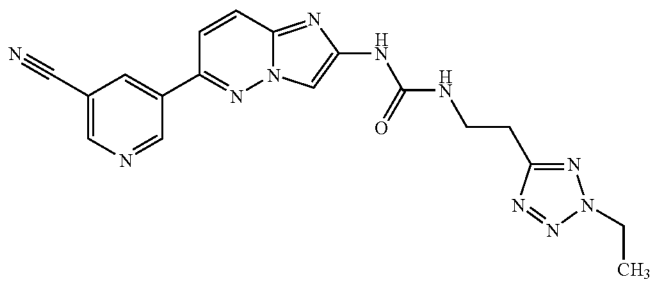 | 1-[6-(5-Cyano-pyridin-3-yl)-imidazo[1,2-b]pyridazin-2-yl]-3-[2-(2-ethyl-2H-tetrazol-5-yl)-ethyl]-urea | 403.41 | 0.031 |
| 3-3 | 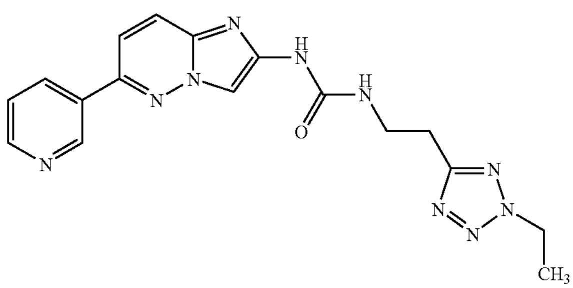 | 1-[6-(pyridin-3-yl)-imidazo[1,2-b]pyridazin-2-yl]-3-[2-(2-ethyl-2H-tetrazol-5-yl)-ethyl]-urea | 378.92 | 0.031 |
| 3-4 | 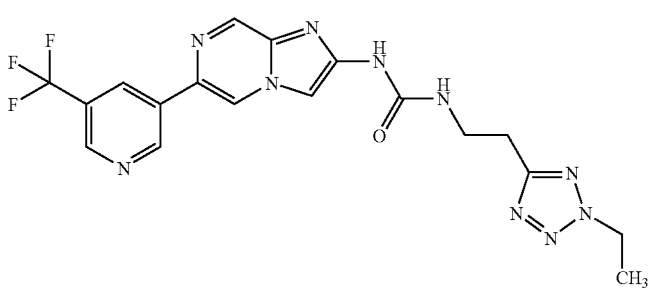 | 1-[2-(2-Ethyl-2H-tetrazol-5-yl)-ethyl]-3-[6-(5-trifluoromethyl-pyridin-3-yl)-imidazo[1,2-a]pyrazin-2-yl]-urea | 447.27 | 0.027 |
| 3-5 | 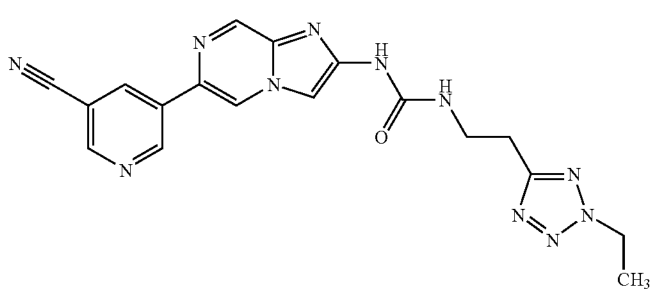 | 1-[6-(5-Cyano-pyridin-3-yl)-imidazo[1,2-a]pyrazin-2-yl]-3-[2-(2-ethyl-2H-tetrazol-5-yl)-ethyl]-urea | 404.23 | 0.098 |

TABLE 4-continued

| Ex. | Chemical Structure | Chemical name | M/s MH+ | Ki μM γ |
|---|---|---|---|---|
| 3-6 | 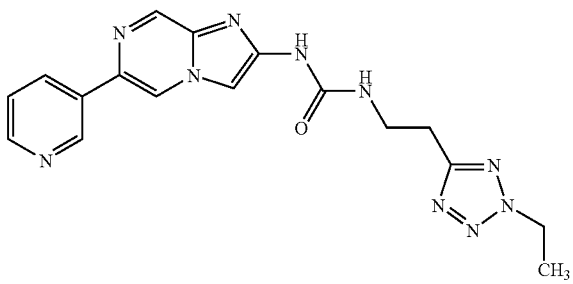 | 1-[2-(2-Ethyl-2H-tetrazol-5-yl)-ethyl]-3-(6-pyridin-3-yl-imidazo[1,2-a]pyrazin-2-yl)-urea | 379.33 | 0.082 |
| 3-7 | 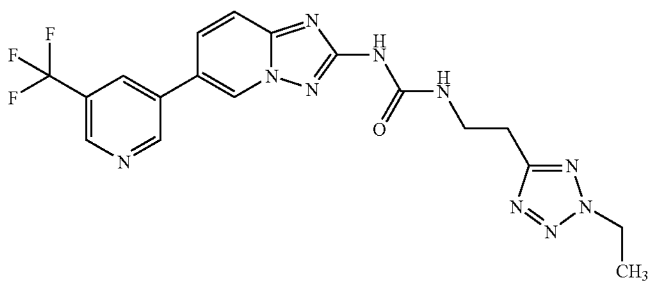 | 1-[2-(2-Ethyl-2H-tetrazol-5-yl)-ethyl]-3-[6-(5-trifluoromethyl-pyridin-3-yl)-[1,2,4]triazolo[1,5-a]pyridin-2-yl]-urea | 447.17 | 0.376 |
| 3-8 | 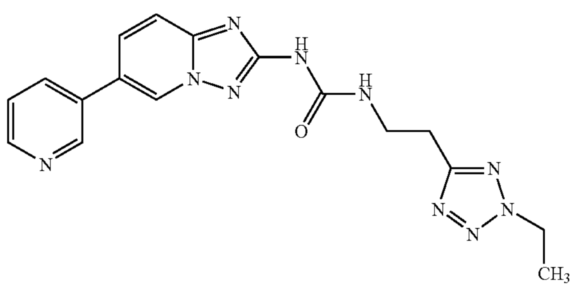 | 1-[2-(2-Ethyl-2H-tetrazol-5-yl)-ethyl]-3-(6-pyridin-3-yl-[1,2,4]triazolo[1,5-a]pyridin-2-yl)-urea | 378.16 | 0.099 |
| 3-9 | 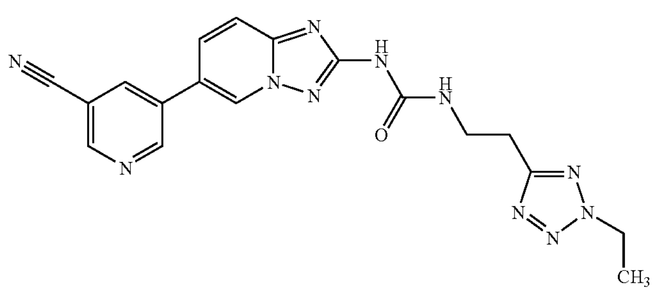 | 1-[6-(5-Cyano-pyridin-3-yl)-[1,2,4]triazolo[1,5-a]pyridin-2-yl]-3-[2-(2-ethyl-2H-tetrazol-5-yl)-ethyl]-urea | 404.74 | 0.418 |
| 3-10 | 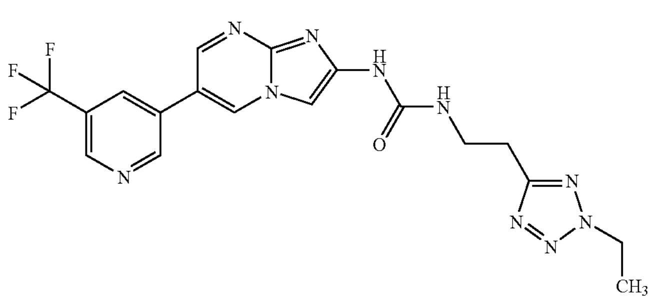 | 1-[2-(2-Ethyl-2H-tetrazol-5-yl)-ethyl]-3-[6-(5-trifluoromethyl-pyridin-3-yl)-imidazo[1,2-a]pyrimnidin-2-yl)-urea | 447.80 | 0.884 |

TABLE 4-continued

| Ex. | Chemical Structure | Chemical name | M/s MH+ | Ki μM γ |
|---|---|---|---|---|
| 3-11 | 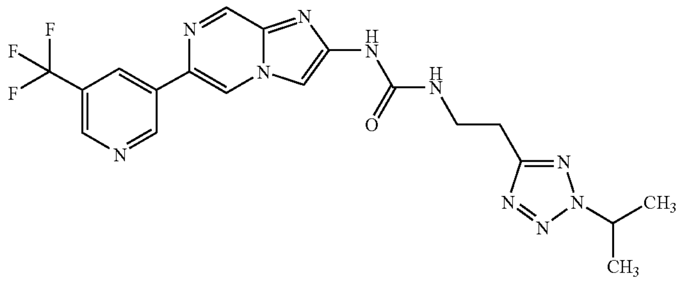 | 1-[2-(2-Isopropyl-2H-tetrazol-5-yl)-ethyl]-3-[6-(5-trifluoromethyl-pyridin-3-yl)-imidazo[1,2-a]pyrazin-2-yl]-urea | 461.81 | |
| 3-12 | 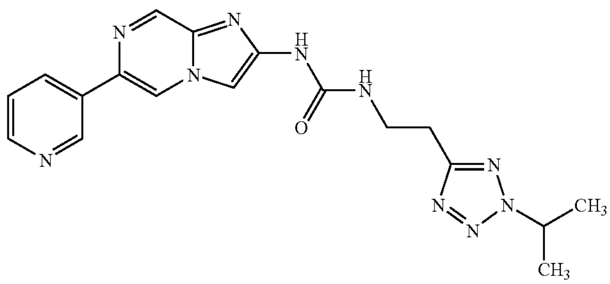 | 1-[2-(2-Isopropyl-2H-tetrazol-5-yl)-ethyl]-3-(6-pyridin-3-yl-imidazo[1,2-a]pyrazin-2-yl)-urea | 393.76 | |
| 3-13 | 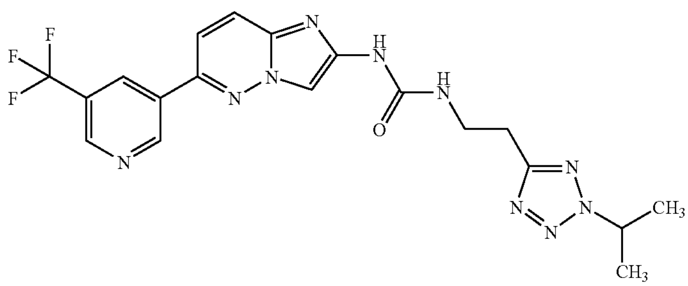 | 1-[2-(2-Isopropyl-2H-tetrazol-5-yl)ethyl]-3-[6-(5-trifluoromethyl-pyridin-3-yl)-imidazo[1,2-b]pyridazin-2-yl]-urea | 460.38 | |
| 3-14 | 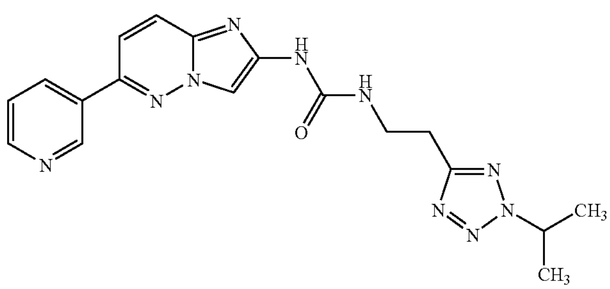 | 1-[2-(2-Isopropyl-2H-tetrazol-5-yl)-ethyl]-3-(6-pyridin-3-yl-imidazo[1,2-b]pyridazin-2-yl)-urea | 393.16 | |
| 3-15 | 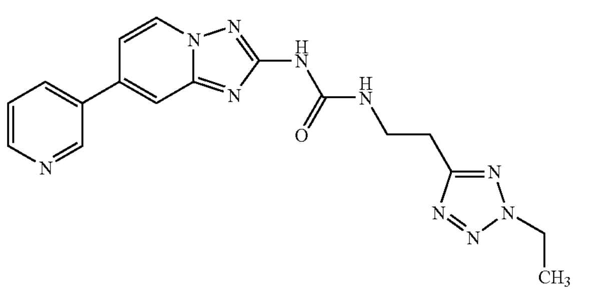 | 1-[2-(2-Ethyl-2H-tetrazol-5-yl)-ethyl]-3-(7-pyridin-3-yl-[1,2,4]triazolo[1,5-a]pyridin-2-yl)-urea | 379.20 | 0.502 |

TABLE 4-continued

| Ex. | Chemical Structure | Chemical name | M/s MH+ | Ki μM γ |
|---|---|---|---|---|
| 3-16 | 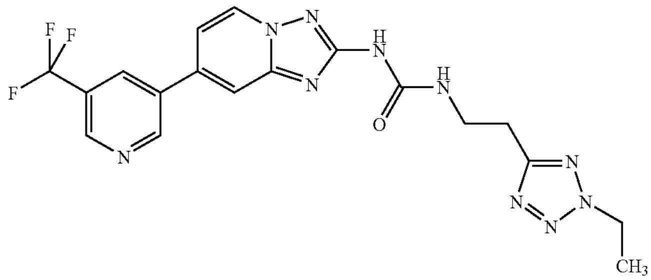 | 1-[2-(2-Ethyl-2H-tetrazol-5-yl)-ethyl]-3-[7-(5-trifluoromethyl-pyridin-3-yl)-[1,2,4]triazolo[1,5-a]pyridin-2-yl]-urea | 447.13 | 0.640 |
| 3-17 | 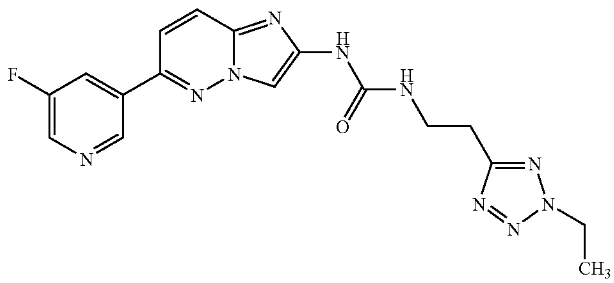 | 1-[2-(2-Ethyl-2H-tetrazol-5-yl)-ethyl]-3-[6-(5-fluoro-pyridin-3-yl)-imidazo[1,2-b]pyridazin-2-yl]-urea | 397.51 | 0.107 |
| 3-18 | 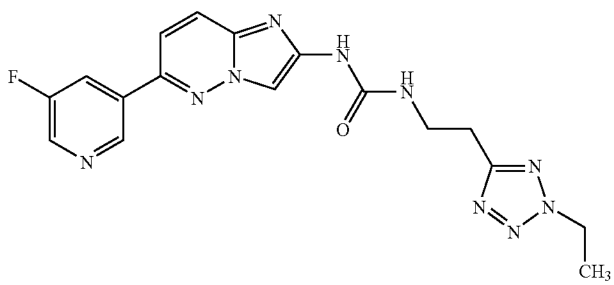 | 1-[2-(2-Ethyl-2H-tetrazol-5-yl)-ethyl]-3-[6-(4-methyl-pyridin-3-yl)-imidazo[1,2-b]pyridazin-2-yl]-urea | 393.51 | 0.248 |

Abbreviations used are as follows: rt is room temperature, CDI is 1,1'-carbonyldiimidazole, DCM is dichloromethane, DIPEA is diisopropylethylamine, THF is tetrahydrofuran, HPLC is High Performance Liquid Chromatography, DMF is N,N-Dimethylformamide, DMSO is dimethyl sulfoxide, TFA is Trifluoroacetic acid. HOBT is Hydroxy benzotriazole, and HOAt is Hydroxy azabenzotriazole. EDC1 is N-(3-dimethylaminopropyl)-N'-ethylcarbodiimide hydrochloride, EtOAc is ethylacetate, DME is 1,2-dimethoxyethane, DEAD is diethyl-azodicarboxylate, DMAP is 4-dimethylaminopyridine, DCI is 4,5-dicyanoimidazole, NMP is 1,Methyl-2-pyrrolidinone.

Preparation of Specific Examples

A typical example is as follows:

Example 1-1

1-[2-(2-Isopropyl-2H-tetrazol-5-yl)-ethyl]-3-(6-pyridin-3-yl-imidazo[1,2-a]pyridin-2-yl)-urea A microwave vial is charged with pyridine-3-boronic acid (0.031 g, 0.25 mmol), 2M aqueous sodium carbonate (1 ml) and DME (3 ml) and then purged with Argon for 30 minutes at room temperature. 1-(6-Bromo-imidazo[1,2-a]pyridin-2-yl)-3-[2-(2-isopropyl-2H-tetrazol-5-yl)-ethyl]-urea (Intermediate E1)(0.05 g, 0.13 mmol) and [1,1'-Bis(diphenylphosphino)ferrocene]palladium(II) chloride (0.016 g, 0.02 mmol) are added and the reaction mixture is heated using microwave radiation at 100° C. for 30 minutes. The reaction mixture is filtered through Celite® (filter agent) and washed through with EtOAc. The crude product is absorbed on silica and purified by flash chromatography, eluting with methanol in DCM (3%) to afford the title compound.

Examples 1-2 to 1-18

These compounds namely,
1-[2-(2-Isopropyl-2H-tetrazol-5-yl)-ethyl]-3-(6-pyridin-4-yl-imidazo[1,2-a]pyridin-2-yl)-urea (Example 1-2)
1-[6-(5-Cyano-pyridin-3-yl)-imidazo[1,2-a]pyridin-2-yl]-3-[2-(2-isopropyl-2H-tetrazol-5-yl)-ethyl]-urea (Example 1-3)
1-[2-(2-Isopropyl-2H-tetrazol-5-yl)-ethyl]-3-(6-pyrimidin-5-yl-imidazo[1,2-a]pyridin-2-yl)-urea (Example 1-4)
1-[2-(2-Ethyl-2H-tetrazol-5-yl)-ethyl]-3-(6-pyridin-3-yl-imidazo[1,2-a]pyridin-2-yl)-urea (Example 1-5)
1-[6-(5-Ethoxy-pyridin-3-yl)-imidazo[1,2-a]pyridin-2-yl]-3-[2-(2-isopropyl-2H-tetrazol-5-yl)-ethyl]-urea (Example 1-6)
1-[2-(2-Isopropyl-2H-tetrazol-5-yl)-ethyl]-3-[6-(5-trifluoromethyl-pyridin-3-yl)-imidazo[1,2-a]pyridin-2-yl]-urea (Example 1-7)

1-(6-Benzo[1,3]dioxol-5-yl-imidazo[1,2-a]pyridin-2-yl)-3-[2-(2-ethyl-2H-tetrazol-5-yl)-ethyl]urea (Example 1-8)

1-[2-(2-Ethyl-2H-tetrazol-5-yl)-ethyl]-3-[6-(3-trifluoromethyl-phenyl)-imidazo[1,2-a]pyridin-2-yl]-urea (Example 1-9)

1-[2-(2-Isopropyl-2H-tetrazol-5-yl)-ethyl]-3-(6-phenyl-imidazo[1,2-a]pyridin-2-yl)-urea (Example 1-10)

N-tert-Butyl-3-[3-(6-pyridin-3-yl-imidazo[1,2-a]pyridin-2-yl)-ureido]-propionamide (Example 1-11)

1-[6-(5-Chloro-pyridin-3-yl)-imidazo[1,2-a]pyridin-2-yl]-3-[2-(2-isopropyl-2H-tetrazol-5-yl)-ethyl]urea (Example 1-12)

1-[2-(2-Isopropyl-2H-tetrazol-5-yl)-ethyl]-3-{6-[5-(tetrahydro-pyran-4-yloxy)-pyridin-3-yl}-imidazo[1,2-a]pyridin-2-yl]-urea (Example 1-13)

1-[6-(5-Chloro-2-methoxy-phenyl)-imidazo[1,2-a]pyridin-2-yl]-3-[2-(2-ethyl-2H-tetrazol-5-yl)-ethyl]urea (Example 1-14)

N-tert-Butyl-3-{3-[6-(5-phenyl-pyridin-3-yl)-imidazo[1,2-a]pyridin-2-yl]ureido}-propionamide (Example 1-15)

1-[2-(2-Isopropyl-2H-tetrazol-5-yl)-ethyl]-3-[6-(5-phenyl-pyridin-3-yl)-imidazo[1,2-a]pyridin-2-yl]urea (Example 1-16)

1-[2-(2-Isopropyl-2H-tetrazol-5-yl)-ethyl]-3-(6-{5-[2-(2-methoxy-ethoxy)-ethoxy]-pyridin-3-yl}-imidazo[1,2-a]pyridin-2-yl)-urea (Example 1-17)

N-tert-Butyl-3-(3-{6-[5-(tetrahydro-pyran-4-yloxy)-pyridin-3-yl]-imidazo[1,2-a]pyridin-2-yl}-ureido)-propionamide (Example 1-18)

are prepared analogously to Example 1-1 from the appropriate imidazole-urea bromo intermediate and boronic acids/boronate esters. The compounds are recovered from reaction mixtures and purified using conventional techniques such as, for example, flash chromatography, preparative LC-MS.

Example 1-19

1-[2-(2-Isopropyl-2H-tetrazol-5-yl)-ethyl]-3-[6-(6-methoxy-pyridin-3-yl)-imidazo[1,2-a]pyridin-2-yl]-urea Triethylamine (0.54 ml, 3.26 mmol) is added to a stirred mixture of [6-(6-methoxy-pyridin-3-yl)-imidazo[1,2-a]pyridin-2-yl]carbamic acid phenyl ester (Intermediate C) (0.587 g, 1.63 mmol) and 2-(2-isopropyl-2H-tetrazol-5-yl)-ethylamine hydrochloride (Intermediate D1)(0.275 g, 1.96 mmol) in NMP (5 ml). The resulting mixture is stirred at 80° C. for 2 hours and then allowed to cool to room temperature. Water (100 ml) is added and the resulting grey suspension is collected by filtration and dried in a vacuum oven to afford the title compound.

Examples 1-20

1-[2-[2-(2-Fluoro-ethyl)-2H-tetrazol-5-yl]-ethyl]-3-[6-(6-methoxy-pyridin-3-yl)-imidazo[1,2-a]pyridin-2-yl]-urea This compound is prepared analogously to Example 1-19 by replacing 2-(2-isopropyl-2H-tetrazol-5-yl)-ethylamine hydrochloride (Intermediate D1) with 242-(2-fluoro-ethyl)-2H-tetrazol-5-0'-ethylamine (Intermediate D3).

Example 1-21 to 1-44

These compounds namely, 1-(2-Ethyl-2H-tetrazol-5-ylmethyl)-3-[6-(5-trifluoromethyl-pyridin-3-yl)-imidazo[1,2-a]pyridin-2-yl]urea (Example 1-21), 1-[6-(5-Ethyl-pyridin-3-yl)-imidazo[1,2-a]pyridin-2-yl]-3-[2-(2-isopropyl-2H-tetrazol-5-yl)-ethyl]-urea (Example 1-22)

1-[2-(1-Ethyl-1H-imidazol-4-yl)-ethyl]-3-[6-(5-trifluoromethyl-pyridin-3-yl)-imidazo[1,2-a]pyridin-2-yl]-urea (Example 1-23)

1-[2-(2-Isopropyl-2H-tetrazol-5-yl)-ethyl]-3-[6-(6-methyl-pyridin-3-yl)-imidazo[1,2-a]pyridin-2-yl]urea (Example 1-24)

1-[2-(5-Ethyl-tetrazol-2-yl)-ethyl]-3-[6-(5-trifluoromethyl-pyridin-3-yl)-imidazo[1,2-a]pyridin-2-yl]urea (Example 1-25)

1-[6-(5-Cyano-pyridin-3-yl)-imidazo[1,2-a]pyridin-2-yl]-3-[2-(5-ethyl-tetrazol-2-yl)-ethyl]-urea (Example 1-26)

1-[2-(5-Cyclopropyl-tetrazol-2-yl)-ethyl]-3-[6-(5-trifluoromethyl-pyridin-3-yl)-imidazo[1,2-a]pyridin-2-yl]-urea (Example 1-27)

1-[6-(3-Fluoro-phenyl)-imidazo[1,2-a]pyridin-2-yl]-3-[2-(2-isopropyl-2H-tetrazol-5-yl)-ethyl]urea (Example 1-28)

1-[2-(2-Isopropyl-2H-tetrazol-5-yl)-ethyl]-3-[6-(3-methoxy-phenyl)-imidazo[1,2-a]pyridin-2-yl]-u (Example 1-29)

1-[2-(2-Ethyl-2H-tetrazol-5-yl)-ethyl]-3-(6-quinolin-3-yl-imidazo[1,2-a]pyridin-2-yl)-urea (Example 1-30)

1-[2-(2-Isopropyl-2H-tetrazol-5-yl)-ethyl]-3-(6-phenyl-imidazo[1,2-a]pyridin-2-yl)-urea (Example 1-31)

1-[2-(1-Ethyl-1H-imidazol-4-yl)-ethyl]-3-(6-pyridin-3-yl-imidazo[1,2-a]pyridin-2-yl)-urea (Example 1-32)

3-[3-(6-Pyridin-3-yl-imidazo[1,2-a]pyridin-2-yl)-ureido]-propionic acid tert-butyl ester (Example 1-33)

1-[2-(2-Ethyl-2H-tetrazol-5-yl)-ethyl]-3-[6-(5-trifluoromethyl-pyridin-3-yl)-imidazo[1,2-a]pyridin-2-yl]-urea (Example 1-34)

1-{2-[2-(2-Fluoro-ethyl)-2H-tetrazol-5-yl]-ethyl}-3-[6-(5-trifluoromethyl-pyridin-3-yl)-imidazo[1,2-a]pyridin-2-yl]-urea (Example 1-35)

1-[2-(2-Methyl-2H-tetrazol-5-yl)-ethyl]-3-(6-pyridin-3-yl-imidazo[1,2-a]pyridin-2-yl)-urea (Example 1-36)

1-[2-(1-Methyl-1H-tetrazol-5-yl)-ethyl]-3-(6-pyridin-3-yl-imidazo[1,2-a]pyridin-2-yl)-urea (Example 1-37)

1-[2-(2-Methyl-2H-tetrazol-5-yl)-ethyl]-3-[6-(5-trifluoromethyl-pyridin-3-yl)-imidazo[1,2-a]pyridin-2-yl]-urea (Example 1-38)

1-[2-(2-Isopropyl-2H-tetrazol-5-yl)-ethyl]-3-[6-(5-o-tolyl-pyridin-3-yl)-imidazo[1,2-a]pyridin-2-yl]urea (Example 1-39)

1-[2-(2-Ethyl-2H-tetrazol-5-yl)-ethyl]-3-[6-(1-methyl-1H-pyrazol-4-yl)-imidazo[1,2-a]pyridin-2-yl]urea (Example 1-40)

1-[6-(1-Benzyl-1H-pyrazol-4-yl)-imidazo[1,2-a]pyridin-2-yl]-3-[2-(2-ethyl-2H-tetrazol-5-yl)-ethyl]-urea (Example 1-41)

1-[2-(2-Ethyl-2H-tetrazol-5-yl)-ethyl]-3-(6-isoquinolin-4-yl-imidazo[1,2-a]pyridin-2-yl)-urea (Example 1-42)

1-[6-(5-Acetyl-pyridin-3-yl)-imidazo[1,2-a]pyridin-2-yl]-3-[2-(2-isopropyl-2H-tetrazol-5-yl)-ethyl]urea (Example 1-43)

1-[2-(5-Ethyl-tetrazol-2-yl)-ethyl]-3-(6-pyridin-3-yl-imidazo[1,2-a]pyridin-2-yl)-urea (Example 1-44)

are prepared analogously to Example 1-1 from the appropriate imidazole-urea bromo intermediate and boronic acids/boronate esters. The compounds are recovered from reaction mixtures and purified using conventional techniques such as, for example, flash chromatography, preparative LC-MS.

Example 1-45

1-(6-Bromo-imidazo[1,2-a]pyridin-2-yl)-3-[2-(2-ethyl-2H-tetrazol-5-yl)-ethyl]-urea This compound is prepared analogously to Intermediate E1 (described in preparation of intermediates section) by replacing 2-(2-isopropyl-2H-tetrazol-5-yl)-ethylamine hydrochloride (Intermediate D1) with 2-(2-ethyl-2H-tetrazol-5-yl)-ethylamine (Intermediate D2).

Example 1-46

3-[3-(6-Bromo-imidazo[1,2-a]pyridin-2-yl)-ureido]-N-(5-methyl-isoxazo-3-yl)-propionamide This compound is prepared analogously to Intermediate E1 (described in preparation of intermediates section) by replacing 2-(2-isopropyl-2H-tetrazol-5-yl)-ethylamine hydrochloride (Intermediate D1) with 3-Amino-N-(5-methyl-isoxazol-3-yl)-propionamide (Intermediate D5).

Example 1-47 to 1-49

These compounds namely,
1-[2-(2-Isopropyl-2H-tetrazol-5-yl)-ethyl]-3-[6-(5-methanesulfonyl-pyridin-3-yl)-imidazo[1,2-a]pyridin-2-yl]-urea (Example 1-47)
1-[6-(5-Fluoro-pyridin-3-yl)-imidazo[1,2-a]pyridin-2-yl]-3-[2-(2-isopropyl-2H-tetrazol-5-yl)-ethyl]urea (Example 1-48)
1-[2-(2-Isopropyl-2H-tetrazol-5-yl)-ethyl]-3-(6-quinolin-3-yl-imidazo[1,2-a]pyridin-2-yl)-urea (Example 1-49)
are prepared analogously to Example 1-1 from the appropriate imidazole-urea bromo intermediate and boronic acids/boronate esters. The compounds are recovered from reaction mixtures and purified using conventional techniques such as, for example, flash chromatography, preparative LC-MS.

Examples 2-1 to 2-12

These compounds namely,
1-{2-[2-(2-Fluoro-ethyl)-2H-tetrazol-5-yl]-ethyl}-3-(6-pyridin-3-yl-benzothiazol-2-yl)-urea (Example 2-1)
1-{2-[2-(2-Fluoro-ethyl)-2H-tetrazol-5-yl]-ethyl}-3-[6-(6-methoxy-pyridin-3-yl)-benzothiazol-2-yl]-urea (Example 2-2)
1-(2-Dimethylamino-ethyl)-3-[6-(6-methoxy-pyridin-3-yl)-benzothiazol-2-yl]urea (Example 2-3)
1-(2-Hydroxy-ethyl)-3-[6-(6-methoxy-pyridin-3-yl)-benzothiazol-2-yl]-urea (Example 2-4)
1-[6-(6-Methoxy-pyridin-3-yl)-benzothiazol-2-yl]-3-pyridin-3-ylmethyl-urea (Example 2-5)
1-Ethyl-3-[6-(6-methoxy-pyridin-3-yl)-benzothiazol-2-yl]urea (Example 2-6)
1-{2-[2-(2-Fluoro-ethyl)-2H-tetrazol-5-yl]-ethyl}-3-{6-[5-(morpholine-4-carbonyl)-pyridin-3-yl]-benzothiazol-2-yl}-urea (Example 2-7)
1-{2-[2-(2-Fluoro-ethyl)-2H-tetrazol-5-yl]-ethyl}-3-[6-(5-trifluoromethyl-pyridin-3-yl)-benzothiazol-2-yl]urea (Example 2-8)
1-[2-(2-Ethyl-2H-tetrazol-5-yl)-ethyl]-3-[6-(5-trifluoromethyl-pyridin-3-yl)-benzothiazol-2-yl]-urea (Example 2-9)
1-[2-(2-Isopropyl-2H-tetrazol-5-yl)-ethyl]-3-[6-(5-trifluoromethyl-pyridin-3-yl)-benzothiazol-2-yl]urea (Example 2-10)
1-[2-(5-Ethyl-tetrazol-2-yl)-ethyl]-3-[6-(5-trifluoromethyl-pyridin-3-yl)-benzothiazol-2-yl]urea (Example 2-11)
1-[2-(1-Ethyl-1H-imidazol-4-yl)-ethyl]-3-[6-(5-trifluoromethyl-pyridin-3-yl)-benzothiazol-2-yl]-urea (Example 2-12)
are prepared analogously to Example 1-1 from the appropriate thiazole-urea bromo intermediates (F1-F7) and boronic acids/boronate esters. The compounds are recovered from reaction mixtures and purified using conventional techniques such as, for example, flash chromatography, preparative LC-MS.

Examples 3-1 to 3-18

These compounds named in Table 3 are prepared analogously to Example 1.1 by replacing 6-bromo-imidazo[1,2-a]pyridin-2-ylamine (Intermediate E1) with the appropriate imidazole or triazole-urea intermediate (Intermediates E) and by using the appropriate boronic acids/boronate esters. The compounds are recovered from reaction mixtures and purified using conventional techniques such as, for example, flash chromatography, preparative LC-MS.

Preparation of Intermediates

Intermediate A1

6-Bromo-imidazo[1,2-a]pyridin-2-ylamine

Step 1: N-[5-Bromo-1H-pyridin-(2Z)-ylidene]-4-methyl-benzenesulfonamide

Tosyl chloride (52.9 g, 277.4 mmol) is added slowly to a stirred solution of 2-amino-5-bromopyridine (40.0 g, 231 mmol) in dry pyridine (240 ml) at 0° C. The reaction is heated at 90° C. for 16 hours. The solvent is removed in vacuo and water (500 ml) is added and the mixture is stirred for 30 minutes at room temperature. The title compound is collected by filtration and dried in a vacuum oven at 50° C.

Step 2: 2-{5-Bromo-2-[(Z)-toluene-4-sulfonylimino]-2H-pyridin-1-yl}-acetamide

N-[5-Bromo-1H-pyridin-(2Z)-ylidene]-4-methyl-benzenesulfonamide (80 g, 244.5 mmol) is suspended in anhydrous DMF (350 ml). Hunigs base (46.8 ml, 268.9 mmol) is added followed by 2-bromoacetamide (37.12 g, 268.9 mmol) and the mixture is stirred at room temperature for 72 hours. The reaction is poured into water (1000 ml) and the mixture is stirred for 1 hour. The product is collected by filtration, washed with more water (300 ml) and dried in a vacuum oven at 50° C. to give the title compound.

Step 3: N-(6-Bromo-imidazo[1,2-a]pyridin-2-yl)-2,2,2-trifluoro-acetamide.

Trifluoroacetic anhydride (100 ml) is added slowly to a stirred suspension of 2-{5-bromo-2-[(Z)-toluene-4-sulfonylimino]-2H-pyridin-1-yl}-acetamide (20 g, 52 mmol) in anhydrous dichloromethane (250 ml). The reaction is heated at reflux for 3 hours and then allowed to cool to room temperature. The solvent is removed in vacuo to afford a yellow solid consisting of the tosic acid salt of the title compound. The solid is suspended in aqueous sodium bicarbonate solution and stirred for 15 minutes followed by filtration to provide the title compound. $^1$H nmr (CDCl$_3$): 7.37 (1H, d), 7.43 (1H, d), 8.15 (1H, s), 8.43 (1H, s), 10.2 (1H, s).

Step 4: 6-Bromo-imidazo[1,2-a]pyridin-2-ylamine

A stirred solution of N-(6-bromo-imidazo[1,2-a]pyridin-2-yl)-2,2,2-trifluoro-acetamide (9.0 g, 29.2 mmol) in DME (90 ml) and 1.27 M aqueous potassium phosphate (80.5 ml, 102.3 mmol) is heated at 90° C. overnight. After cooling to room temperature, the two layers are separate and the aqueous portion is extracted with EtOAc. The combined organic extracts are concentrated in vacuo to afford a brown oil. Iso-hexanes is added to the oil resulting in the formation of a solid. The excess iso-hexanes is decanted off and the remaining DME is azeotroped with THF (2×50 ml) to afford the title compound as a solid [MH+ 211.93].

Intermediate A2

7-Bromo-[1,2,4]triazolo[1,5-a]pyridin-2-ylamine

This intermediate is prepared according to WO2006038116, page 21.

Intermediate A3

6-Bromo-[1,2,4]-triazolo[1,5-a]pyridin-2-ylamine

Step 1

2-Amino-5-bromo-pyridine (2.5 g, 14.45 mmol) is dissolved in dry 1,4-dioxane (30 ml) and carbethoxy isothiocyanate (1.70 ml, 14.45 mmol) is added via syringe. The reaction mixture is stirred overnight at room temperature after which time a precipitate is observed. The solvent is removed in vacuo and the residue is dissolved in MeOH/EtOAc and absorbed onto silica. Purification by flash chromatography eluting with 1:1 EtOAc/iso-hexanes affords the title compound.

Step 2

A solution of the intermediate from step 1 (2.0 g, 6.58 mmol) in dry DMF (15 ml) is treated with K$_2$CO$_3$ (1.18 g, 8.55 mmol) followed by methyl iodide (0.49 ml, 7.90 mmol) and the reaction mixture is heated to 35° C. for 3 days. The reaction mixture is cooled to room temperature and concentrated in vacuo. Water (40 ml) is added followed by 1:1 EtOAc/iso-hexanes (150 ml) and the aqueous phase is separated. The organic portion is washed with water (2×40 ml) and brine (30 ml), dried over MgSO$_4$ and concentrated in vacuo. Purification by flash chromatography on silica eluting with EtOAc/iso hexanes (20% increasing to 50% EtOAc) affords the title compound.

Step 3:
6-Bromo-[1,2,4]triazolo[1,5-a]pyridin-2-ylamine

Hydroxylamine hydrochloride (0.330 g, 5.13 mmol) is suspended in EtOH (70 ml) and treated with DIPEA (0.89 ml, 5.13 mmol) is added. The reaction mixture is stirred at room temperature for 10 minutes and then transferred by syringe to a suspension of the product from step 2 (0.726 g, 2.28 mmol) in EtOH (10 ml), the reaction vessel is fitted with a reflux condenser (connected to a trap containing bleach) and the reaction mixture is stirred at room temperature for 10 minutes before heating to 80° C. for 2 hours. On cooling the reaction mixture is concentrated to 20% original volume resulting in a white precipitate. The mixture is dissolved in DCM (75 ml) and washed with water (50 ml) and brine (50 ml). The organic phase is dried over MgSO$_4$, filtered and concentrated in vacuo to afford the title compound [MH+ 212.90].

Intermediate A4-A11

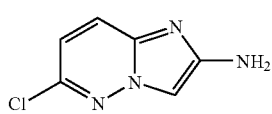
A4

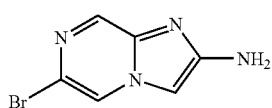
A5

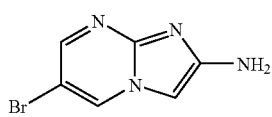
A6

These compounds namely,
A4: 6-Chloro-imidazo[1,2-b]pyridazin-2-ylamine
A5: 6-Bromo-imidazo[1,2-a]pyrazin-2-ylamine
A6: 6-Bromo-imidazo[1,2-a]pyrimidin-2-ylamine
are prepared as follows:
A4-A6: are prepared analogously to Intermediate A1 by replacing 2-amino-5-bromopyridine with 6-chloro-3-pyridazinamine, 2-amino-5-bromopyrazine and 2-amino-5-bromopyrimidine respectively.

Intermediate B1

(6-Bromo-imidazo[1,2-a]pyridin-2-yl)-carbamic acid phenyl ester

To a solution of 6-bromo-imidazo[1,2-a]pyridin-2-ylamine (Intermediate A1)(6.2 g, 29.2 mmol) in THF (400 ml) is added 2,4,6-trimethylpyridine (5.8 ml, 43.9 mmol). The reaction mixture is cooled to 0° C. (ice-bath) and treated dropwise with a solution of phenyl chloroformate (3.85 ml, 30.7 mmol) in THF (50 ml) over 15 minutes. The reaction mixture is stirred overnight, at room temperature, quenched with water and stirred for a further 5 minutes resulting in a white precipitate. The solid is collected by filtration and dried under vacuum (40° C.) overnight to afford the title compound [MH+ 331.99 and 333.99].

Intermediate B2

Imidazole-1-carboxylic acid (6-bromo-benzothiazol-2-yl)-amide

A suspension of 6-bromo-benzothiazol-2-ylamine (5 g, 21.83 mmol) in DCM (250 ml) is treated with CDI (3.54 g, 21.83 mmol) and the reaction mixture is heated to reflux for 2 hours. The reaction mixture is filtered and the resulting solid is dried in the vacuum oven overnight to afford the title compound.

Intermediate C

[6-(6-Methoxy-pyridin-3-yl)-imidazo[1,2-a]pyridin-2-yl]-carbamic acid phenyl ester Step 1: 6-(6-Methoxy-pyridin-3-yl)-imidazo[1,2-a]pyridin-2-ylamine N-(6-Bromo-imidazo[1,2-a]pyridin-2-yl)-2,2,2-trifluoro-acetamide (Intermediate A1, step 3) (0.84 g, 2.72 mmol), 2-methoxy-5-pyridineboronic acid (0.50 g, 3.27 mmol) and dry 1,4-dioxane (10 ml) are placed in a microwave vial and purged with Argon. Pd(PPh$_3$)$_4$ (0.16 g, 0.14 mmol) is added followed by a solution of Cs$_2$CO$_3$ in water (2.66 g, 8.16 mmol in 3 ml). The reaction mixture is heated using microwave radiation at 150° C. for 45 minutes and then left overnight at room temperature. The mixture is filtered through Celite® (filter agent) and washed through with EtOAc (100 ml). The organic filtrate is washed with NaHCO$_3$ (50 ml) and brine (50 ml), dried over MgSO$_4$, filtered and concentrated in vacuo. Purification by flash chromatography on silica eluting with MeOH in DCM (1% increasing to 10%) affords the title compound. [MH+241.07].

Step 2: [6-(6-Methoxy-pyridin-3-yl)-imidazo[1,2-a]pyridin-2-yl]-carbamic acid phenyl ester This compound is prepared analogous to Intermediate B1 by replacing 6-bromo-imidazo[1,2-a]pyridin-2-ylamine (Intermediate A1) with 6-(6-methoxy-pyridin-3-yl)-imidazo[1,2-a]pyridin-2-ylamine and by replacing 2,4,6-trimethylpyridine with DIPEA to afford the title compound [MH+360.97]. The reaction is carried out in DCM.

Intermediates D1-D12

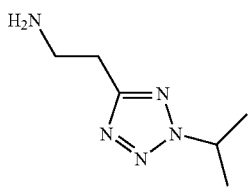
D1

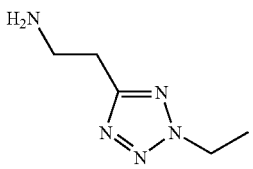
D2

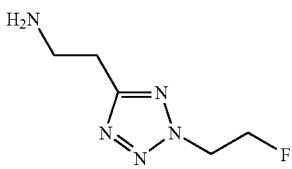
D3

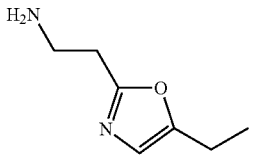
D4

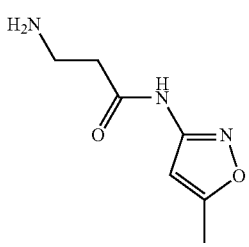
D5

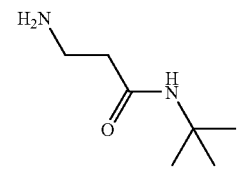
D6

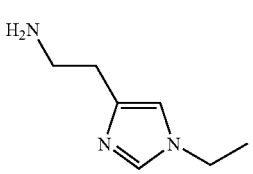
D7

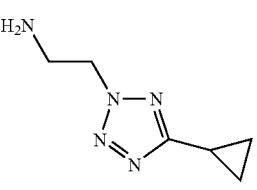
D8

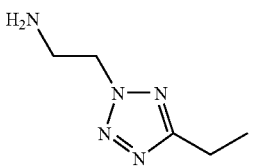
D9

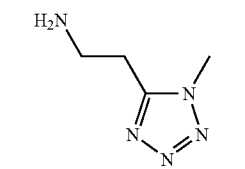
D10

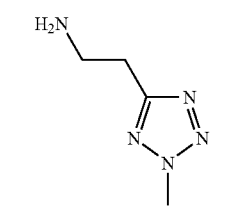
D11

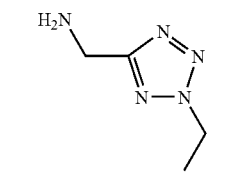
D12

These intermediates, namely
D1 2-(2-Isopropyl-2H-tetrazol-5-yl)-ethylamine
D2 2-(2-Ethyl-2H-tetrazol-5-yl)-ethylamine,
D3 2-[2-(2-Fluoro-ethyl)-2H-tetrazol-5-yl]-ethylamine
D4 2-(5-Ethyl-oxazol-2-yl)-ethylamine
D5 3-Amino-N-(5-methyl-isoxazol-3-yl)-propionamide D6 3-Amino-N-tert-butyl-propionamide
D7 2-(1-Ethyl-1H-imidazol-4-yl)-ethylamine
D8 2-(5-Cyclopropyl-tetrazol-2-yl)-ethylamine
D9 2-(5-Ethyl-tetrazol-2-yl)-ethylamine
D10 2-(1-Methyl-1H-tetrazol-5-yl)-ethylamine
D11 2-(2-Methyl-2H-tetrazol-5-yl)-ethylamine
D12 C-(2-Ethyl-2H-tetrazol-5-yl)-methylamine
are prepared as follows:
Intermediates D1-D4 are prepared according to Bloomfield, Graham Charles; Bruce, Ian; Hayler, Judy; Leblanc, Catherine; Le Grand, Darren Mark; McCarthy, Clive. Preparation of phenylthiazolylureas as inhibitors of phosphatidylinositol 3-kinase. PCT Int. Appl. (2005), 88 pp. WO 2005021519.

Intermediate D5

3-Amino-N-(5-methyl-isoxazol-3-yl)-propionamide

A solution of DMAP (9.77 g, 0.08 mol), TEA (55.23 ml, 0.396 mol) and DCI (49.01 ml, 0.317 mol) in DCM (250 ml) is treated with 5-methyl-isoxazole-3-ylamine (28.8 g, 0.290 mol) and Boc-Beta-Ala-OH (50 g, 0.264 mol). The reaction mixture is stirred at room temperature for 18 hours and then diluted with DCM (1750 ml). The mixture is washed with 10% citric acid (2×500 ml), saturated sodium hydrogen carbonate solution (2×500 ml) and brine (600 ml). The organic portion is dried (MgSO$_4$), concentrated in vacuo and the crude residue is stirred with iso-hexanes (750 ml) for 1 hour. The resulting solid is dissolved in dioxane (400 ml) and treated with 4M HCl in dioxane (350 ml). After 1 hour the precipitate is filtered and washed with dioxane (100 ml) to afford the title compound as the hydrochloride salt [MH+ 169.84].

Intermediate D6

3-Amino-N-tert-butyl-propionamide

Step 1: (2-tert-Butylcarbamoyl-ethyl)-carbamic acid tert-butyl ester

BOC-Beta-Ala-OH (25 g, 0.132 mol) is dissolved in DCM (500 ml) and then treated with EDC1 (30.4 g, 0.59 mol) followed by t-butylamine (16.7 ml, 0.159 mol) to give a pale orange solution. The reaction mixture is stirred at room temperature overnight and then partitioned between 20% citric acid (400 ml) and DCM (250 ml). The organic portion is separated and washed with water (400 ml), saturated NaHCO$_3$ (400 ml), brine (400 ml), dried over MgSO$_4$ and concentrated in vacuo to afford the title compound as a white solid.

Step 2: 3-Amino-N-tert-butyl-propionamide (2-tert-Butylcarbamoyl-ethyl)-carbamic acid tert-butyl ester (27.1 g, 0.111 mol) is dissolved in 1,4-dioxane (500 ml) and treated with 4M HCl in 1,4-dioxane (69 ml). The reaction mixture is stirred at room temperature for 72 hours resulting in a white precipitate. The solid is filtered, washed with 1,4-dioxane (50 ml) and dried in the vacuum oven (45° C.) to afford the title compound as the HCl salt.

Intermediate D7

2-(1-Ethyl-1H-imidazol-4-yl)-ethylamine

This compound is prepared according to Bloomfield, Graham Charles; Bruce, Ian; Hayler, Judy; Leblanc, Catherine; Le Grand, Darren Mark; McCarthy, Clive. Preparation of phenylthiazolylureas as inhibitors of phosphatidylinositol 3-kinase. PCT Int. Appl. (2005), 88 pp. WO 2005021519.

Intermediate D8

2-(5-Cyclopropyl-tetrazol-2-yl)-ethylamine

Step 1: [2-(5-Cyclopropyl-tetrazol-2-yl)-ethyl]arbamic acid tert-butyl ester

5-Cyclopropyl-2H-tetrazole (0.5 g, 4.5 mmol) is dissolved in dry acetonitrile (7 ml) and triethylamine (9.5 ml, 68 mmol). The reaction mixture is stirred for 10 minutes at room temperature then 2-(BOC-amino)ethyl bromide is added and the mixture is heated to reflux 3 hours. The reaction mixture is partitioned between water and EtOAc and the organic extract is dried (MgSO$_4$) and concentrated in vacuo. Purification by flash chromatography on a 100 g Jones silica cartridge eluting with 50% EtOAc: iso-hexanes affords the title compound as a colourless oil.

Step 2: 2-(5-Cyclopropyl-tetrazol-2-yl)-ethylamine

[2-(5-Cyclopropyl-tetrazol-2-yl)-ethyl]-carbamic acid tert-butyl ester (0.42 g, 1.65 mmol) is dissolved in DCM (3 ml) and 4M HCl in 1,4-dioxane (2 ml) is added. The reaction mixture is stirred at room temperature overnight and the resulting precipitate is filtered and dried under vacuum overnight at 30° C. to afford the title compound as the HCl salt.

Intermediate D9

2-(5-Ethyl-tetrazol-2-yl)-ethylamine

Step 1: 5-Vinyl-2H-tetrazole

AlCl3 (3.3 g, 25 mmol) is placed in an oven dried flask under an atmosphere of Argon. 50 ml of dry THF is slowly added followed by the slow addition of NaN$_3$ (6.4 g, 99 mmol) and finally acrylonitrile (1.32 g, 25 mmol). The reaction mixture is stirred at reflux for 2 hours, cooled to room temperature then 15% HCl (40 ml) is slowly added and the solution is purged with Argon for 5 minutes. The reaction mixture is partitioned between EtOAc and water and the organic portion is separated, washed with brine, dried over MgSO$_4$, filtered and concentrated in vacuo. Purification by recrystallisation from CHCl$_3$ affords the title compound.

Step 2: 5-Ethyl-2H-tetrazole

5-Vinyl-2H-tetrazole (1.2 g, 12.5 mmol) is dissolved in MeOH under an atmosphere of Argon. A catalytic amount of 10% palladium on carbon is added and the flask is purged with hydrogen. After stirring at room temperature for 1 hour, the catalyst is removed by filtration through a Celite® (filter agent) and the solvent is concentrated in vacuo to afford the title compound.

Step 3: [2-(5-Ethyl-tetrazol-2-yl)-ethyl]carbamic acid tert-butyl ester

This compound is prepared analogously to Intermediate D8 (step 1) by replacing 5-cyclopropyl-2H-tetrazole with 5-ethyl-2H-tetrazole. Purification by flash chromatography on a 100 g Jones silica cartridge eluting with 0 to 4% MeOH: $CH_2Cl_2$ affords the title compound as a colourless oil.

Step 4: 2-(5-Ethyl-tetrazol-2-yl)-ethylamine

This compound is prepared analogously to Intermediate D8 (step 2) by replacing [2-(5-cyclopropyl-tetrazol-2-yl)-ethyl]-carbamic acid tert-butyl ester with [2-(5-ethyl-tetrazol-2-yl)-ethyl]-carbamic acid tert-butyl ester to afford the title compound as the HCl salt.

Intermediate D10

2-(2-Methyl-2H-tetrazol-5-yl)-ethylamine

Step 1: (2-Cyano-ethyl)-carbamic acid tert-butyl ester (i) A solution of the fumerate salt of 3-aminopropionitrile (128 g, 1 mol) in water (375 ml) is treated with 4M NaOH (250 ml, 1 mol) and the reaction mixture is stirred for 1 hour. The solution is washed with DCM (3×250 ml) and the aqueous portion is added to a solution of di-tert-butyl dicarbonate (218 g, 1 mol) in 1,4-dioxane (500 ml) followed by the portionwise addition of solid $NaHCO_3$ over a period of 1 hour. The reaction mixture is stirred overnight at room temperature resulting in the formation of a suspension. The suspension is washed with DCM (500 ml), the layers are separated and the aqueous layer is re-extracted with DCM (250 ml). The combined organic extracts are washed with water (1 liter), saturated $NaHCO_3$ (500 ml), brine (500 ml), dried over $MgSO_4$, filtered and concentrated in vacuo to afford an oil. The oil is left under vacuum overnight resulting in a crystalline solid. The solid is stirred in iso-hexanes (500 ml) for 1 hour, filtered and dried under vacuum to afford the title compound as a white solid.

Step 2: [2-(1H-Tetrazol-5-yl)-ethyl]carbamic acid tert-butyl ester (2-Cyano-ethyl)-carbamic acid tert-butyl ester (59.5 g, 0.35 mol) is dissolved in dry m-xylene 460 ml) and stirred at room temperature. Azidotributyltin (140 g, 0.42 mol) is added and the reaction mixture is heated to 115° C. overnight. On cooling to room temperature, the reaction mixture is quenched with 2M NaOH (500 ml), the layers are separated and the aqueous phase is acidified with 6M HCl to pH 2 resulting in a thick precipitate. DCM (500 ml) is added followed by IPA (50 ml) resulting in clear layers, the organic layer is separated and the aqueous is re-extracted with 9:1 DCM/IPA (2×250 ml). The organic layers are combined, washed with brine (500 ml), dried over $MgSO_4$, filtered and concentrated in vacuo. The resulting solid is triturated with iso-hexanes (250 ml), stirred for 1 hour at room temperature then a further 1 hour at 5-10° C., filtered and dried under vacuum to afford the title compound.

Step 3: [2-(1-Methyl-1H-tetrazol-5-yl)-ethyl]-carbamic acid tert-butyl ester

[2-(1H-Tetrazol-5-yl)-ethyl]-carbamic acid tert-butyl ester (0.5 g, 2.34 mmol) is dissolved in dry acetonitrile (21 ml), NaH (60% dispersed in mineral oil) (0.098 g, 2.46 mmol) is added portionwise and the resulting suspension is stirred for 1 hour at room temperature. Methyl iodide (0.15 ml, 2.34 mmol) is added and the reaction mixture is heated to 80° C. for 3 hours, cooled to room temperature and then partitioned between EtOAc (150 ml) and water (2 ml). The organic portion is separated, washed with water, brine, dried over $MgSO_4$, filtered and concentrated in vacuo to afford a mixture of [2-(1-methyl-1H-tetrazol-5-yl)-ethyl]-carbamic acid tert-butyl ester and [2-(2-methyl-2H-tetrazol-5-yl)-ethyl]-carbamic acid tert-butyl ester as an orange oil. Separation of the regioisomers by flash chromatography on silica, eluting with 1:1 EtOAc/iso-hexanes affords the title compound

Step 4: 2-(1-Methyl-1H-tetrazol-5-yl)-ethylamine

[2-(1-Methyl-1H-tetrazol-5-yl)-ethyl]-carbamic acid tert-butyl ester (0.204 g, 0.9 mmol) is dissolved in DCM (3.5 ml). To this solution is added 4M HCl in dioxane (0.9 ml, 3.6 mmol) and the reaction mixture is stirred at room temperature overnight. The solvent is removed in vacuo to afford the title compound as the hydrochloride salt.

Intermediate D11

2-(2-Methyl-2H-tetrazol-5-yl)-ethylamine

This compound is prepared analogously to Intermediate D10 by isolation and deprotection of the second regioisomer, [2-(2-methyl-2H-tetrazol-5-yl)-ethyl]carbamic acid tert-butyl ester, prepared in step 3.

Intermediate D12

C-(2-Ethyl-2H-tetrazol-5-yl)-methylamine

Step 1: (2H-Tetrazol-5-ylmethyl)-carbamic acid tert-butyl ester

C-(2H-tetrazol-5-yl)-methylamine (1 g, 10.1 mmol), di-tert-butyl dicarbonate (2.2 g, 10.1 mmol), 4M NaOH (2.5 ml) and $H_2O$ (20 ml) are mixed together and stirred overnight at room temperature. The reaction mixture is acidified to pH5 with 5M HCl, resulting in a precipitate which is collected by filtration and dried under vacuum to afford the title compound [MH+200.05].

Step 2: (2-Ethyl-2H-tetrazol-5-ylmethyl)-carbamic acid tert-butyl ester (2H-Tetrazol-5-ylmethyl)-carbamic acid tert-butyl ester (0.9 g, 4.5 mmol) is dissolved in dry DMF, NaH (60% dispersed in mineral oil) (0.18 g, 4.5 mmol) is added and the reaction mixture is stirred at room temperature for 5 minutes before ethyl iodide (0.35 ml, 4.5 mmol) is added. The reaction mixture is stirred overnight at room temperature and partitioned between EtOAc and water. The organic phase is dried over $MgSO_4$, filtered and concentrated in vacuo to afford an oil. Purification by flash chromatography on silica eluting with 2:1 iso-hexanes/EtOAc affords the title compound.

Step 3: C-(2-Ethyl-2H-tetrazol-5-yl)-methylamine

This compound is made analogously with Intermediate D10 (step 4) by replacing [2-(1-methyl-1H-tetrazol-5-yl)-ethyl]-carbamic acid tert-butyl ester with (2-ethyl-2H-tetrazol-5-ylmethyl)-carbamic acid tert-butyl ester to afford the title compound as the hydrochloride salt.

Intermediates E1-E13

Intermediate E1

1-(6-Bromo-imidazo[1,2-a]pyridin-2-yl)-3-[2-(2-isopropyl-2H-tetrazol-5-yl)-ethyl]-urea Triethylamine (0.15 ml, 1.1 mmol) is added to a stirred mixture of (6-bromo-imidazo[1,2-a]pyridin-2-yl)-carbamic acid phenyl ester (Intermediate B1)(0.30 g, 0.90 mmol) and 2-(2-isopropyl-2H-tetrazol-5-yl)-ethylamine hydrochloride (Intermediate D1)(0.207 g, 1.1 mmol) in NMP (3 ml). The reaction mixture is stirred at 80° C. for 2 hours, cooled and diluted with water (100 ml) resulting in a grey precipitate. The solid is collected by filtration and dried in a vacuum oven to afford the title compound. [MH+ 395.09]

Intermediates E2-E13

Theses intermediates namely,
E2: 1-(6-Bromo-imidazo[1,2-a]pyridin-2-yl)-3-[2-(2-ethyl-2H-tetrazol-5-yl)-ethyl]-urea
E3: 1-(6-Bromo-imidazo[1,2-a]pyridin-2-yl)-3-{2-[2-(2-fluoro-ethyl)-2H-tetrazol-5-yl]-ethyl}-urea
E4: 1-(6-Bromo-imidazo[1,2-a]pyridin-2-yl)-3-[2-(5-ethyl-oxazol-2-yl)-ethyl]-urea
E5: 3-[3-(6-Bromo-imidazo[1,2-a]pyridin-2-yl)-ureido]-N-(5-methyl-isoxazol-3-yl)-propionamide
E6: 3-[3-(6-Bromo-imidazo[1,2-a]pyridin-2-yl)-ureido]-N-tert-butyl-propionamide
E7: 1-(6-Bromo-imidazo[1,2-a]pyridin-2-yl)-3-[2-(1-ethyl-1H-imidazol-4-yl)-ethyl]-urea
E8: 1-(6-Bromo-imidazo[1,2-a]pyridin-2-yl)-3-[2-(5-ethyl-tetrazol-2-yl)-ethyl]-urea
E9: 1-(6-Bromo-imidazo[1,2-a]pyridin-2-yl)-3-[2-(5-cyclopropyl-tetrazol-2-yl)-ethyl]-urea
E10: 3-[3-(6-Bromo-imidazo[1,2-a]pyridin-2-yl)-ureido]-propionic acid tert-butyl ester
E11: 1-(6-Bromo-imidazo[1,2-a]pyridin-2-yl)-3-[2-(1-methyl-1H-tetrazol-5-yl)-ethyl]-urea
E12: 1-(6-Bromo-imidazo[1,2-a]pyridin-2-yl)-3-[2-(2-methyl-2H-tetrazol-5-yl)-ethyl]-urea
E13: 1-(6-Bromo-imidazo[1,2-a]pyridin-2-yl)-3-(2-ethyl-2H-tetrazol-5-ylmethyl)-urea are prepared analogously to Intermediate E1 by reacting the appropriate tetrazole or oxazoles (Intermediates D2-D12) with the corresponding amines. Preparations of non-commercial amines are described herein.

Further examples of Intermediates E:

These compounds, namely:
1-(6-Bromo-imidazo[1,2-b]pyridazin-2-yl)-3-[2-(2-ethyl-2H-tetrazol-5-yl)-ethyl]-urea
1-(6-Bromo-imidazo[1,2-a]pyrazin-2-yl)-3-[2-(2-ethyl-2H-tetrazol-5-yl)-ethyl]-urea
1-(6-Bromo-[1,2,4]triazolo[1,5-a]pyridin-2-yl)-3-[2-(2-ethyl-2H-tetrazol-5-yl)-ethyl]-urea
1-(7-Bromo-[1,2,4]triazolo[1,5-a]pyridin-2-yl)-3-[2-(2-ethyl-2H-tetrazol-5-yl)-ethyl]-urea
1-(6-Bromo-imidazo[1,2-a]pyrazin-2-yl)-3-[2-(2-isopropyl-2H-tetrazol-5-yl)-ethyl]-urea
1-(6-Bromo-imidazo[1,2-b]pyridazin-2-yl)-3-[2-(2-isopropyl-2H-tetrazol-5-yl)-ethyl]-urea are prepared according to the following scheme:

Where: X = C or N,
Y = N & Z = C or
Y = C & Z = N

Step 1: Reaction of Intermediates A, in an analogous manner to that used in the preparation of Intermediate B1 gives the Intermediates B.

Step 2: Reaction of Intermediates B individually with the Intermediates D, in an analogous manner to that used in the preparation of intermediate E1 gives the Intermediates E.

Intermediate F1

1-(6-Bromo-benzothiazol-2-yl)-3-{2-[2-(2-fluoro-ethyl)-2H-tetrazol-5-yl]-ethyl}-urea This compound is prepared analogously to Intermediate E1 by replacing (6-bromo-imidazo[1,2-a]pyridin-2-yl)-carbamic acid phenyl ester (Intermediate B1) with imidazole-1-carboxylic acid (6-bromo-benzothiazol-2-yl)-amide (Intermediate B2) and by replacing 2-(2-isopropyl-2H-tetrazol-5-yl)-ethylamine hydrochloride (Intermediate D1) with 242-(2-fluoro-ethyl)-2H-tetrazol-5-ylFethylamine (Intermediate D3).

Intermediates F2-F7

-continued

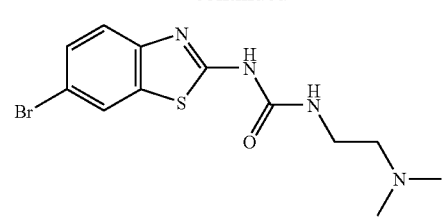
F2

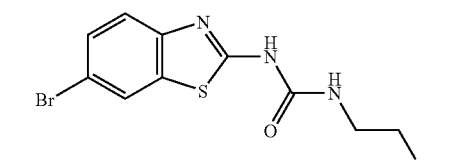
F3

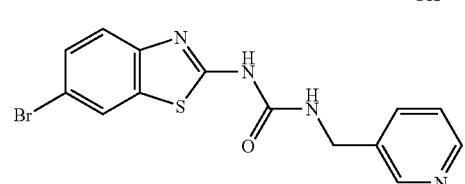
F4

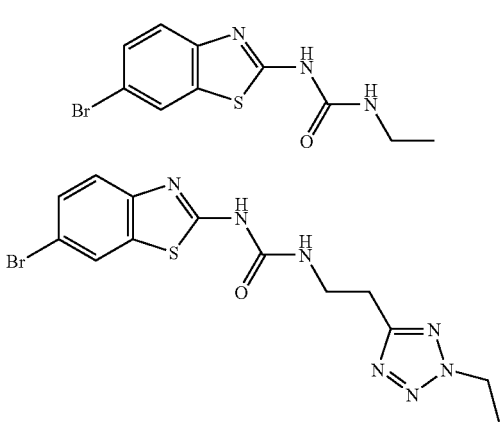
F5

F6

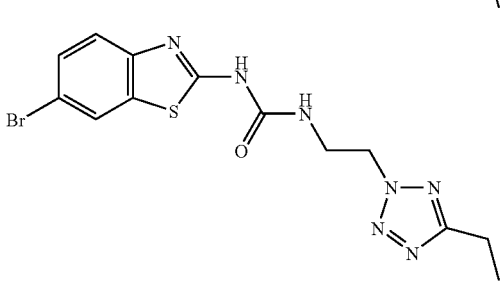
F7

These compounds namely,

F2: 1-(6-Bromo-benzothiazol-2-yl)-3-(2-dimethylamino-ethyl)-urea

F3: 1-(6-Bromo-benzothiazol-2-yl)-3-(2-hydroxy-ethyl)-urea

F4: 1-(6-Bromo-benzothiazol-2-yl)-3-pyridin-3-ylmethyl-urea

F5: 1-(6-Bromo-benzothiazol-2-yl)-3-ethyl-urea

F6: 1-(6-Bromo-benzothiazol-2-yl)-3-[2-(2-ethyl-2H-tetrazol-5-yl)-ethyl]-urea

F7: 1-(6-Bromo-benzothiazol-2-yl)-3-[2-(5-ethyl-tetrazol-2-yl)-ethyl]-urea are made analogous to Intermediate F1 by replacing 2-[2-(2-fluoro-ethyl)-2H-tetrazol-5-yl]-ethy-lamine (Intermediate D3) with the appropriate tetrazole/oxazole (Intermediates D) or commercially available amines.

Intermediates G1-G7

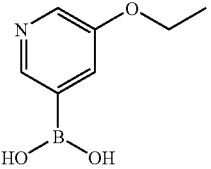
G1

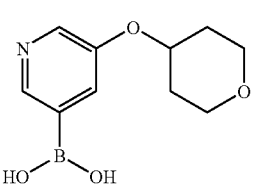
G2

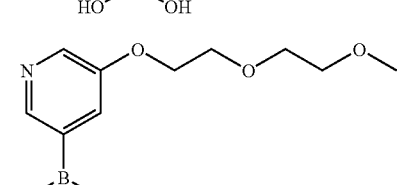
G3

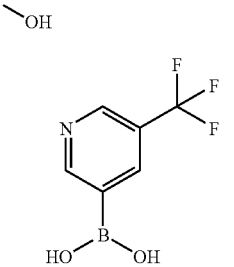
G4

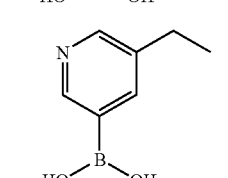
G5

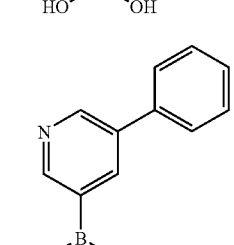
G6

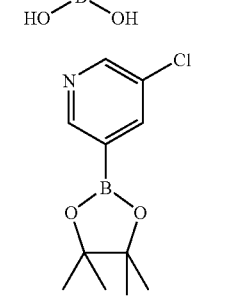
G7

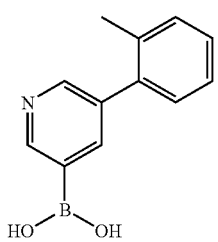

Intermediate G1

5-Methoxypyridine-3-boronic acid

Step 1: 3-Bromo-5-ethoxy-pyridine

Triphenylphosphine (0.461 g, 1.758 mmol) is added to a mixture of 3-bromo-5-hydroxy pyridine (0.3 g, 1.724 mmol) in THF (10 ml). Ethanol (0.103 ml) is added the reaction mixture is cooled to 0° C. (ice-bath). DEAD (0.277 ml, 1.758 mmol) is finally added and the mixture is warmed to room temperature and stirred overnight. The crude material is purified by flash chromatography by wet loading onto a 50 g silica column eluting with 3:1 iso-hexanes:EtOAc to afford the title compound as a yellow oil, [MH+ 201.88].

Step 2: 5-Methoxypyridine-3-boronic acid

A cooled (−78° C.) solution of 3-bromo-5-ethoxy-pyridine (0.187 g, 0.926 mmol) in dry THF (7 ml) is treated with triethyl borate (0.161 ml, 0.945 mmol) followed by dropwise addition of 1.46M n-BuLi in hexanes (0.7 ml, 1.018 mmol). The reaction mixture is allowed to warm to room temperature overnight and then treated with 5M HCl (1 ml). After stirring for 10 minutes, the THF is removed in vacuo and the aqueous layer is extracted with EtOAc (10 ml). The aqueous layer is concentrated in vacuo and dried under vacuum overnight to afford the title compound as the HCl.LiCl salt, [MH+ 168.01].

Intermediates G2-G4

These compounds namely,
G2: 5-(Tetrahydro-pyran-4-yloxy)pyridine-3-boronic acid
G3: 5-[2-(2-Methoxy-ethoxy)-ethoxy]pyridine-3-boronic acid
G4: 5-Trifluoromethylpyridine-3-boronic acid
are prepared analogously to Intermediate G1 by replacing 3-bromo-5-ethoxy-pyridine—with the corresponding aryl or heteroary bromides.

Intermediate G5

5-Ethylpyridine-3-boronic acid

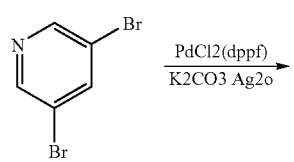

Step 1: 3-Bromo-5-ethyl-pyridine 3,5-dibromo-pyridine (0.4 g, 1.688 mmol), potassium carbonate (0.7 g, 5.064 mmol), [1,1′-Bis(diphenylphosphino)ferrocene]palladium(II) chloride (0.138 g, 0.169 mmol), silver(I) oxide (0.902 g, 4.22 mmol), ethyl boronic acid (0.150 g, 2.03 mmol) and THF (8 ml) are mixed together, purged with argon and heated to reflux overnight. After cooling to room temperature the reaction mixture is filtered through Celite® (filter agent) washing with DCM. The DCM is reduced in vacuo and the residue is purified by flash chromatography by loading onto a 20 g silica column eluting with DCM to afford the title compound, [MH+ 185.91 and 187.91].

Step 2: 5-Ethylpyridine-3-boronic acid

This compound is made analogous to step 2 Intermediate G1, by replacing 3-bromo-5-ethoxy-pyridine with 3-bromo-5-ethyl-pyridine to afford the title compound as the HCl.LiCl salt. [MH+ 152.03].

Intermediate G6

5-Phenylpyridine-3-boronic acid

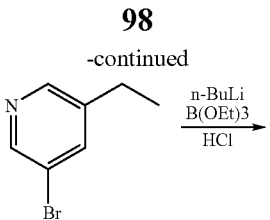

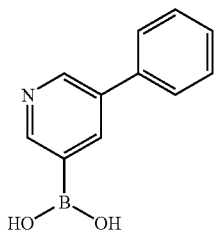

Step 1: 3-Bromo-5-phenyl-pyridine

Phenylboronic acid (0.618 g, 5.065 mmol) is stirred in a mixture of DME (20 ml) and 2M $Na_2CO_3$ for 20 minutes. 3,5-dibromopyridine (1.0 g, 4.221 mmol) is added followed by $PdCl2(Ph3P)_2$ (0.296 g, 0.4221 mmol) and the mixture is heated to 100° C. overnight. The DME layer is removed and is diluted with EtOAc, washing with 5M HCl (2×20 ml) then back extracted with EtOAc (70 ml). The acidic aqueous phase is basified with 6M NaOH (50 ml) and extracted with DCM (3×100 ml). The combined organic extracts are dried over $MgSO_4$, filtered and evaporated to an oil which is stirred in iso-hexanes (15 ml) and the resulting solid is removed washing with a further 10 ml of iso-hexanes. Concentration of the organics in vacuo affords the title compound as a white solid MH+[235.74].

Step 2: 5-Phenylpyridine-3-boronic acid

This compound is made analogous to step 2 intermediate G1, by replacing 3-Bromo-5-ethoxy-pyridine with 3-Bromo-5-phenyl-pyridine to afford the title compound as the HCl.LiCl salt [MH+200].

Intermediate G7

3-Chloro-5-(4,4,5,5-tetramethyl-[1,3,2]dioxaborolan-2-yl)-pyridine

3-Bromo-3-chloropyridine (0.5 g, 2.6 mmol), bis(pinacolato)diboron (0.79 g, 3/12 mmol), [1,1'-Bis(diphenylphosphino)ferrocene]palladium(II) chloride (0.127 g, 0.15 mmol), potassium acetate (0.77 g, 7.8 mmol) and DMF (10 ml) are stirred together at room temperature for 10 minutes whilst bubbling argon through the solution. The reaction mixture is heated to 100° C. for 90 minutes, cooled to room temperature and purified by flash chromatography by pre-absorbing onto silica, eluting with 5:1 EtOAc:iso-hexanes to afford the title compound.

Intermediate G8

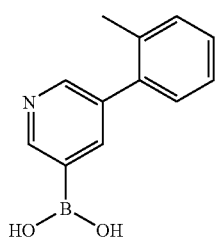

This compound is made analogously to Intermediate G6 by replacing phenylboronic acid with 2-methylphenylboronic acid to afford the title compound as the HCl.LiCl salt.

Intermediate G9

1-[5-(4,4,5,5-Tetramethyl-[1,3,2]dioxaborolan-2-yl)-pyridin-3-yl]-ethanone

Step 1: 5-Bromo-nicotinoyl chloride

5-Bromonicotinic acid (1 g, 4.950 mmol) is placed in a 100 ml round bottomed flask and purged with Argon. Dry THF (20 ml) is added and the resulting solution is treated with NaH (60% dispersed in mineral oil) (0.202 g, 5.049 mmol) over a period of 5 minutes. The reaction mixture is stirred at room temperature for 10 minutes and then oxalyl chloride (0.453 ml, 5.198 mmol) is added slowly over 5 minutes followed by dry DMF (10 ul). The reaction mixture is stirred for a further 5 minutes, filtered through filter paper, concentrated in vacuo and dried under vacuum to afford the title compound.

Step 2: 1-(5-Bromo-pyridin-3-yl)-ethanone

5-Bromo-nicotinoyl chloride (0.5 g, 2.268 mmol) is suspended in THF (24 ml) at room temperature under an atmosphere of Argon. $Fe(acac)_3$ (0.04 g, 0.113 mmol) is added and the reaction mixture is stirred for 10 minutes until a solution forms. The reaction mixture is cooled to −78° C. and a solution of MeMgBr (3M in diethyl ether, 0.907 ml, 2.722 mmol) is added dropwise with stirring for 2 hours at −78° C. On warming to room temperature silica is added to the reaction mixture and the solvents are reduced in vacuo. Purification by flash chromatography eluting with 50:50 EtOAc/iso-hexanes affords the title compound as a yellow solid [MH+199.90 and 201.90].

Step 3: 1-[5-(4,4,5,5-Tetramethyl-[1,3,2]dioxaborolan-2-yl)-pyridin-3-yl]-ethanone This compound is prepared analogously to Intermediate G7 by replacing 3-bromo-3-chloropyridine with 1-(5-bromo-pyridin-3-yl)-ethanone to afford the title compound [MH+ 166.01].

The compounds of the invention were synthesized according to the examples provided above. PI3K inhibitory ($IC_{50}$) values of the compounds were determined according to Biological Method 1.

Each of the compounds screened in Table 1 exhibited an $IC_{50}$ value of less than about 25 μM with respect to inhibition of PI3K. Many of the Examples of Table 1 exhibited $IC_{50}$ values of less than about 10 μM, and less than about 1 μM, and even less than about 0.1 μM with respect to inhibition of PI3K. For this reason, each of the compounds is individually preferred and preferred as a member of a group.

BIOLOGICAL EXAMPLES

Biological Method 1

Phosphorylation Assays
Assay 1: Homogenous Solution Phase Assay

Compounds to be tested are dissolved in DMSO and directly distributed into 384-well flashplates at 1.25 μL per well. To start the reaction, 20 μL of 6 nM PI3 kinase are added into each well followed by 20 μL of 400 nM ATP containing a trace of radiolabeled ATP and 900 nM 1-alpha-phosphatidylinositol (PI). The plates are briefly centrifuged to remove any air gap. The reaction is performed for 15 minutes and then stopped by the addition of 20 μL of 100 mM EDTA. The stopped reaction is incubated overnight at RT to allow the lipid substrate to bind by hydrophobic interaction to the surface of the flashplate. The liquid in the wells is then washed away, and the labeled substrate is detected with scintillation counting.

Assay 2: One Step Solid Phase Assay

This method is similar to Assay 1 except that the lipid substrate (1-alpha-phosphatidylinositol (PI)) is first dissolved in a coating buffer and incubated on flashplate at room temperature overnight to allow the lipid substrate to bind by hydrophobic interaction to the surface of the flashplate. Unbound substrate is then washed away. On the day of assay, 20 μL of 6 nM PI3 kinase are added into each well followed by 20 μL of 400 nM ATP containing trace of radiolabeled ATP. Compounds are added together with enzyme and ATP to the lipid-coated plates. The plates are briefly centrifuged to remove any air gap. The reaction is performed for two to three hours. The reaction is stopped by addition of 20 μL of 100 mM EDTA or by immediate plate washing. Phosphorylated lipid substrate is detected by scintillation counting.

Assay 3: ATP Depletion Assay

Compounds to be tested are dissolved in DMSO and directly distributed into a black 384-well plate at 1.25 μL per well. To start the reaction, 25 μL of 10 nM PI3 kinase and 5 μg/mL 1-alpha-phosphatidylinositol (PI) are added into each well followed by 25 μL of 2 μM ATP. The reaction is performed until approx 50% of the ATP is depleted, and then stopped by the addition of 25 μL of KinaseGlo solution. The stopped reaction is incubated for 5 minutes and the remaining ATP is then detected via luminescence.

Biological Method 2 pSer$^{473}$ Akt Assays to Monitor PI3K Pathway

In this method, an assay for measuring the PI3K-mediated pSer$^{473}$-Akt status after treatment with representative inhibitor compounds of the preferred embodiments is described.

A2780 cells were cultured in DMEM supplemented with 10% FBS. L-glutamine, sodium pyruvate, and antibiotics. Cells were plated in the same medium at a density of 15,000 cells per well into 96 well tissue culture plates, with outside wells vacant, and allowed to adhere overnight.

Test compounds supplied in DMSO were diluted further into DMSO at 500 times the desired final concentrations before dilution into culture media to 2 times the final concentrations. Equal volumes of 2× compounds were added to the cells in 96 well plates and incubated at 37° C. for one hour. The media and compounds were then removed, the plates chilled and cells lysed in a lysis buffer (150 mM NaCl, 20 mM Tris pH 7.5, 1 mM EDTA, 1 mM EGTA, 1% Triton X-100) supplemented with phosphatase and protease inhibitors. After thorough mixing, lysates were transferred to both pSer473Akt and total Akt assay plates from Meso Scale Discovery (MSD), and incubated overnight with shaking at 4° C. The plates were washed with 1×MSD wash buffer and the captured analytes detected with secondary antibodies. After incubation with the secondary antibody at room temperature for 1-2 hours, the plates were washed again and 1.5× concentration of Read Buffer T (MSD) was added to the wells.

The assays were read on a SECTOR Imager 6000 instrument (Meso Scale Discovery). Ratios of the signal from pSer473Akt and total Akt assays were used to correct for any variability and the percent inhibition of pSer473Akt from the total signal seen in cells treated with compound versus DMSO alone was calculated and used to determine EC$_{50}$ values for each compound.

All of the references cited herein are hereby incorporated by reference in their entirety.

While a number of preferred embodiments of the invention and variations thereof have been described in detail, other modifications and methods of use within the scope of the claims appended hereto will be readily apparent to those of skill in the art.

What is claimed is:

1. A compound having Formula I, a stereoisomer, tautomer, or pharmaceutically acceptable salt thereof,

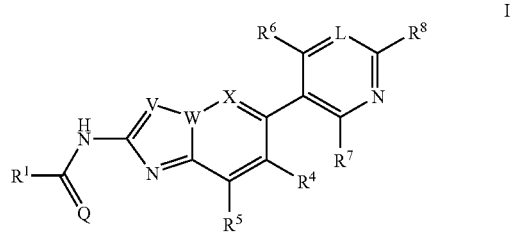

wherein:

Q is O or S;

X is CR$^3$ or N;

W is C or N;

V is CR$^2$, O or S;

L is CR$^9$ or N;

R$^1$ is —Z—Y—R$^{10}$,

Z is NHCH$_2$C(R$^{11}$)R$^{12}$,

Y is a bond or —CON(R$^{13}$)—;

R$^{10}$ is C$_1$-C$_6$-alkylaminocarbonyl, C$_1$-C$_6$-alkoxycarbonyl, where each alkyl is independently optionally substituted by one or more halo, hydroxyl or C$_1$-C$_6$-alkoxy groups, or R$^{10}$ is a mono-cyclic heteroaromatic ring having one or more ring heteroatoms selected from the group consisting of oxygen, nitrogen and sulphur, said ring being optionally substituted by one or more halo, hydroxyl, C$_1$-C$_6$-alkyl or C$_1$-C$_6$-alkoxy groups, where said alkyl and alkoxy are optionally further substituted by one or more halo, hydroxyl or C$_1$-C$_6$-alkoxy groups;

R$^{11}$ and R$^{12}$ are independently selected from hydrogen, halo, hydroxy and C$_1$-C$_6$-alkyl where said alkyl group is optionally substituted by one or more halo, hydroxyl or C$_1$-C$_6$-alkoxy groups;

R$^{13}$ is hydrogen or C$_1$-C$_6$-alkyl;

R$^2$ and R$^3$ are independently selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, SO$_3$H, sulfonyl, substituted sulfonyl, sulfonyloxy, thioacyl, thiol, alkylthio, and substituted alkylthio;

$R^4$ and $R^5$ are independently selected from the group consisting of hydrogen, halogen, cyano, nitro, amino, substituted amino, alkoxy, substituted alkoxy, alkyl, and substituted alkyl;

$R^6$ is selected from the group consisting of hydrogen, halogen, cyano, nitro, alkoxy, substituted alkoxy, alkyl, and substituted alkyl;

$R^7$ and $R^9$ are independently selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acyloxy, aminocarbonyl, aminothiocarbonyl, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, and substituted alkylthio;

$R^8$ is selected from the group consisting of hydrogen, alkyl, —CO—$R^{8a}$, substituted alkyl, and a three- to seven-membered ring selected from the group consisting of cycloalkyl, substituted cycloalkyl, heterocyclyl, and substituted heterocyclyl; and $R^{8a}$ is selected from the group consisting of alkyl, substituted alkyl, alkoxy, substituted alkoxy, amino, substituted amino, and alkylamino.

2. The compound according to claim 1 having Formula II, a stereoisomer, tautomer, or pharmaceutically acceptable salt thereof,

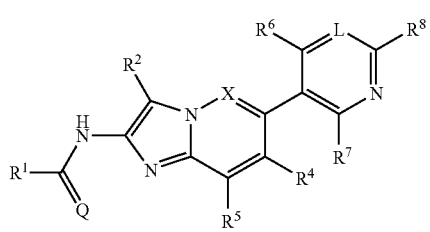

II wherein:
Q is O or S;
X is $CR^3$ or N;
L is $CR^9$ or N;
$R^1$ is —Z—Y—$R^{10}$;
$R^2$ and $R^3$ are independently selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, and substituted alkylthio;

$R^4$ and $R^5$ are independently selected from the group consisting of hydrogen, halogen, cyano, nitro, amino, substituted amino, alkoxy, substituted alkoxy, alkyl, and substituted alkyl;

$R^6$ is selected from the group consisting of hydrogen, halogen, cyano, nitro, alkoxy, substituted alkoxy, alkyl, and substituted alkyl;

$R^7$ and $R^9$ are independently selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acyloxy, aminocarbonyl, aminothiocarbonyl, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, and substituted alkylthio;

$R^8$ is selected from the group consisting of hydrogen, alkyl, —CO—$R^{8a}$, substituted alkyl, and a three- to seven-membered ring selected from the group consisting of cycloalkyl, substituted cycloalkyl, heterocyclyl, and substituted heterocyclyl;

$R^{8a}$ is selected from the group consisting of alkyl, substituted alkyl, alkoxy, substituted alkoxy, amino, substituted amino, and alkylamino;

Z is $NHCH_2C(R^{11})R^{12}$,

Y is a bond or —$CON(R^{13})$—

$R^{10}$ is $C_1$-$C_6$-alkylaminocarbonyl, $C_1$-$C_6$-alkoxycarbonyl, where each alkyl is independently optionally substituted by one or more halo, hydroxyl or $C_1$-$C_6$-alkoxy groups, or $R^{10}$ is a mono-cyclic heteroaromatic ring having one or more ring heteroatoms selected from the group consisting of oxygen, nitrogen and sulphur, said ring being optionally substituted by one or more halo, hydroxyl, $C_1$-$C_6$-alkyl or $C_1$-$C_6$-alkoxy groups, where said alkyl and alkoxy are optionally further substituted by one or more halo, hydroxyl or $C_1$-$C_6$-alkoxy groups;

$R^{11}$ and $R^{12}$ are independently selected from hydrogen, halo, hydroxy and $C_1$-$C_6$-alkyl where said alkyl group is optionally substituted by one or more halo, hydroxyl or $C_1$-$C_6$-alkoxy groups; and $R^{13}$ is hydrogen or $C_1$-$C_6$-alkyl.

3. The compound of claim 2, wherein $R^{10}$ is a mono-cyclic heteroaromatic ring having one or more ring heteroatoms selected from the group consisting of oxygen, nitrogen and sulphur, said ring being optionally substituted by one or more halo, hydroxyl, $C_1$-$C_6$-alkyl or $C_1$-$C_6$-alkoxy groups, where said alkyl and alkoxy are optionally further substituted by one or more halo, hydroxyl or $C_1$-$C_6$-alkoxy groups.

4. A compound having Formula III, a stereoisomer, tautomer, or pharmaceutically acceptable salt thereof;

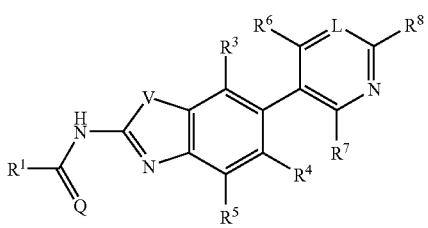

wherein:
Q is O or S;
V is O or S;
L is $CR^9$ or N;
$R^1$ is selected from the group consisting of hydrogen, alkyl, substituted alkyl, alkenyl, substituted alkenyl, alkynyl, substituted alkynyl, alkoxy, substituted alkoxy, amino, substituted amino, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, and alkylamino;
$R^3$ is selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, and substituted alkylthio;
$R^4$ and $R^5$ are independently selected from the group consisting of hydrogen, halogen, cyano, nitro, amino, substituted amino, alkoxy, substituted alkoxy, alkyl, and substituted alkyl;
$R^6$ is selected from the group consisting of hydrogen, halogen, cyano, nitro, alkoxy, substituted alkoxy, alkyl, and substituted alkyl;
$R^7$ and $R^9$ are independently selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acyloxy, aminocarbonyl, aminothiocarbonyl, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, and substituted alkylthio;
$R^8$ is selected from the group consisting of hydrogen, alkyl, $-CO-R^{8a}$, substituted alkyl, and a three- to seven-membered ring selected from the group consisting of cycloalkyl, substituted cycloalkyl, heterocyclyl, and substituted heterocyclyl; and
$R^{8a}$ is selected from the group consisting of alkyl, substituted alkyl, alkoxy, substituted alkoxy, amino, substituted amino, and alkylamino.

5. The compound of claim 4, wherein
$R^1$ is $-Z-Y-R^{10}$,
Z is $NHCH_2C(R^{11})R^{12}$,
Y is a bond or $-CON(R^{13})-$;
$R_{10}$ is $C_1$-$C_6$-alkylaminocarbonyl, $C_1$-$C_6$-alkoxycarbonyl, where each alkyl is independently optionally substituted by one or more halo, hydroxyl or $C_1$-$C_6$-alkoxy groups, or $R^{10}$ is a mono-cyclic heteroaromatic ring having one or more ring heteroatoms selected from the group consisting of oxygen, nitrogen and sulphur, said ring being optionally substituted by one or more halo, hydroxyl, $C_1$-$C_6$-alkyl or $C_1$-$C_6$-alkoxy groups, where said alkyl and alkoxy are optionally further substituted by one or more halo, hydroxyl or $C_1$-$C_6$-alkoxy groups;
$R^{11}$ and $R^{12}$ are independently selected from hydrogen, halo, hydroxy and $C_1$-$C_6$-alkyl where said alkyl group is optionally substituted by one or more halo, hydroxyl or $C_1$-$C_6$-alkoxy groups; and
$R^{13}$ is hydrogen or $C_1$-$C_6$-alkyl.

6. The compound of claim 5, wherein
$R^{10}$ is a mono-cyclic heteroaromatic ring having one or more ring heteroatoms selected from the group consisting of oxygen, nitrogen and sulphur, said ring being optionally substituted by one or more halo, hydroxyl, $C_1$-$C_6$-alkyl or $C_1$-$C_6$-alkoxy groups, where said alkyl and alkoxy are optionally further substituted by one or more halo, hydroxyl or $C_1$-$C_6$-alkoxy groups.

7. The compound of claim 4 selected from the group consisting of
1-{2-[2-(2-Fluoro-ethyl)-2H-tetrazol-5-yl]ethyl}-3-(6-pyridin-3-yl-benzothiazol-2-yl)-urea;
1-{2-[2-(2-Fluoro-ethyl)-2H-tetrazol-5-yl]ethyl}-3-[6-(6-methoxy-pyridin-3-yl)-benzothiazol-2-yl]-urea;
1-(2-Dimethylamino-ethyl)-3-[6-(6-methoxy-pyridin-3-yl)-benzothiazol-2-yl]-urea;
1-(2-Hydroxy-ethyl)-3-[6-(6-methoxy-pyridin-3-yl)-benzothiazol-2-yl]-urea;
1-[6-(6-Methoxy-pyridin-3-yl)-benzothiazol-2-yl]-3-pyridin-3-ylmethyl-urea;
1-Ethyl-3-[6-(6-methoxy-pyridin-3-yl)-benzothiazol-2-yl]urea;
1-{2-[2-(2-Fluoro-ethyl)-2H-tetrazol-5-yl]-ethyl}-3-{6-[5(morpholine-4-carbonyl)-pyridin-3-yl]-benzothiazol-2-yl}-urea;
1-{2-[2-(2-Fluoro-ethyl)-2H-tetrazol-5-yl]-ethyl}-3-[6-(5-trifluoromethyl-pyridin-3-yl)-benzothiazol-2-yl]urea;
1-[2-(2-Ethyl-2H-tetrazol-5-yl)-ethyl]-3-[6-(5-trifluoromethyl-pyridin-3-yl)-benzothiazol-2-yl]-urea;
1-[2-(2-Isopropyl-2H-tetrazol-5-yl)-ethyl]-3-[6-(5-trifluoromethyl-pyridin-3-yl)-benzothiazol-2-yl]-urea;
1-[2-(5-Ethyl-tetrazol-2-yl)-ethyl]-3-[6-(5-trifluoromethyl-pyridin-3-yl)-benzothiazol-2-yl]urea; and 1-[2-(1-Ethyl-1H-imidazol-4-yl)-ethyl]-3[6-(5-trifluoromethyl-pyridin-3-yl)-benzothiazol-2-yl]-urea, or a stereoisomer, tautomer, or a pharmaceutically acceptable salt thereof.

8. A pharmaceutical composition, comprising:
a pharmaceutically acceptable carrier and
a therapeutically effective amount of compound as defined in claim 1, a stereoisomer, tautomer, or pharmaceutically acceptable salt thereof.

9. The compound according to claim 2, wherein $R^2$ is hydrogen.

10. The compound according to claim 2, wherein X is $CR^3$.

11. The compound according to claim 10, wherein $R^3$ is hydrogen.

12. The compound according to claim 2, wherein $R^4$ and $R^5$ are both hydrogen.

13. The compound according to claim 2, wherein $R^6$ is hydrogen.

14. The compound according to claim 2, wherein $R^7$ is hydrogen.

15. The compound according to claim 2, wherein $R^8$ is hydrogen, alkyl or alkoxy.

16. The compound according to claim 2, wherein $R^9$ is selected from the group consisting of hydrogen, trifluoromethyl, methoxy, fluoro, methyl, and bromo.

* * * * *